US006723830B2

(12) United States Patent
Ben-Sasson

(10) Patent No.: US 6,723,830 B2
(45) Date of Patent: Apr. 20, 2004

(54) SHORT PEPTIDES WHICH SELECTIVELY MODULATE THE ACTIVITY OF PROTEIN KINASES

(75) Inventor: Shmuel A. Ben-Sasson, Jerusalem (IL)

(73) Assignees: Children's Medical Center Corporation, Boston, MA (US); Yissum Research and Development, Jerusalem (IL)

( * ) Notice: Subject to any disclaimer, the term of this patent is extended or adjusted under 35 U.S.C. 154(b) by 0 days.

(21) Appl. No.: 10/038,612

(22) Filed: Jan. 8, 2002

(65) Prior Publication Data

US 2002/0160478 A1 Oct. 31, 2002

Related U.S. Application Data

(63) Continuation of application No. 09/161,094, filed on Sep. 25, 1998, now abandoned.

(51) Int. Cl.[7] .................. A61K 38/04; A61K 38/16; C07K 7/00; C07K 14/00
(52) U.S. Cl. .................. 530/317; 514/11; 514/12; 514/13; 514/14; 514/15; 514/16; 514/17; 530/324; 530/325; 530/326; 530/327; 530/328; 530/329; 530/330
(58) Field of Search .................. 514/9, 10, 11, 514/12, 13, 14, 15, 16, 17; 530/3, 7, 318, 319, 320, 321, 324, 325, 326, 327, 328, 329, 330; 435/15, 16, 17, 29

(56) References Cited

U.S. PATENT DOCUMENTS

| | | | |
|---|---|---|---|
| 4,455,290 A | * 6/1984 | Olexa et al. | 424/1.69 |
| 5,200,327 A | 4/1993 | Garvin et al. | 435/69.3 |
| 5,200,510 A | 4/1993 | Kumar et al. | 530/413 |
| 5,250,516 A | 10/1993 | Urry | 514/17 |
| 5,340,800 A | 8/1994 | Liu et al. | 514/12 |
| 5,418,147 A | 5/1995 | Huang et al. | 435/69.1 |
| 5,439,829 A | * 8/1995 | Anderson et al. | 436/518 |
| 5,439,887 A | 8/1995 | Hamon et al. | 514/13 |
| 5,478,810 A | 12/1995 | Stuber et al. | 514/17 |
| 5,527,681 A | 6/1996 | Holmes | 435/6 |
| 5,556,744 A | 9/1996 | Weiner et al. | 435/5 |
| 5,594,105 A | 1/1997 | Comoglio et al. | 530/326 |
| 5,688,513 A | 11/1997 | Binger et al. | 424/271.1 |
| 5,693,325 A | 12/1997 | Kahn | 424/188.1 |
| 5,763,198 A | 6/1998 | Hirth et al. | 435/7.21 |
| 5,777,093 A | 7/1998 | Shiloh et al. | 536/23.5 |
| 5,827,692 A | 10/1998 | Tang et al. | 435/69.1 |
| 5,843,462 A | 12/1998 | Conti-Fine | 424/245.1 |

(List continued on next page.)

FOREIGN PATENT DOCUMENTS

| | | |
|---|---|---|
| WO | WO 93/16703 A1 | 9/1993 |
| WO | WO 94/07913 A1 | 4/1994 |
| WO | WO 96/32411 A1 | 10/1996 |
| WO | WO 97/25341 A1 | 7/1997 |
| WO | WO 97/33908 A1 | 9/1997 |
| WO | WO-97/47314 A1 * | 12/1997 |
| WO | WO 98/32017 A2 | 7/1998 |

OTHER PUBLICATIONS

Morelli et al. Structure–activity relationships for some elastin–derived peptide chemoattractants. J. Peptide Res. vol. 49, No. 6, pp. 492–499 (Jun. 1997).*

(List continued on next page.)

Primary Examiner—Jeffrey E. Russel
(74) Attorney, Agent, or Firm—Browdy and Neimark, P.L.L.C.

(57) ABSTRACT

Peptides which are peptide derivatives of the αD region of a protein kinase can modulate the activity of protein kinases. The activity of a protein kinase in a subject can be modulated by administering one or more of these peptides.

34 Claims, 23 Drawing Sheets

U.S. PATENT DOCUMENTS

| | | | |
|---|---|---|---|
| 5,891,640 A | 4/1999 | DeLeys | 435/7.1 |
| 5,910,478 A | 6/1999 | Hlavka et al. | 514/9 |
| 6,011,014 A | 1/2000 | Andersen et al. | 514/15 |
| 6,017,883 A | 1/2000 | Cooper, Jr. | 514/12 |
| 6,228,989 B1 | 5/2001 | Traugh et al. | 530/350 |
| 6,232,287 B1 | 5/2001 | Ruoslahti et al. | 514/2 |

OTHER PUBLICATIONS

Zhou et al. Leukocyte Response Integrin and Integrin–Associated protein . . . J. Exp. Med. vol. 178, pp. 1165–1174 (Oct. 1993).*

Alemáet al, "Differentiation of PC12 phaeochromocytoma cells induced by v–src oncogene", *Nature* 316:557–559 (1985).

Birchall et al, "Ro 32–0432, a Selective and Orally Active Inhibitor of Protein Kinase C Prevents T–Cell Activation", *J Pharmacol Exp Ther* 268(2):922–929 (1994).

Bradshaw et al, "Therapeutic potential of protein kinase C inhibitors", *Agents Actions* 38:135–147 (1993).

Dudek et al, "Regulation of Neuronal Survival by the Serine–Threonine Protein Kinase Akt", *Science* 275:661–665 (1997).

Franke et al, "P13K: Downstream AKTion Blocks Apoptosis", *Cell* 88:435–437 (1997).

Freedman et al, "Desensitization of G Protein–Coupled Receptors", *Recent Prog Horm Res* 51:319–353 (1996).

Glover et al, "Polo Kinase: The Choreographer of the Mitotic Stage?", *J Cel Biol* 135(6)(2):1681–1684 (1996).

Hanks et al, "The Eukaryotic Protein Kinase Superfamily", *The Protein Kinase Facts Book*, vol. 1 (Hardie et al, eds), Academic Press, Chapter 2 (1995).

Hanks et al, "The eukaryotic protein kinase superfamily: kinase (catalytic) domain structure and classification", *FASEB J* 9:576–596 (1995).

Hemmings et al, "Akt Signaling: Linking Membrane Events to Life and Death Decisions", *Science* 275:628–631 (1997).

Hubbard et al, "Crystal structure of the tyrosine kinase domain of the human insulin receptor", *Nature* 372:746–753 (1994).

Hughes AL, "Evolution of the *src*–Related Protein Tyrosine Kinases", *J Mol Evol* 42:247–256 (1996).

Inazu et al, "Purification and characterization of a novel dimeric 20 alpha–hydroxysteroid dehydrogenase from Tetrahymena pyriformis", *Biochem J* 297:195–200 (1994).

Kohn et al, "Expression of a Constitutively Active Akt Ser/Thr Kinase in 3T3–L1 Adipocytes Stimulates Glucose Uptake and Glucose Transporter 4 Translcoation", *J Biol Chem* 271(49):31372–31378 (1996).

Lovrić et al, "Activation of Mil/Raf protein kinases in mitotic cells", *Oncogene* 12:1109–1116 (1996).

Lange–Carter et al, "A Divergence in the MAP Kinase Regulatory Network Defined by MEK Kinase and Raf", *Science* 260:315–318 (1993).

Mason IJ, "The Ins and Outs of Fibroblast Growth Factors", *Cell* 78:547–552 (1994).

McKenna et al, "Atomic structure of the degraded procapsid particle of the bacteriophage G4: induced structural changes in the presence of calcium ions and functional implications," J. Mol. Biol. 256:736–750 (1996).

Mohammadi et al, "Structureo f the FGF Receptor Tyrosine Kinase Domain Reveals a Novel Autoinhibitory Mechanism", *Cell* 86:577–587 (1996).

Nishizuka Y, "Protein kinase C and lipid signaling for sustained cellular responses", *FASEB J* 9:484–496 (1995).

Petit G, *Synthetic Peptides*, vol 4., Amsterdam: Elsevier Sci. Pub. Co. pp 212, 223, 470 (1976).

Simmons et al, "Identification of an Early–Growth Response Gene Encoding a Novel Putative Protein Kinase", *Mol Cel Biol* 12:4164–4169 (1992).

Taylor et al, "cAMP–dependent protein kinase defines a family of enzymes", *Phil Trans R Soc Lond B* 340:315–324 (1993).

* cited by examiner

Figure 1A

| No. | Kinase-Subclass | Family | Sub | Protein | αD sequence |
|---|---|---|---|---|---|
| 1 | Serine/Threonine | RAF | | c-Raf | TQWCEGSSLYKHLHVQETKF |
| 2 | Serine/Threonine | RAF | | Araf | TQWCEGSSLYHHLHVADTRF |
| 3 | Serine/Threonine | RAF | | Braf | TQWCEGSSLYHHLHIIETKF |
| 4 | Serine/Threonine | CAPK | | cAPKa | MEYVPGGEMFSHLRRIGRF |
| 4 | Serine/Threonine | CAPK | | cAPKb | MEYVPGGEMFSHLRRIGRF |
| 5 | Serine/Threonine | CAPK | | cAPKg | MEYVPGGEMFSRLQRVGRF |
| 6 | Serine/Threonine | PKC | | PKCa | MEYVNGGDLMYHIQQVGKF |
| 7 | Serine/Threonine | PKC | | PKCb | MEYVNGGDLMYHIQQVGRF |
| 8 | Serine/Threonine | PKC | | PKCg | MEYVTGGDLMYHIQQLGKF |
| 9 | Serine/Threonine | PKC | | PKCd | MEFLNGGDLMFHIQDKGRF |
| 10 | Serine/Threonine | PKC | | PKCe | MEYVNGGDLMFQIQRSRKF |
| 11 | Serine/Threonine | PKC | | PKCet | MEFVNGGDLMFHIQKSRRF |
| 12 | Serine/Threonine | PKC | | PKCth | MEYLNGGDLMYHIQSCHKF |

Figure 1B

| 13 | Serine/Threonine | Akt/PKB | | Akt1/Raca | MEYANGGELFFHLSRERVF |
|---|---|---|---|---|---|
| 13 | Serine/Threonine | Akt/PKB | | Akt2/Racb | MEYANGGELFFHLSRERVF |
| 14 | Serine/Threonine | GSK3 | | GSK3a | LEYVPETVYRVARHFTKAKLII |
| 15 | Serine/Threonine | GSK3 | | GSK3b | LDYVPETVYRVARHYSRAKQTL |
| 16 | Serine/Threonine | CK II | | CK IIa | FEHVNNTDFKQLYQTL |
| 17 | Serine/Threonine | CK II | | CK IIa' | FEYINNTDFKQLYQIL |
| 18 | Serine/Threonine | bARK1,2 | | bARK1 | LDLMNGGDLHYHLSQHGVF |
| 18 | Serine/Threonine | bARK1,2 | | bARK2 | LDLMNGGDLHYHLSQHGVF |
| 19 | Serine/Threonine | GRK1 | | GRK1 | MTIMNGGDIRYHIYNVDEDNPGF |
| 20 | Serine/Threonine | GRK4 | | GRK4 | LTIMNGGDLKFHIYNLGNPGF |
| 21 | Serine/Threonine | GRK5 | | GRK5 | LTIMNGGDLKFHIYNMGNPGF |
| 22 | Serine/Threonine | GRK6 | | GRK6 | LTLMNGGDLKFHIYHMGQAGF |

Figure 1C

| 23 | Serine/Threonine | CaMK | | CaMK I | MQLVSGGELFDRIVEKGGY |
|---|---|---|---|---|---|
| 24 | Serine/Threonine | CaMK | | CaMK IIa | FDLVTGGELFEDIVAREYY |
| 24 | Serine/Threonine | CaMK | | CaMK IIb | FDLVTGGELFEDIVAREYY |
| 24 | Serine/Threonine | CaMK | | CaMK IIg | FDLVTGGELFEDIVAREYY |
| 24 | Serine/Threonine | CaMK | | CaMK IId | FDLVTGGELFEDIVAREYY |
| 25 | Serine/Threonine | POLO | | Plk | LELCRRRSLLELHKRRKAL |
| 26 | Serine/Threonine | POLO | | Plx1 | LELCRRRSLLELHKRRKAV |
| 27 | Serine/Threonine | POLO | | polo | LELCKKRSMMELHKRRKSI |
| 28 | Serine/Threonine | POLO | | SNK | LEYCSRRSMAHILKARKVL |
| 29 | Serine/Threonine | POLO | | CDC5 | LEICPNGSLMELLKRRKVL |
| 30 | Serine/Threonine | POLO | | Sak | LEMCHNGEMNRYLKNRVKPF |
| 31 | Serine/Threonine | POLO | | Prk | LELCSRKSLAHIWKARHTL |

Figure 1D

| 31 | Serine/Threonine | POLO | | Fnk | LELCSRKSLAHIWKARHTL |
|---|---|---|---|---|---|
| 32 | Serine/Threonine | POLO | | Plo1 | LELCEHKSLMELLRKRKQL |
| 33 | Serine/Threonine | MARK/p78 | | MARK1 | MEYASGGEVFDYLVAHGRM |
| 33 | Serine/Threonine | MARK/p78 | | MARK2 | MEYASGGEVFDYLVAHGRM |
| 34 | Serine/Threonine | MARK/p78 | | P78 | MEYASGGKVFDYLVAHGRM |
| 35 | Serine/Threonine | CDK | | CDK2 | FEFLHQDLKKFMDASALTGI |
| 36 | Serine/Threonine | CDK | | CDK4 | FEHVDQDLRTYLDKAPPPGL |
| 37 | Serine/Threonine | CDK | | CDK6 | FEHVDQDLTTYLDKVPEPGV |
| 38 | Tyrosine | SRC | | c-Src | TEYMSKGSLLDFLKGETGKYL |
| 39 | Tyrosine | SRC | | c-Yes | TEFMSKGSLLDFLKEGDGKYL |
| 40 | Tyrosine | SRC | | Fyn | TEYMNKGSLLDFLKDGEGRAL |
| 41 | Tyrosine | SRC | | c-Fgr | TEFMCHGSLLDFLKNPEGQDL |

Figure 1E

| 42 | Tyrosine | LYN/HCK | | Lyn | TEYMAKGSLLDFLKSDEGGKV |
|---|---|---|---|---|---|
| 43 | Tyrosine | LYN/HCK | | Hck | TEFMAKGSLLDFLKSDEGSKQ |
| 44 | Tyrosine | LCK | | Lck | TEYMENGSLVDFLKTPSGIKL |
| 45 | Tyrosine | CSK | | Csk | TEYMAKGSLVDYLRSRGRSVL |
| 46 | Tyrosine | CSK | | Matk | MEHVSKGNLVNFLRTRGRALV |
| 47 | Tyrosine | FAK | | Fak | MELCTLGELRSFLQVRKYSL |
| 48 | Tyrosine | ABL | | c-Abl | TEFMTYGNLLDYLRECNRQEV |
| 49 | Tyrosine | ENDOTHELIAL | Tie/Tek | Tie | IEYAPYGNLLDFLRKSRVLETDPAFAREHGTASTL |
| 50 | Tyrosine | ENDOTHELIAL | Tie/Tek | Tek | IEYAPHGNLLDFLRKSRVLETDPAFAIANSTASTL |
| 51 | Tyrosine | ENDOTHELIAL | FGFR | Flg | VEYASKGNLREYLQARRPPGLEYCYNPSHNPEEQL |
| 52 | Tyrosine | ENDOTHELIAL | FGFR | Bek | VEYASKGNLREYLRARRPPGMEYSYDINRVPEEQM |
| 53 | Tyrosine | ENDOTHELIAL | FGFR | FGFR-3 | VEYAAKGNLREFLRARRPPGLDYSFDTCKPPEEQL |

Figure 1F

| 54 | Tyrosine | ENDOTHELIAL | FGFR | FGFR-4 | VECAAKGNLREFLRARRPPGPDLSPDGPRSSEGPL |
|---|---|---|---|---|---|
| 55 | Tyrosine | ENDOTHELIAL | PDGFR | PDGFR-a | TEYCFYGDLVNYLHKNRDSFLSHHPEKPKKELDIFGLNPA |
| 56 | Tyrosine | ENDOTHELIAL | PDGFR | PDGFR-b | TEYCRYGDLVDYLHRNKHTFLQHHSDKRRPPSAELYSNAL |
| 57 | Tyrosine | ENDOTHELIAL | Flt/Flk | Flt1 | VEYCKYGNLSNYLKSKRDLFFLNKDAALHMEPKKEKMEPG |
| 58 | Tyrosine | ENDOTHELIAL | Flt/Flk | Flt4 | VEFCKYGNLSNFLRAKRDAFSPCAEKSPEQRGRFRAMVEL |
| 59 | Tyrosine | ENDOTHELIAL | Flt/Flk | Flk1 | VEFSKFGNLSTYLRGKRNEFVPYKSKGARFRQGKDYVGEL |
| 60 | Tyrosine | HGFR | | c-Met | LPYMKHGDLRNFIRNETHNP |
| 61 | Tyrosine | HGFR | | c-Sea | LPYMRHGDLRHFIRAQERSP |
| 62 | Tyrosine | HGFR | | Ron | LPYMCHGDLLQFIRSPQRNP |
| 63 | Tyrosine | EGFR | | EGFR | TQLMPFGCLLDYVREHKDNI |
| 64 | Tyrosine | EGFR | | ErbB2 | TQLMPYGCLLDHVRENRGRL |
| 65 | Tyrosine | EGFR | | ErbB3 | TQYLPLGSLLDHVRQHRGAL |

Figure 1G

| 66 | Tyrosine | EGFR | | ErbB4 | TQLMPHGCLLEYVHEHKDNI |
|---|---|---|---|---|---|
| 67 | Tyrosine | RET | | Ret | VEYAKYGSLRGFLRESRKVGPGYLGSGGSRNSSSLDHPDERAL |
| 68 | Tyrosine | TRK-NGFR | | Trk-NGFR | FEYMRHGDLNRFLRSHGPDAKLLAGGEDVAPGPL |
| 69 | Tyrosine | TRK-NGFR | | TrkB | FEYMKHGDLNKFLRAHGPDAVLMAEGNPPTEL |
| 70 | Tyrosine | TRK-NGFR | | TrkC | FEYMKHGDLNKFLRAHGPDAMILVDGQPRQAKGEL |
| 71 | Tyrosine | SYK/ZAP70 | | Syk | MEMAELGPLNKYLQQNRHV |
| 72 | Tyrosine | SYK/ZAP70 | | Zap70 | MEMAGGGPLHKFLVGKREEI |
| 73 | Tyrosine | TYK/JAK | | Jak1 | MEFLPSGSLKEYLPKNKNKI |
| 74 | Tyrosine | TYK/JAK | | Jak2 | MEYLPYGSLRDYLQKHKERI |
| 75 | Tyrosine | TYK/JAK | | Jak3 | MEYLPSGCLRDFLQRHRARL |
| 76 | Tyrosine | TYK/JAK | | Tyk2 | MEYVPLGSLRDYLPRHSI |
| 77 | Serine/Threonine | IAK | | Iak1 | LEYAPLGTVYRELQKLSKF |

Figure 1H

| 78 | Serine/Threonine | CHK | | Chk1 | LEYCSGGELFDRIEPDIGM |
|---|---|---|---|---|---|
| 79 | Serine/Threonine | IKK | | IKK-1 | MEYCSGGDLRKLLNKPENCCGL |
| 80 | Serine/Threonine | IKK | | IKK-2 | MEYCQGGDLRKYLNQFENCCGL |
| 81 | Serine/Threonine | DAPK | | DAPK | LELVAGGELFDFLAEKESL |
| 82 | Tyrosine | IRK | | IRK | MELMAHGDLKSYLRSLRPEAENNPGRPPPTL |
| 83 | Serine/Threonine | Activin/TGFbR | TGFbR | TGFbRII | TAFHAKGNLQEYLTRHVI |
| 84 | Serine/Threonine | Activin/TGFbR | ACTR | ACTRIIA | TAFHEKGSLSDFLKANVV |
| 85 | Serine/Threonine | Activin/TGFbR | ACTR | ACTRIIB | TAFHDKGSLTDYLKGNII |
| 86 | Serine/Threonine | Activin/TGFbR | ALK | ALK1 | THYHEHGSLYDFLQRQTL |
| 87 | Serine/Threonine | Activin/TGFbR | ALK | ALK2 | THYHEMGSLYDYLQLTTL |
| 88 | Serine/Threonine | Activin/TGFbR | ALK | ALK3 | TDYHENGSLYDFLKCATL |
| 89 | Serine/Threonine | Activin/TGFbR | ALK | ALK4 | SDYHEHGSLFDYLNRYTV |

Figure 1I

| 89 | Serine/Threonine | Activin/T GFbR | ALK | ALK5 | SDYHEHGSLFDYLNRYTV |
|----|------------------|----------------|-----|------|--------------------|
| 90 | Serine/Threonine | Activin/T GFbR | ALK | ALK6 | TDYHENGSLYDYLKSTTL |
| 91 | Tyrosine | DDR | | DDR1 | TDYMENGDLNQFLSAHQL |
| 92 | Tyrosine | DDR | | DDR2 | TEYMENGDLNQFLSRHEP |
| 93 | Serine/Threonine | ILK | | ILK | THWMPYGSLYNVLHEGTNFVV |
| 94 | Tyrosine | MAPK | | JNK | MELMDANLCQVIQMEL |

Figure 2A

```
Protein Kinase
c-Raf      T Q W C E G S S L Y K H L H I E T K F
Araf       S N F S D A T T I F H   I   V D S R W
Braf           Y   *       M W R   M   M *     Y
                           V           V   L cAPKa      M E Y V P G G E M F S H L R R I G R F
cAPKb      I Q F L N A A D L M F R I Q H V R K W
cAPKg      L D W A T     * I W Y Q M S Q E H V Y
           V N   I S       V Y W K V K D L K I
               *   M Q       I T N   N K K A L
                   G             L   T S S   M
                                 V     N C
                                       E M
                                       T D
                                       * R
                                         T
                                         *

PKCa       M E Y V N G G D L M F H I Q Q V G K F
PKCb       I D F L T A A E I I Y Q L N D L R R W
PKCg       L * W I Q     * M L W N M   R K H   Y
PKCd       V     M S       V V     V   K S K
PKCe                                   S C A
PKCet                                  N I
PKCth                                  E M
                                       T R
                                       * T

Akt1/Raca  M E Y A N G G E L F F H L S R E R V F
Akt2/Racb  I Q F V Q A A D I W W   I T H D K I W
DmRAC      L D W I       * M Y Y   M K *   L Y
           V N   L         V       V       M
             *   M
                 G GSK3a      L E Y V P E T V Y R V A R H Y T K A K Q I I
GSK3b      I D F I     D S I H K I I K Q F S R T N L T L
Sgg/zw3    M * W L   *   L F   L V   N W A   L R N R M
ASK-a      V     M       M W   M L       N   S Q I L V
ASK-g                          M           Q   I   M M
                               G           G   M   V V
                                               V   S
                                               G   K CK IIa     F E H V N N T D F K Q L Y Q T L
CK IIa'    W D Y I Q Q S E W R N I F N I I
           Y * F L     * Y       M W   S M
               W M               V     M V
                                       V
                                       L
```

Figure 2B

```
bARK1   L D L M N G G D L H Y H L S Q H G V F N P G F
bARK2   M T I I Q A A E I R F   I Y N V D E D G F A W
GRK1    I E M L         * M K W   M T H L E N P Q W   Y
GRK4    V S V V           V       V F   M A Q A A Y
GRK5        *                     W   I *   I W
GRK6                                          L Y
                                              M E
                                              D G
                                              * *

CaMK I    M Q L V S G G E L F D R I V E K G G Y
CaMK IIa  F D I I T A A D I W E D L I A R E Y F
CaMK IIb  W N M L       * M Y * K M L D   D F W
CaMK IIg  Y E V M         V       E V M G   A W
CaMK IId  I *                     *       *   * A
          L
          V

Plk     L E L C R R R S L L E L H K R R K A L F
Plx1    I D I S K K G E M M A I L R A   H S V W
Polo    M * Y   S N K D I N R Y W   N   V V I Y
SNK     V   M   P H A T V A H M I   K   R K P
CDC5        V   H Q   *   I D V M   Q   I T M
Sak         F   E         V K F V   G   L Q
Prk         W   T         Q G W F       M T
Fnk             D         G *   Y           I
Plo1            *                           L
                                            M
                                            R
                                            N
                                            G P78     M E Y A S G G E V F D Y L V A H G R M
MARK1   L D F G T A A K I W E F I I G   A K I
MARK2   I * W         D L Y * W M L         L
Par1    V             R M     V M           V
                      *

CDK2    F E F L H Q D L K K F M D A V A L T G I
CDK4    W D H V D N E I R T Y L E K S P P P A L
CDK6    Y * W I E   * M T R W I * R A G E S   V
            Y M *     V S S   V     G I     I   M
                                    L       M
                                    M       V
                                    T       D
                                            *
```

Figure 2C

```
c-Src     T E F M S K G S L L D F L K G E T G K Y L
c-Yes     M D Y V N H A N I V N Y I R E G S R R A V
Fyn       S * H I C N   T M I E W M D P D K Q D Q
c-Fgr     I   W L A R Q V M Q * V N D E A G K I
Lyn       L       E Q           S R G   S V M
Hck       V       T             T K A   I L N
Lck               Q             Q A *   A F
Csk               D             A *     N W
Matk              G             *       T E
                  *                     L R
                                        M I
                                        V M
                                          G
                                          *

Fak       M E L C T L G E L R S F L Q V R K Y S L
          I D I S S I A D I K T W I N I K R F T I
          L * M   M * M   Y M   L       W   M
          V   V   V   V   V M               V c-Abl     T E F M T Y G N L L D Y L R E C N R Q E V
          S D W I S F A Q I I E F I K D S Q K N D I
          * Y L   W     M M * W M   *       * L
                  V     V V   V                 M

Tie       I E Y A P Y G N L L D F L R K S R V L E T D P A F A R E H G T
Tek       T D F C R H A D I V N Y I H R N K H T F L Q H H S D I A N S P
PDGFR-b   V * W S F F   Q M S T W M K S K   D S D F S N K P E K R R P E
PDGFR-a   L   T K W   E V I E   V   A T   N A W S L C R D K A P K K R
Flt1      M     G W   *   M Q       G Q   I E Y V P Y G E R S L E M S
Flt4      S     Y         T S       T R   L I * I E Q   W G G D Q Q D
Flk1                      *                M M   M N F   Y * L K D F K
                                           E V   W T W   T   M I * T *
                                           Q D   Y I S   *   V M   R
                                           * G     M         T V   I
                                                   V         G     L
                                                   *         *     V
                                                                   N
                                                                   W
                                                                   Y
                                                                   A

Tie       S T L Y S N A L
Tek       A E F G L E P A
PDGFR-b   D I E K M V E G
PDGFR-a   K K R A V G D I
Flt1      R F D F T Q G M
Flt4      G S I W I D * V
Flk1      T D M R   I
          E L V     L
          * M W     M
            V Y     A
            R K     *
            W *
            Y
            *
```

Figure 2D

```
Flg      V E Y A S K G N L R E Y L Q A R R P   P G L E Y C Y N P S H N P
Bek      I D C G A R A Q I K D F I R G K K       A M D L S F D I N R V S
FGFR-3   L * F   T       M   * W M N             P * F T P Q T C K P T
FGFR-4   M   W   G       V     V K               I   W   W E G P     S
             S                                   V   I   * L T     Q
                                                     M     M Q     I
                                                     V     V S     L
                                                             S     M
                                                             A     T

Flg      E Q L
Bek      G P M
FGFR-3   D N I
FGFR-4   A   V
         * c-Met    L P Y M K H G D L R N F I R N E T H N P
c-Sea    I   F I R     A E I L H W L K A Q E R S
Ron      M   W L C     * M K Q Y M   S P Q K Q
         V     V S       V I     V   Q D S   T
                         M           T N D
                         V           G * N
                                         *

EGFR     T Q L M P F G C L L D Y V R E H K D N I
ErbB2    S N Y L   Y A S I I E H I H Q N R G R L
ErbB3        I I   L   T M M * F L K D Q   E A M
ErbB4        M V   H   V V   W M   N       A Q V
             V     W             *         * K
             F     I                         G
             W     M
                   V

Ret      V E Y A K Y G S L R G F L R E S R K V G P G Y L G S G G S R N
         I D F G R F A T I K A W I K D T K R I A   A F I A T A A T K Q
         L * W   W     M     Y M *       L         W M
         M                   V           V         V

Ret      S S L D H P D E R A L
         T T I E     E D K G I
             M *     * *     M
             V               V
```

Figure 2E

```
Syk      M E M A E L G P L N K Y L Q Q N R H V I
Zap70    I D I G G G A   I H R F I V G K K E E L
         L * L   D I       M Q   W M N N Q   D I M
         V   V   A M       V       V I A R   * L V
                 * V                     L     M
                   A                     M     D
                                               *

Jak1     M E F L P S G S L K E Y L P K N K N K I
Jak2     I D Y I   Y A C I R D F I Q R H R E R L
Jak3     L * W M   T   T M   * W M N   Q S A   M
Tyk2     V   V     F   V       V       T Q     V
                   W                     D
                   L                     G
                   I                     I
                                         L
                                         *

Iak1     L E Y A P L G T V Y R E L Q K L S K F
         I D F G   I A S I F K D I N R I T R W
         M * W     M   L W * M   M         Y
         V   V     V   M     V   V

Chk1     L E Y C S G G E L F D R I E P D I G M
         I D F S T A A D I W E K L D   E L A I
         M * W       * M Y * M *   * M   L
         V           V     V     V   V

IKK-1    M E Y C S G G D L R K L L N K P E N C C G L
IKK-2    I D F S Q A A E I K R Y I Q Q F D Q S S A I
         L * W   T       * M   I M   R W *       M
         V       N         V   M V   N Y         V
                                 V
                                 F
                                 W

DAPK     L E L V A G G E L F D F L A E K E S L
         I D I I G A A D I W E W I G D R D T I
         M * M L     * M Y * Y M   *   * M
         V   V M       V     V         V

IRK      M E L M A H G D L K S Y L R S L R P E A E N N P G R P P P T L
         I D I I G   A E I R T F I K T I K   D G D Q Q   A K       S I
         L * M L     * M   W M   M     * *                         M
         V   V V       V     V   V                                 V

TGFbRII  T A F H A K G N L Q E Y L T R H V I
ACTRIIA  S G W   E R A S I S D F I K A N I V
ACTRIIB    Y   D     Q M T * W M S G Q L L
               G     T V       V R K   M M
               *
```

Figure 2F

```
ALK1    T H Y H E H G S L Y D F L Q R Q T L
ALK2    S D F   D M A T I F E Y I K L T S V
ALK3      E W   * N     M W * W M N C A   I
ALK4          *     I     V       V R S Y   M
ALK5                L                 K N
ALK6                V                 I S
                    Q                 M F
                                      V W
                                      T G

Trk-NGFR F E Y M R H G D L N R F L R S H G P D A K L L A G G E D V A P
TrkB     W D F I K   A E I Q K W I K A   A   E G V I M V E A N P P T E
TrkC     Y * W L     * M   Y M T     *   M M I I D   Q E R Q A
             V       V     V   G         R V V L A D * I S D
                                         I       M *   * L N G
                                         L       G       M G *
                                                         K

Trk-NGFR P L L
TrkB     G E I
TrkC     A I M
         M V
         V
         D
         *

DDR1    T D Y M E N G D L N Q F L S A H Q L
DDR2    S E F I D Q A E I Q N W I T R   E P
          * W L *       * M     Y M K   N I
              V           V     V   G   D V
                                        * M

ILK     T H W M P Y G S L Y N V L H E G T N F V V
          S   F I   F A T I F Q I I   D A S Q W I I
          Y L   W     M W   L M     *       Y L L
            M         V     M V             M M
```

Figure 3A

| Peptide | N-terminal | | C-terminal |
|---|---|---|---|
| Akt1/Raca | | | |
| 95 K014D001 | Myristyl - | G M E Y A N G G E L F F H L S R E R V F | - NH2 |
| ALK1 | | | |
| 96 K048D101 | Myristyl - | G T H Y H E H G S L Y D F L Q R Q T L | - NH2 |
| Braf | | | |
| 97 K003D001 | Acetyl - | K K K K K K G G S S L Y H H L H I I E T K F | - NH2 |
| 98 K003D101 | Myristyl - | G T Q W S E G S S L Y H H L H I I E T K F | - NH2 |
| c-Abl | | | |
| 99 K061D101 | Myristyl - | G T E F M T Y G N L L D Y L R E C N R Q E V | - NH2 |
| c-Met | | | |
| 100 K073D101 | Myristyl - | G L P Y M K H G D L R N F I R N E T H N P | - NH2 |
| c-Raf | | | |
| 101 K001D101 | Myristyl - | G T Q W S E G S S L Y K H L H V Q E T K F | - NH2 |
| 102 K001D001 | Acetyl - | S S L Y K H L H V Q E! T K F | - NH2 |
| c-Sea | | | |
| 103 K074D101 | Myristyl - | G L P Y M R H G D L R H F I R A Q E R S P | - NH2 |
| c-Src | | | |
| 104 K051D101 | Myristyl - | G T E Y M S K G S L L D F L K G E T G K Y L | - NH2 |
| 105 K051D001 | Acetyl - | G S L L D! L K G E! T G K F L | - NH2 |
| CDK2 | | | |
| 106 K049D101 | Myristyl - | G F E F L H Q D L K K F M D A S A L T G I | - NH2 |
| 107 K049D001 | Acetyl - | D! L K K F M D! A S A L T G M | - NH2 |
| CDK4 | | | |
| 108 K050D001 | Acetyl - | D! L R T Y L D! K A P P P G L | - NH2 |
| 109 K050D101 | Myristyl - | G F E H V D Q D L R T Y L D K A P P P G L | - NH2 |
| CDK6 | | | |
| 110 K089D101 | Myristyl - | G F E H V D Q D L T T Y L D K V P E P G V | - NH2 |
| Chk1 | | | |
| 111 K088D102 | Myristyl - | G E Y S S G G E L F D R I E P D I G M | - NH2 |
| 112 K088D101 | Myristyl - | G E Y A S G G E L F D R I E P D I G M | - NH2 |
| CK IIa | | | |
| 113 K022D001 | Acetyl - | K K K K K G G N N T D F K Q L Y Q T L | - NH2 |
| 114 K022D101 | Myristyl - | G F E H V N N T D F K Q L Y Q T L | - NH2 |

Figure 3B

Csk
| | | | | |
|---|---|---|---|---|
| 115 K058D101 | Myristyl- | G T E Y M A K G S L V D Y L R S R G R S V L | -NH2 |
| 116 K058D001 | Acetyl- | G S L V D! L R S R G R S V L | -NH2 |

Fak
| 117 K060D101 | Myristyl- | G M E L S T L G E L R S F L Q V R K Y S L | -NH2 |

FGFR-3
| 118 K071D101 | Myristyl- | G G N L R E F L R A R R P P G L E | -NH2 |
| 119 K071D001 | Acetyl- | G N L R E! F L R A R R P P G L E! | -NH2 |
| 120 K071D102 | Myristyl- | G V E Y A A K G N L R E F L R A R R P P G L E | -NH2 |
| 121 K071D901 | Stearyl- | G S F D T S K P P E E Q L | -NH2 |

Flk1
| 122 K068D101 | Myristyl- | G V E F S K F G N L S N F L R A K R N L F V P | -NH2 |
| 123 K068D101 | Myristyl- | G G N L S N F L R A K R N L F V P | -NH2 |
| 124 K068D001 | Acetyl- | G N L S N F L R A K R N L F V P | -NH2 |
| 125 K068D901 | Stearyl- | G R F R Q G K D Y V G E L | -NH2 |

GSK3b
| 126 K018D003 | Acetyl- | K K K K K K G G G V A R H Y S R A K Q T L P | -NH2 |
| 127 K018D002 | Acetyl- | V A R H Y S R A K Q T L P | -NH2 |
| 128 K018D101 | Myristyl- | G D Y V P E T V Y R V A R H Y S R A K Q T L | -NH2 |
| 129 K018D001 | Acetyl- | R V A R H Y S R A K Q T | -NH2 |

Hck
| 130 K056D101 | Myristyl- | G T E F M A K G S L L D F L K S D E G S K Q | -NH2 |

Jak1
| 131 K087D101 | Myristyl- | G L E Y A P L G T V Y R E L Q K L S K F | -NH2 |

IKK-1
| 132 K090D101 | Myristyl- | G M E Y S S G G D L R K L L N K P E N S S G L | -NH2 |

IKK-2
| 133 K091D101 | Myristyl- | G M E Y S Q G G D L R K Y L N Q F E N S S G L | -NH2 |

ILK
| 134 K107D101 | Myristyl- | G T H W M P Y G S L Y N V L H E G T N F V V | -NH2 |
| 135 K107D901 | Stearyl- | G Y N V L H E G T N F V V | -NH2 |

Figure 3C

IRK

| # | ID | | Sequence | |
|---|---|---|---|---|
| 136 | K094D101 | Myristyl- | G M E L M A H G D L K S Y L R S L R P | -NH2 |
| 137 | K094D001 | Acetyl- | A Q N N P G R P P P T L | -NH2 |
| 138 | K094D102 | Myristyl- | G L K S Y L R S L R P E A | -NH2 |
| 139 | K094D103 | Myristyl- | G A E N N P G R P P P T L | -NH2 |
| 140 | K094D104 | Myristyl- | G L R P E A E N N P G R P P P T L | -NH2 |

Jak1

| 141 | K084D101 | Myristyl- | G M E F L P S G S L K E Y L P K N K N K I | -NH2 |
|---|---|---|---|---|
| 142 | K084D102 | Myristyl- | G L K E Y L P K N K N K I | -NH2 |

Jak2

| 143 | K085D102 | Myristyl- | G L R D Y L Q K H K E R I | -NH2 |
|---|---|---|---|---|
| 144 | K085D105 | Stearyl- | G L R D Y L Q K H K E | -NH2 |

Jak3

| 145 | K086D101 | Myristyl- | G M E Y L P S G S L R D F L Q R H R A L | -NH2 |
|---|---|---|---|---|
| 146 | K086D102 | Myristyl- | G M E Y L P S G S L R D F L Q R H R A R L | -NH2 |
| 147 | K086D103 | Myristyl- | G L R D F L Q R H R A R L | -NH2 |

Lck

| 148 | K057D001 | Acetyl- | G S L V D I L K T P S G I K L | -NH2 |
|---|---|---|---|---|
| 149 | K057D101 | Myristyl- | G T E Y M E N G S L V D F L K T P S G I K L | -NH2 |

Lyn

| 150 | K055D101 | Myristyl- | G T E Y M A K G S L L D F L K S D E G G K V | -NH2 |
|---|---|---|---|---|

MARK1

| 151 | K045D101 | Myristyl- | G M E Y A S G G E V F D Y L V A H G R M | -NH2 |
|---|---|---|---|---|

PDGFR-b

| 152 | K064D001 | Acetyl- | G D I L V D I Y L H R N K H T F L | -NH2 |
|---|---|---|---|---|
| 153 | K064D101 | Myristyl- | G T E Y S R Y G D L V D Y L H R N K H T F L | -NH2 |

PKCb

| 154 | K008D101 | Myristyl- | G M E Y V N G G D L M Y H I Q Q V G R F | -NH2 |
|---|---|---|---|---|
| 155 | K008D001 | Acetyl- | K K K K K K G G D L M Y H I Q Q V G R F | -NH2 |

Plk

| 156 | K035D001 | Acetyl- | R S L L E I L H K R R K A | -NH2 |
|---|---|---|---|---|
| 157 | K035D101 | Myristyl- | G R S L L E I L H K R R K A | -NH2 |

Figure 3D

| | | | |
|---|---|---|---|
| 158 K035D102 | Myristyl- | G L E L S R R R S L L E L H K R R K A L | -NH2 |
| Ret | | | |
| 159 K080D101 | Myristyl- | G V E Y A K Y G S L R G F L R E S R K V G P | -NH2 |
| 160 K080D001 | Acetyl- | G S L R G F L R E S R K V G P | -NH2 |
| Ron | | | |
| 161 K075D101 | Myristyl- | G L P Y M C H G D L L Q F I R S P Q R N P | -NH2 |
| SNK | | | |
| 162 K038D101 | Myristyl- | G L E Y S S R R S M A H I L K A R K V L | -NH2 |
| Syk | | | |
| 163 K082D101 | Myristyl- | G M E M A E L G P L N K Y L Q Q N R H V | -NH2 |
| TGFbRII | | | |
| 164 K093D101 | Myristyl- | G T A F H A K G N L Q E Y L T R H V I | -NH2 |
| TrkB | | | |
| 165 K102D101 | Myristyl- | G F E Y M K H G D L N K F L R A H G P D A V L M A | -NH2 |
| 166 K102D106 | Myristyl- | G L R A H G P D A V L M A | -NH2 |
| 167 K102D107 | Myristyl- | G L R A H G P D A V L | -NH2 |
| 168 K102D108 | Myristyl- | G L N F K L R A H G P D A | -NH2 |
| 169 K102D109 | Myristyl- | G F K L R A H G P D A V L | -NH2 |
| Zap70 | | | |
| 170 K083D101 | Myristyl- | G M E M A G G G P L H K F L V G K R E E I | -NH2 |

SEQUENCE LISTING

```
<160> NUMBER OF SEQ ID NOS: 172

<210> SEQ ID NO 1
<211> LENGTH: 20
<212> TYPE: PRT
<213> ORGANISM: unknown
<220> FEATURE:
<223> OTHER INFORMATION: c-Raf

<400> SEQUENCE: 1

Thr Gln Trp Cys Glu Gly Ser Ser Leu Tyr Lys His Leu His Val Gln
 1               5                  10                  15

Glu Thr Lys Phe
            20

<210> SEQ ID NO 2
<211> LENGTH: 20
<212> TYPE: PRT
<213> ORGANISM: unknown
<220> FEATURE:
<223> OTHER INFORMATION: a-Raf

<400> SEQUENCE: 2

Thr Gln Trp Cys Glu Gly Ser Ser Leu Tyr His His Leu His Val Ala
 1               5                  10                  15

Asp Thr Arg Phe
            20

<210> SEQ ID NO 3
<211> LENGTH: 20
<212> TYPE: PRT
<213> ORGANISM: unknown
<220> FEATURE:
<223> OTHER INFORMATION: Braf

<400> SEQUENCE: 3
```

Thr Gln Trp Cys Glu Gly Ser Ser Leu Tyr His His Leu His Ile Ile
1               5                   10                  15

Glu Thr Lys Phe
            20

<210> SEQ ID NO 4
<211> LENGTH: 19
<212> TYPE: PRT
<213> ORGANISM: unknown
<220> FEATURE:
<223> OTHER INFORMATION: c-APKa

<400> SEQUENCE: 4

Met Glu Tyr Val Pro Gly Gly Glu Met Phe Ser His Leu Arg Arg Ile
1               5                   10                  15

Gly Arg Phe

<210> SEQ ID NO 5
<211> LENGTH: 19
<212> TYPE: PRT
<213> ORGANISM: unknown
<220> FEATURE:
<223> OTHER INFORMATION: cAPKg

<400> SEQUENCE: 5

Met Glu Tyr Val Pro Gly Gly Glu Met Phe Ser Arg Leu Gln Arg Val
1               5                   10                  15

Gly Arg Phe

<210> SEQ ID NO 6
<211> LENGTH: 19
<212> TYPE: PRT
<213> ORGANISM: unknown
<220> FEATURE:
<223> OTHER INFORMATION: PKCa

<400> SEQUENCE: 6

Met Glu Tyr Val Asn Gly Gly Asp Leu Met Tyr His Ile Gln Gln Val
1               5                   10                  15

Gly Lys Phe

<210> SEQ ID NO 7
<211> LENGTH: 19
<212> TYPE: PRT
<213> ORGANISM: unknown
<220> FEATURE:
<223> OTHER INFORMATION: PKCb

<400> SEQUENCE: 7

Met Glu Tyr Val Asn Gly Gly Asp Leu Met Tyr His Ile Gln Gln Val
1               5                   10                  15

Gly Arg Phe

<210> SEQ ID NO 8
<211> LENGTH: 19
<212> TYPE: PRT
<213> ORGANISM: unknown
<220> FEATURE:
<223> OTHER INFORMATION: PKCg

<400> SEQUENCE: 8

Met Glu Tyr Val Thr Gly Gly Asp Leu Met Tyr His Ile Gln Gln Leu
1               5                   10                  15

Gly Lys Phe

<210> SEQ ID NO 9
<211> LENGTH: 19
<212> TYPE: PRT
<213> ORGANISM: unknown
<220> FEATURE:
<223> OTHER INFORMATION: PKCd

<400> SEQUENCE: 9

Met Glu Phe Leu Asn Gly Gly Asp Leu Met Phe His Ile Gln Asp Lys
 1               5                  10                  15

Gly Arg Phe

<210> SEQ ID NO 10
<211> LENGTH: 19
<212> TYPE: PRT
<213> ORGANISM: unknown
<220> FEATURE:
<223> OTHER INFORMATION: PKCe

<400> SEQUENCE: 10

Met Glu Tyr Val Asn Gly Gly Asp Leu Met Phe Gln Ile Gln Arg Ser
 1               5                  10                  15

Arg Lys Phe

<210> SEQ ID NO 11
<211> LENGTH: 19
<212> TYPE: PRT
<213> ORGANISM: unknown
<220> FEATURE:
<223> OTHER INFORMATION: PKCet

<400> SEQUENCE: 11

Met Glu Phe Val Asn Gly Gly Asp Leu Met Phe His Ile Gln Lys Ser
 1               5                  10                  15

Arg Arg Phe

<210> SEQ ID NO 12
<211> LENGTH: 19
<212> TYPE: PRT
<213> ORGANISM: unknown
<220> FEATURE:
<223> OTHER INFORMATION: PKCth

<400> SEQUENCE: 12

Met Glu Tyr Leu Asn Gly Gly Asp Leu Met Tyr His Ile Gln Ser Cys
 1               5                  10                  15

His Lys Phe

<210> SEQ ID NO 13
<211> LENGTH: 19
<212> TYPE: PRT
<213> ORGANISM: unknown
<220> FEATURE:
<223> OTHER INFORMATION: Akt1/Raca

<400> SEQUENCE: 13

Met Glu Tyr Ala Asn Gly Gly Glu Leu Phe Phe His Leu Ser Arg Glu
 1               5                  10                  15

Arg Val Phe

-continued

```
<210> SEQ ID NO 14
<211> LENGTH: 22
<212> TYPE: PRT
<213> ORGANISM: unknown
<220> FEATURE:
<223> OTHER INFORMATION: GSK3a

<400> SEQUENCE: 14

Leu Glu Tyr Val Pro Glu Thr Val Tyr Arg Val Ala Arg His Phe Thr
 1               5                  10                  15

Lys Ala Lys Leu Ile Ile
            20

<210> SEQ ID NO 15
<211> LENGTH: 22
<212> TYPE: PRT
<213> ORGANISM: unknown
<220> FEATURE:
<223> OTHER INFORMATION: GSK3b

<400> SEQUENCE: 15

Leu Asp Tyr Val Pro Glu Thr Val Tyr Arg Val Ala Arg His Tyr Ser
 1               5                  10                  15

Arg Ala Lys Gln Thr Leu
            20

<210> SEQ ID NO 16
<211> LENGTH: 16
<212> TYPE: PRT
<213> ORGANISM: unknown
<220> FEATURE:
<223> OTHER INFORMATION: CK IIa

<400> SEQUENCE: 16

Phe Glu His Val Asn Asn Thr Asp Phe Lys Gln Leu Tyr Gln Thr Leu
 1               5                  10                  15

<210> SEQ ID NO 17
<211> LENGTH: 16
<212> TYPE: PRT
<213> ORGANISM: unknown
<220> FEATURE:
<223> OTHER INFORMATION: CK IIa'

<400> SEQUENCE: 17

Phe Glu Tyr Ile Asn Asn Thr Asp Phe Lys Gln Leu Tyr Gln Ile Leu
 1               5                  10                  15

<210> SEQ ID NO 18
<211> LENGTH: 19
<212> TYPE: PRT
<213> ORGANISM: unknown
<220> FEATURE:
<223> OTHER INFORMATION: bARK1

<400> SEQUENCE: 18

Leu Asp Leu Met Asn Gly Gly Asp Leu His Tyr His Leu Ser Gln His
 1               5                  10                  15

Gly Val Phe

<210> SEQ ID NO 19
<211> LENGTH: 23
<212> TYPE: PRT
<213> ORGANISM: unknown
<220> FEATURE:
<223> OTHER INFORMATION: GRK1
```

```
<400> SEQUENCE: 19

Met Thr Ile Met Asn Gly Gly Asp Ile Arg Tyr His Ile Tyr Asn Val
1               5                   10                  15

Asp Glu Asp Asn Pro Gly Phe
            20

<210> SEQ ID NO 20
<211> LENGTH: 21
<212> TYPE: PRT
<213> ORGANISM: unknown
<220> FEATURE:
<223> OTHER INFORMATION: GRK4

<400> SEQUENCE: 20

Leu Thr Ile Met Asn Gly Gly Asp Leu Lys Phe His Ile Tyr Asn Leu
1               5                   10                  15

Gly Asn Pro Gly Phe
            20

<210> SEQ ID NO 21
<211> LENGTH: 21
<212> TYPE: PRT
<213> ORGANISM: unknown
<220> FEATURE:
<223> OTHER INFORMATION: GRK5

<400> SEQUENCE: 21

Leu Thr Ile Met Asn Gly Gly Asp Leu Lys Phe His Ile Tyr Asn Met
1               5                   10                  15

Gly Asn Pro Gly Phe
            20

<210> SEQ ID NO 22
<211> LENGTH: 21
<212> TYPE: PRT
<213> ORGANISM: unknown
<220> FEATURE:
<223> OTHER INFORMATION: GRK6

<400> SEQUENCE: 22

Leu Thr Leu Met Asn Gly Gly Asp Leu Lys Phe His Ile Tyr His Met
1               5                   10                  15

Gly Gln Ala Gly Phe
            20

<210> SEQ ID NO 23
<211> LENGTH: 19
<212> TYPE: PRT
<213> ORGANISM: unknown
<220> FEATURE:
<223> OTHER INFORMATION: CaMKI

<400> SEQUENCE: 23

Met Gln Leu Val Ser Gly Gly Glu Leu Phe Asp Arg Ile Val Glu Lys
1               5                   10                  15

Gly Gly Tyr

<210> SEQ ID NO 24
<211> LENGTH: 19
<212> TYPE: PRT
<213> ORGANISM: unknown
<220> FEATURE:
<223> OTHER INFORMATION: CaMK IIa
```

```
<400> SEQUENCE: 24

Phe Asp Leu Val Thr Gly Gly Glu Leu Phe Glu Asp Ile Val Ala Arg
 1               5                  10                  15

Glu Tyr Tyr

<210> SEQ ID NO 25
<211> LENGTH: 19
<212> TYPE: PRT
<213> ORGANISM: unknown
<220> FEATURE:
<223> OTHER INFORMATION: Plk

<400> SEQUENCE: 25

Leu Glu Leu Cys Arg Arg Arg Ser Leu Leu Glu Leu His Lys Arg Arg
 1               5                  10                  15

Lys Ala Leu

<210> SEQ ID NO 26
<211> LENGTH: 19
<212> TYPE: PRT
<213> ORGANISM: unknown
<220> FEATURE:
<223> OTHER INFORMATION: Plx1

<400> SEQUENCE: 26

Leu Glu Leu Cys Arg Arg Arg Ser Leu Leu Glu Leu His Lys Arg Arg
 1               5                  10                  15

Lys Ala Val

<210> SEQ ID NO 27
<211> LENGTH: 19
<212> TYPE: PRT
<213> ORGANISM: unknown
<220> FEATURE:
<223> OTHER INFORMATION: POLO

<400> SEQUENCE: 27

Leu Glu Leu Cys Lys Lys Arg Ser Met Met Glu Leu His Lys Arg Arg
 1               5                  10                  15

Lys Ser Ile

<210> SEQ ID NO 28
<211> LENGTH: 19
<212> TYPE: PRT
<213> ORGANISM: unknown
<220> FEATURE:
<223> OTHER INFORMATION: SNK

<400> SEQUENCE: 28

Leu Glu Tyr Cys Ser Arg Arg Ser Met Ala His Ile Leu Lys Ala Arg
 1               5                  10                  15

Lys Val Leu

<210> SEQ ID NO 29
<211> LENGTH: 19
<212> TYPE: PRT
<213> ORGANISM: unknown
<220> FEATURE:
<223> OTHER INFORMATION: CDC 5

<400> SEQUENCE: 29

Leu Glu Ile Cys Pro Asn Gly Ser Leu Met Glu Leu Leu Lys Arg Arg
```

```
                  1               5              10              15

Lys Val Leu

<210> SEQ ID NO 30
<211> LENGTH: 20
<212> TYPE: PRT
<213> ORGANISM: unknown
<220> FEATURE:
<223> OTHER INFORMATION: Sak

<400> SEQUENCE: 30

Leu Glu Met Cys His Asn Gly Glu Met Asn Arg Tyr Leu Lys Asn Arg
  1               5              10              15

Val Lys Pro Phe
             20

<210> SEQ ID NO 31
<211> LENGTH: 19
<212> TYPE: PRT
<213> ORGANISM: unknown
<220> FEATURE:
<223> OTHER INFORMATION: Prk

<400> SEQUENCE: 31

Leu Glu Leu Cys Ser Arg Lys Ser Leu Ala His Ile Trp Lys Ala Arg
  1               5              10              15

His Thr Leu

<210> SEQ ID NO 32
<211> LENGTH: 19
<212> TYPE: PRT
<213> ORGANISM: unknown
<220> FEATURE:
<223> OTHER INFORMATION: Plo1

<400> SEQUENCE: 32

Leu Glu Leu Cys Glu His Lys Ser Leu Met Glu Leu Leu Arg Lys Arg
  1               5              10              15

Lys Gln Leu

<210> SEQ ID NO 33
<211> LENGTH: 19
<212> TYPE: PRT
<213> ORGANISM: unknown
<220> FEATURE:
<223> OTHER INFORMATION: MARK1

<400> SEQUENCE: 33

Met Glu Tyr Ala Ser Gly Gly Glu Val Phe Asp Tyr Leu Val Ala His
  1               5              10              15

Gly Arg Met

<210> SEQ ID NO 34
<211> LENGTH: 19
<212> TYPE: PRT
<213> ORGANISM: unknown
<220> FEATURE:
<223> OTHER INFORMATION: P78

<400> SEQUENCE: 34

Met Glu Tyr Ala Ser Gly Gly Glu Val Phe Asp Tyr Leu Val Ala His
  1               5              10              15

Gly Arg Met
```

```
<210> SEQ ID NO 35
<211> LENGTH: 20
<212> TYPE: PRT
<213> ORGANISM: unknown
<220> FEATURE:
<223> OTHER INFORMATION: CDK2

<400> SEQUENCE: 35

Phe Glu Phe Leu His Gln Asp Leu Lys Lys Phe Met Asp Ala Ser Ala
 1               5                  10                  15

Leu Thr Gly Ile
            20

<210> SEQ ID NO 36
<211> LENGTH: 20
<212> TYPE: PRT
<213> ORGANISM: unknown
<220> FEATURE:
<223> OTHER INFORMATION: CDK4

<400> SEQUENCE: 36

Phe Glu His Val Asp Gln Asp Leu Arg Thr Tyr Leu Asp Lys Ala Pro
 1               5                  10                  15

Pro Pro Gly Leu
            20

<210> SEQ ID NO 37
<211> LENGTH: 20
<212> TYPE: PRT
<213> ORGANISM: Unknown
<220> FEATURE:
<223> OTHER INFORMATION: CDK6

<400> SEQUENCE: 37

Phe Glu His Val Asp Gln Asp Leu Thr Thr Tyr Leu Asp Lys Val Pro
 1               5                  10                  15

Glu Pro Gly Val
            20

<210> SEQ ID NO 38
<211> LENGTH: 21
<212> TYPE: PRT
<213> ORGANISM: unknown
<220> FEATURE:
<223> OTHER INFORMATION: c-Src

<400> SEQUENCE: 38

Thr Glu Tyr Met Ser Lys Gly Ser Leu Leu Asp Phe Leu Lys Gly Glu
 1               5                  10                  15

Thr Gly Lys Tyr Leu
            20

<210> SEQ ID NO 39
<211> LENGTH: 21
<212> TYPE: PRT
<213> ORGANISM: unknown
<220> FEATURE:
<223> OTHER INFORMATION: c-Yes

<400> SEQUENCE: 39

Thr Glu Phe Met Ser Lys Gly Ser Leu Leu Asp Phe Leu Lys Glu Gly
 1               5                  10                  15

Asp Gly Lys Tyr Leu
```

```
                20

<210> SEQ ID NO 40
<211> LENGTH: 21
<212> TYPE: PRT
<213> ORGANISM: unknown
<220> FEATURE:
<223> OTHER INFORMATION: Fyn

<400> SEQUENCE: 40

Thr Glu Tyr Met Asn Lys Gly Ser Leu Leu Asp Phe Leu Lys Asp Gly
 1               5                  10                  15

Glu Gly Arg Ala Leu
            20

<210> SEQ ID NO 41
<211> LENGTH: 21
<212> TYPE: PRT
<213> ORGANISM: unknown
<220> FEATURE:
<223> OTHER INFORMATION: c-Fgr

<400> SEQUENCE: 41

Thr Glu Phe Met Cys His Gly Ser Leu Leu Asp Phe Leu Lys Asn Pro
 1               5                  10                  15

Glu Gly Gln Asp Leu
            20

<210> SEQ ID NO 42
<211> LENGTH: 21
<212> TYPE: PRT
<213> ORGANISM: unknown
<220> FEATURE:
<223> OTHER INFORMATION: Lyn

<400> SEQUENCE: 42

Thr Glu Tyr Met Ala Lys Gly Ser Leu Leu Asp Phe Leu Lys Ser Asp
 1               5                  10                  15

Glu Gly Gly Lys Val
            20

<210> SEQ ID NO 43
<211> LENGTH: 21
<212> TYPE: PRT
<213> ORGANISM: unknown
<220> FEATURE:
<223> OTHER INFORMATION: Hck

<400> SEQUENCE: 43

Thr Glu Phe Met Ala Lys Gly Ser Leu Leu Asp Phe Leu Lys Ser Asp
 1               5                  10                  15

Glu Gly Ser Lys Gln
            20

<210> SEQ ID NO 44
<211> LENGTH: 21
<212> TYPE: PRT
<213> ORGANISM: unknown
<220> FEATURE:
<223> OTHER INFORMATION: Lck

<400> SEQUENCE: 44

Thr Glu Tyr Met Glu Asn Gly Ser Leu Val Asp Phe Leu Lys Thr Pro
 1               5                  10                  15
```

Ser Gly Ile Lys Leu
            20

<210> SEQ ID NO 45
<211> LENGTH: 21
<212> TYPE: PRT
<213> ORGANISM: unknown
<220> FEATURE:
<223> OTHER INFORMATION: Csk

<400> SEQUENCE: 45

Thr Glu Tyr Met Ala Lys Gly Ser Leu Val Asp Tyr Leu Arg Ser Arg
 1               5                  10                  15

Gly Arg Ser Val Leu
            20

<210> SEQ ID NO 46
<211> LENGTH: 21
<212> TYPE: PRT
<213> ORGANISM: unknown
<220> FEATURE:
<223> OTHER INFORMATION: MatK

<400> SEQUENCE: 46

Met Glu His Val Ser Lys Gly Asn Leu Val Asn Phe Leu Arg Thr Arg
 1               5                  10                  15

Gly Arg Ala Leu Val
            20

<210> SEQ ID NO 47
<211> LENGTH: 20
<212> TYPE: PRT
<213> ORGANISM: unknown
<220> FEATURE:
<223> OTHER INFORMATION: Fak

<400> SEQUENCE: 47

Met Glu Leu Cys Thr Leu Gly Glu Leu Arg Ser Phe Leu Gln Val Arg
 1               5                  10                  15

Lys Tyr Ser Leu
            20

<210> SEQ ID NO 48
<211> LENGTH: 21
<212> TYPE: PRT
<213> ORGANISM: unknown
<220> FEATURE:
<223> OTHER INFORMATION: c-Abl

<400> SEQUENCE: 48

Thr Glu Phe Met Thr Tyr Gly Asn Leu Leu Asp Tyr Leu Arg Glu Cys
 1               5                  10                  15

Asn Arg Gln Glu Val
            20

<210> SEQ ID NO 49
<211> LENGTH: 35
<212> TYPE: PRT
<213> ORGANISM: unknown
<220> FEATURE:
<223> OTHER INFORMATION: Tie

<400> SEQUENCE: 49

Ile Glu Tyr Ala Pro Tyr Gly Asn Leu Leu Asp Phe Leu Arg Lys Ser
 1               5                  10                  15

Arg Val Leu Glu Thr Asp Pro Ala Phe Ala Arg Glu His Gly Thr Ala
            20                  25                  30

Ser Thr Leu
        35

<210> SEQ ID NO 50
<211> LENGTH: 35
<212> TYPE: PRT
<213> ORGANISM: unknown
<220> FEATURE:
<223> OTHER INFORMATION: Tek

<400> SEQUENCE: 50

Ile Glu Tyr Ala Pro His Gly Asn Leu Leu Asp Phe Leu Arg Lys Ser
 1               5                  10                  15

Arg Val Leu Glu Thr Asp Pro Ala Phe Ala Ile Ala Asn Ser Thr Ala
            20                  25                  30

Ser Thr Leu
        35

<210> SEQ ID NO 51
<211> LENGTH: 35
<212> TYPE: PRT
<213> ORGANISM: unknown
<220> FEATURE:
<223> OTHER INFORMATION: Flg

<400> SEQUENCE: 51

Val Glu Tyr Ala Ser Lys Gly Asn Leu Arg Glu Tyr Leu Gln Ala Arg
 1               5                  10                  15

Arg Pro Pro Gly Leu Glu Tyr Cys Tyr Asn Pro Ser His Asn Pro Glu
            20                  25                  30

Glu Gln Leu
        35

<210> SEQ ID NO 52
<211> LENGTH: 35
<212> TYPE: PRT
<213> ORGANISM: unknown
<220> FEATURE:
<223> OTHER INFORMATION: Bek

<400> SEQUENCE: 52

Val Glu Tyr Ala Ser Lys Gly Asn Leu Arg Glu Tyr Leu Arg Ala Arg
 1               5                  10                  15

Arg Pro Pro Gly Met Glu Tyr Ser Tyr Asp Ile Asn Arg Val Pro Glu
            20                  25                  30

Glu Gln Met
        35

<210> SEQ ID NO 53
<211> LENGTH: 35
<212> TYPE: PRT
<213> ORGANISM: unknown
<220> FEATURE:
<223> OTHER INFORMATION: FGFR-3

<400> SEQUENCE: 53

Val Glu Tyr Ala Ala Lys Gly Asn Leu Arg Glu Phe Leu Arg Ala Arg
 1               5                  10                  15

Arg Pro Pro Gly Leu Asp Tyr Ser Phe Asp Thr Cys Lys Pro Pro Glu
            20                  25                  30

Glu Gln Leu
        35

<210> SEQ ID NO 54
<211> LENGTH: 35
<212> TYPE: PRT
<213> ORGANISM: unknown
<220> FEATURE:
<223> OTHER INFORMATION: FGFR-4

<400> SEQUENCE: 54

Val Glu Cys Ala Ala Lys Gly Asn Leu Arg Glu Phe Leu Arg Ala Arg
1               5                   10                  15

Arg Pro Pro Gly Pro Asp Leu Ser Pro Asp Gly Pro Arg Ser Ser Glu
            20                  25                  30

Gly Pro Leu
        35

<210> SEQ ID NO 55
<211> LENGTH: 40
<212> TYPE: PRT
<213> ORGANISM: unknown
<220> FEATURE:
<223> OTHER INFORMATION: PDGFR-a

<400> SEQUENCE: 55

Thr Glu Tyr Cys Phe Tyr Gly Asp Leu Val Asn Tyr Leu His Lys Asn
1               5                   10                  15

Arg Asp Ser Phe Leu Ser His His Pro Glu Lys Pro Lys Lys Glu Leu
            20                  25                  30

Asp Ile Phe Gly Leu Asn Pro Ala
        35                  40

<210> SEQ ID NO 56
<211> LENGTH: 40
<212> TYPE: PRT
<213> ORGANISM: unknown
<220> FEATURE:
<223> OTHER INFORMATION: PDGFR-b

<400> SEQUENCE: 56

Thr Glu Tyr Cys Arg Tyr Gly Asp Leu Val Asp Tyr Leu His Arg Asn
1               5                   10                  15

Lys His Thr Phe Leu Gln His His Ser Asp Lys Arg Arg Pro Pro Ser
            20                  25                  30

Ala Glu Leu Tyr Ser Asn Ala Leu
        35                  40

<210> SEQ ID NO 57
<211> LENGTH: 40
<212> TYPE: PRT
<213> ORGANISM: unknown
<220> FEATURE:
<223> OTHER INFORMATION: Flt-1

<400> SEQUENCE: 57

Val Glu Tyr Cys Lys Tyr Gly Asn Leu Ser Asn Tyr Leu Lys Ser Lys
1               5                   10                  15

Arg Asp Leu Phe Phe Leu Asn Lys Asp Ala Ala Leu His Met Glu Pro
            20                  25                  30

Lys Lys Glu Lys Met Glu Pro Gly
        35                  40

<210> SEQ ID NO 58
<211> LENGTH: 40
<212> TYPE: PRT
<213> ORGANISM: unknown
<220> FEATURE:
<223> OTHER INFORMATION: Flt4

<400> SEQUENCE: 58

Val Glu Phe Cys Lys Tyr Gly Asn Leu Ser Asn Phe Leu Arg Ala Lys
 1               5                  10                  15

Arg Asp Ala Phe Ser Pro Cys Ala Glu Lys Ser Pro Glu Gln Arg Gly
            20                  25                  30

Arg Phe Arg Ala Met Val Glu Leu
        35                  40

<210> SEQ ID NO 59
<211> LENGTH: 40
<212> TYPE: PRT
<213> ORGANISM: unknown
<220> FEATURE:
<223> OTHER INFORMATION: Flk1

<400> SEQUENCE: 59

Val Glu Phe Ser Lys Phe Gly Asn Leu Ser Thr Tyr Leu Arg Gly Lys
 1               5                  10                  15

Arg Asn Glu Phe Val Pro Tyr Lys Ser Lys Gly Ala Arg Phe Arg Gln
            20                  25                  30

Gly Lys Asp Tyr Val Gly Glu Leu
        35                  40

<210> SEQ ID NO 60
<211> LENGTH: 20
<212> TYPE: PRT
<213> ORGANISM: unknown
<220> FEATURE:
<223> OTHER INFORMATION: c-Met

<400> SEQUENCE: 60

Leu Pro Tyr Met Lys His Gly Asp Leu Arg Asn Phe Ile Arg Asn Glu
 1               5                  10                  15

Thr His Asn Pro
            20

<210> SEQ ID NO 61
<211> LENGTH: 20
<212> TYPE: PRT
<213> ORGANISM: unknown
<220> FEATURE:
<223> OTHER INFORMATION: c-Sea

<400> SEQUENCE: 61

Leu Pro Tyr Met Arg His Gly Asp Leu Arg His Phe Ile Arg Ala Gln
 1               5                  10                  15

Glu Arg Ser Pro
            20

<210> SEQ ID NO 62
<211> LENGTH: 20
<212> TYPE: PRT
<213> ORGANISM: unknown
<220> FEATURE:
<223> OTHER INFORMATION: Ron -continued

```
<400> SEQUENCE: 62

Leu Pro Tyr Met Cys His Gly Asp Leu Leu Gln Phe Ile Arg Ser Pro
 1               5                  10                  15

Gln Arg Asn Pro
            20

<210> SEQ ID NO 63
<211> LENGTH: 20
<212> TYPE: PRT
<213> ORGANISM: unknown
<220> FEATURE:
<223> OTHER INFORMATION: EGFR

<400> SEQUENCE: 63

Thr Gln Leu Met Pro Phe Gly Cys Leu Leu Asp Tyr Val Arg Glu His
 1               5                  10                  15

Lys Asp Asn Ile
            20

<210> SEQ ID NO 64
<211> LENGTH: 20
<212> TYPE: PRT
<213> ORGANISM: unknown
<220> FEATURE:
<223> OTHER INFORMATION: ErbB2

<400> SEQUENCE: 64

Thr Gln Leu Met Pro Tyr Gly Cys Leu Leu Asp His Val Arg Glu Asn
 1               5                  10                  15

Arg Gly Arg Leu
            20

<210> SEQ ID NO 65
<211> LENGTH: 20
<212> TYPE: PRT
<213> ORGANISM: unknown
<220> FEATURE:
<223> OTHER INFORMATION: ErbB3

<400> SEQUENCE: 65

Thr Gln Tyr Leu Pro Leu Gly Ser Leu Leu Asp His Val Arg Gln His
 1               5                  10                  15

Arg Gly Ala Leu
            20

<210> SEQ ID NO 66
<211> LENGTH: 20
<212> TYPE: PRT
<213> ORGANISM: unknown
<220> FEATURE:
<223> OTHER INFORMATION: ErbB4

<400> SEQUENCE: 66

Thr Gln Leu Met Pro His Gly Cys Leu Leu Glu Tyr Val His Glu His
 1               5                  10                  15

Lys Asp Asn Ile
            20

<210> SEQ ID NO 67
<211> LENGTH: 43
<212> TYPE: PRT
<213> ORGANISM: unknown
<220> FEATURE:
<223> OTHER INFORMATION: Ret
```

```
<400> SEQUENCE: 67

Val Glu Tyr Ala Lys Tyr Gly Ser Leu Arg Gly Phe Leu Arg Glu Ser
 1               5                  10                  15

Arg Lys Val Gly Pro Gly Tyr Leu Gly Ser Gly Gly Ser Arg Asn Ser
            20                  25                  30

Ser Ser Leu Asp His Pro Asp Glu Arg Ala Leu
        35                  40

<210> SEQ ID NO 68
<211> LENGTH: 34
<212> TYPE: PRT
<213> ORGANISM: unknown
<220> FEATURE:
<223> OTHER INFORMATION: TRK-NGFR

<400> SEQUENCE: 68

Phe Glu Tyr Met Arg His Gly Asp Leu Asn Arg Phe Leu Arg Ser His
 1               5                  10                  15

Gly Pro Asp Ala Lys Leu Leu Ala Gly Gly Glu Asp Val Ala Pro Gly
            20                  25                  30

Pro Leu

<210> SEQ ID NO 69
<211> LENGTH: 32
<212> TYPE: PRT
<213> ORGANISM: unknown
<220> FEATURE:
<223> OTHER INFORMATION: TrkB

<400> SEQUENCE: 69

Phe Glu Tyr Met Lys His Gly Asp Leu Asn Lys Phe Leu Arg Ala His
 1               5                  10                  15

Gly Pro Asp Ala Val Leu Met Ala Glu Gly Asn Pro Pro Thr Glu Leu
            20                  25                  30

<210> SEQ ID NO 70
<211> LENGTH: 35
<212> TYPE: PRT
<213> ORGANISM: unknown
<220> FEATURE:
<223> OTHER INFORMATION: TrkC

<400> SEQUENCE: 70

Phe Glu Tyr Met Lys His Gly Asp Leu Asn Lys Phe Leu Arg Ala His
 1               5                  10                  15

Gly Pro Asp Ala Met Ile Leu Val Asp Gly Gln Pro Arg Gln Ala Lys
            20                  25                  30

Gly Glu Leu
        35

<210> SEQ ID NO 71
<211> LENGTH: 19
<212> TYPE: PRT
<213> ORGANISM: unknown
<220> FEATURE:
<223> OTHER INFORMATION: Syk

<400> SEQUENCE: 71

Met Glu Met Ala Glu Leu Gly Pro Leu Asn Lys Tyr Leu Gln Gln Asn
 1               5                  10                  15

Arg His Val
```

```
<210> SEQ ID NO 72
<211> LENGTH: 20
<212> TYPE: PRT
<213> ORGANISM: unknown
<220> FEATURE:
<223> OTHER INFORMATION: Zap70

<400> SEQUENCE: 72

Met Glu Met Ala Gly Gly Gly Pro Leu His Lys Phe Leu Val Gly Lys
 1               5                  10                  15

Arg Glu Glu Ile
            20

<210> SEQ ID NO 73
<211> LENGTH: 20
<212> TYPE: PRT
<213> ORGANISM: unknown
<220> FEATURE:
<223> OTHER INFORMATION: Jak1

<400> SEQUENCE: 73

Met Glu Phe Leu Pro Ser Gly Ser Leu Lys Glu Tyr Leu Pro Lys Asn
 1               5                  10                  15

Lys Asn Lys Ile
            20

<210> SEQ ID NO 74
<211> LENGTH: 20
<212> TYPE: PRT
<213> ORGANISM: unknown
<220> FEATURE:
<223> OTHER INFORMATION: Jak2

<400> SEQUENCE: 74

Met Glu Tyr Leu Pro Tyr Gly Ser Leu Arg Asp Tyr Leu Gln Lys His
 1               5                  10                  15

Lys Glu Arg Ile
            20

<210> SEQ ID NO 75
<211> LENGTH: 20
<212> TYPE: PRT
<213> ORGANISM: unknown
<220> FEATURE:
<223> OTHER INFORMATION: Jak3

<400> SEQUENCE: 75

Met Glu Tyr Leu Pro Ser Gly Cys Leu Arg Asp Phe Leu Gln Arg His
 1               5                  10                  15

Arg Ala Arg Leu
            20

<210> SEQ ID NO 76
<211> LENGTH: 18
<212> TYPE: PRT
<213> ORGANISM: unknown
<220> FEATURE:
<223> OTHER INFORMATION: Tyk2

<400> SEQUENCE: 76

Met Glu Tyr Val Pro Leu Gly Ser Leu Arg Asp Tyr Leu Pro Arg His
 1               5                  10                  15

Ser Ile
```

```
<210> SEQ ID NO 77
<211> LENGTH: 19
<212> TYPE: PRT
<213> ORGANISM: unknown
<220> FEATURE:
<223> OTHER INFORMATION: Iak1

<400> SEQUENCE: 77

Leu Glu Tyr Ala Pro Leu Gly Thr Val Tyr Arg Glu Leu Gln Lys Leu
 1               5                  10                  15

Ser Lys Phe

<210> SEQ ID NO 78
<211> LENGTH: 19
<212> TYPE: PRT
<213> ORGANISM: unknown
<220> FEATURE:
<223> OTHER INFORMATION: Chk1

<400> SEQUENCE: 78

Leu Glu Tyr Cys Ser Gly Gly Glu Leu Phe Asp Arg Ile Glu Pro Asp
 1               5                  10                  15

Ile Gly Met

<210> SEQ ID NO 79
<211> LENGTH: 22
<212> TYPE: PRT
<213> ORGANISM: unknown
<220> FEATURE:
<223> OTHER INFORMATION: IKK-1

<400> SEQUENCE: 79

Met Glu Tyr Cys Ser Gly Gly Asp Leu Arg Lys Leu Leu Asn Lys Pro
 1               5                  10                  15

Glu Asn Cys Cys Gly Leu
                20

<210> SEQ ID NO 80
<211> LENGTH: 22
<212> TYPE: PRT
<213> ORGANISM: unknown
<220> FEATURE:
<223> OTHER INFORMATION: IKK-2

<400> SEQUENCE: 80

Met Glu Tyr Cys Gln Gly Gly Asp Leu Arg Lys Tyr Leu Asn Gln Phe
 1               5                  10                  15

Glu Asn Cys Cys Gly Leu
                20

<210> SEQ ID NO 81
<211> LENGTH: 19
<212> TYPE: PRT
<213> ORGANISM: unknown
<220> FEATURE:
<223> OTHER INFORMATION: DAPK

<400> SEQUENCE: 81

Leu Glu Leu Val Ala Gly Gly Glu Leu Phe Asp Phe Leu Ala Glu Lys
 1               5                  10                  15

Glu Ser Leu
```

```
<210> SEQ ID NO 82
<211> LENGTH: 31
<212> TYPE: PRT
<213> ORGANISM: unknown
<220> FEATURE:
<223> OTHER INFORMATION: IRK

<400> SEQUENCE: 82

Met Glu Leu Met Ala His Gly Asp Leu Lys Ser Tyr Leu Arg Ser Leu
 1               5                  10                  15

Arg Pro Glu Ala Glu Asn Asn Pro Gly Arg Pro Pro Pro Thr Leu
            20                  25                  30

<210> SEQ ID NO 83
<211> LENGTH: 18
<212> TYPE: PRT
<213> ORGANISM: unknown
<220> FEATURE:
<223> OTHER INFORMATION: TGFbRII

<400> SEQUENCE: 83

Thr Ala Phe His Ala Lys Gly Asn Leu Gln Glu Tyr Leu Thr Arg His
 1               5                  10                  15

Val Ile

<210> SEQ ID NO 84
<211> LENGTH: 18
<212> TYPE: PRT
<213> ORGANISM: unknown
<220> FEATURE:
<223> OTHER INFORMATION: ACTRIIA

<400> SEQUENCE: 84

Thr Ala Phe His Glu Lys Gly Ser Leu Ser Asp Phe Leu Lys Ala Asn
 1               5                  10                  15

Val Val

<210> SEQ ID NO 85
<211> LENGTH: 18
<212> TYPE: PRT
<213> ORGANISM: unknown
<220> FEATURE:
<223> OTHER INFORMATION: ACTRIIB

<400> SEQUENCE: 85

Thr Ala Phe His Asp Lys Gly Ser Leu Thr Asp Tyr Leu Lys Gly Asn
 1               5                  10                  15

Ile Ile

<210> SEQ ID NO 86
<211> LENGTH: 18
<212> TYPE: PRT
<213> ORGANISM: unknown
<220> FEATURE:
<223> OTHER INFORMATION: ALK1

<400> SEQUENCE: 86

Thr His Tyr His Glu His Gly Ser Leu Tyr Asp Phe Leu Gln Arg Gln
 1               5                  10                  15

Thr Leu

<210> SEQ ID NO 87
<211> LENGTH: 18
<212> TYPE: PRT
```

```
<213> ORGANISM: unknown
<220> FEATURE:
<223> OTHER INFORMATION: ALK2

<400> SEQUENCE: 87

Thr His Tyr His Glu Met Gly Ser Leu Tyr Asp Tyr Leu Gln Leu Thr
 1               5                  10                  15

Thr Leu

<210> SEQ ID NO 88
<211> LENGTH: 18
<212> TYPE: PRT
<213> ORGANISM: unknown
<220> FEATURE:
<223> OTHER INFORMATION: ALK3

<400> SEQUENCE: 88

Thr Asp Tyr His Glu Asn Gly Ser Leu Tyr Asp Phe Leu Lys Cys Ala
 1               5                  10                  15

Thr Leu

<210> SEQ ID NO 89
<211> LENGTH: 18
<212> TYPE: PRT
<213> ORGANISM: unknown
<220> FEATURE:
<223> OTHER INFORMATION: ALK4

<400> SEQUENCE: 89

Ser Asp Tyr His Glu His Gly Ser Leu Phe Asp Tyr Leu Asn Arg Tyr
 1               5                  10                  15

Thr Val

<210> SEQ ID NO 90
<211> LENGTH: 18
<212> TYPE: PRT
<213> ORGANISM: unknown
<220> FEATURE:
<223> OTHER INFORMATION: alk6

<400> SEQUENCE: 90

Thr Asp Tyr His Glu Asn Gly Ser Leu Tyr Asp Tyr Leu Lys Ser Thr
 1               5                  10                  15

Thr Leu

<210> SEQ ID NO 91
<211> LENGTH: 18
<212> TYPE: PRT
<213> ORGANISM: unknown
<220> FEATURE:
<223> OTHER INFORMATION: DDR1

<400> SEQUENCE: 91

Thr Asp Tyr Met Glu Asn Gly Asp Leu Asn Gln Phe Leu Ser Ala His
 1               5                  10                  15

Gln Leu

<210> SEQ ID NO 92
<211> LENGTH: 18
<212> TYPE: PRT
<213> ORGANISM: unknown
<220> FEATURE:
<223> OTHER INFORMATION: DDR2
```

```
<400> SEQUENCE: 92

Thr Glu Tyr Met Glu Asn Gly Asp Leu Asn Gln Phe Leu Ser Arg His
1               5                   10                  15
Glu Pro

<210> SEQ ID NO 93
<211> LENGTH: 21
<212> TYPE: PRT
<213> ORGANISM: unknown
<220> FEATURE:
<223> OTHER INFORMATION: ILK

<400> SEQUENCE: 93

Thr His Trp Met Pro Tyr Gly Ser Leu Tyr Asn Val Leu His Glu Gly
1               5                   10                  15
Thr Asn Phe Val Val
            20

<210> SEQ ID NO 94
<211> LENGTH: 16
<212> TYPE: PRT
<213> ORGANISM: unknown
<220> FEATURE:
<223> OTHER INFORMATION: JNK

<400> SEQUENCE: 94

Met Glu Leu Met Asp Ala Asn Leu Cys Gln Val Ile Gln Met Glu Leu
1               5                   10                  15

<210> SEQ ID NO 95
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<223> OTHER INFORMATION:
<221> NAME/KEY: AMIDATION
<222> LOCATION: (0)...(20)
<223> OTHER INFORMATION: Akt1/Raca

<400> SEQUENCE: 95

Gly Met Glu Tyr Ala Asn Gly Gly Glu Leu Phe Phe His Leu Ser Arg
1               5                   10                  15
Glu Arg Val Phe
            20

<210> SEQ ID NO 96
<211> LENGTH: 19
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(19)
<223> OTHER INFORMATION: Alk1

<400> SEQUENCE: 96

Gly Thr His Tyr His Glu His Gly Ser Leu Tyr Asp Phe Leu Gln Arg
1               5                   10                  15
Gln Thr Leu

<210> SEQ ID NO 97
<211> LENGTH: 22
```

```
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(22)
<223> OTHER INFORMATION: Braf

<400> SEQUENCE: 97

Lys Lys Lys Lys Lys Lys Gly Gly Ser Ser Leu Tyr His His Leu His
 1               5                  10                  15

Ile Ile Glu Thr Lys Phe
            20

<210> SEQ ID NO 98
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Braf

<400> SEQUENCE: 98

Gly Thr Gln Trp Ser Glu Gly Ser Ser Leu Tyr His His Leu His Ile
 1               5                  10                  15

Ile Glu Thr Lys Phe
            20

<210> SEQ ID NO 99
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: c-Abl

<400> SEQUENCE: 99

Gly Thr Glu Phe Met Thr Tyr Gly Asn Leu Leu Asp Tyr Leu Arg Glu
 1               5                  10                  15

Cys Asn Arg Gln Glu Val
            20

<210> SEQ ID NO 100
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION:
<223> OTHER INFORMATION: c-Met

<400> SEQUENCE: 100

Gly Leu Pro Tyr Met Lys His Gly Asp Leu Arg Asn Phe Ile Arg Asn
 1               5                  10                  15

Glu Thr His Asn Pro
            20
```

```
<210> SEQ ID NO 101
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: c-Raf

<400> SEQUENCE: 101

Gly Thr Gln Trp Ser Glu Gly Ser Ser Leu Tyr Lys His Leu His Val
 1               5                  10                  15

Gln Glu Thr Lys Phe
            20

<210> SEQ ID NO 102
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 11
<221> NAME/KEY: AMIDATION
<222> LOCATION: (0)...(14)
<223> OTHER INFORMATION: c-Raf

<400> SEQUENCE: 102

Ser Ser Leu Tyr Lys His Leu His Val Gln Glu Thr Lys Phe
 1               5                  10

<210> SEQ ID NO 103
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: c-Sea

<400> SEQUENCE: 103

Gly Leu Pro Tyr Met Arg His Gly Asp Leu Arg His Phe Ile Arg Ala
 1               5                  10                  15

Gln Glu Arg Ser Pro
            20

<210> SEQ ID NO 104
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: c-Src

<400> SEQUENCE: 104

Gly Thr Glu Tyr Met Ser Lys Gly Ser Leu Leu Asp Phe Leu Lys Gly
 1               5                  10                  15

Glu Thr Gly Lys Tyr Leu
            20

<210> SEQ ID NO 105
```

```
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 5
      benzyl ester at position 9
<221> NAME/KEY: AMIDATION
<222> LOCATION: (0)...(14)
<223> OTHER INFORMATION: c-Src

<400> SEQUENCE: 105

Gly Ser Leu Leu Asp Leu Lys Gly Glu Thr Gly Lys Phe Leu
 1               5                  10

<210> SEQ ID NO 106
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION:
<223> OTHER INFORMATION: CDK2

<400> SEQUENCE: 106

Gly Phe Glu Phe Leu His Gln Asp Leu Lys Lys Phe Met Asp Ala Ser
 1               5                  10                  15

Ala Leu Thr Gly Ile
            20

<210> SEQ ID NO 107
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 1
      benzyl ester at position 7
<221> NAME/KEY: AMIDATION
<222> LOCATION: (0)...(14)
<223> OTHER INFORMATION:
<223> OTHER INFORMATION: CDK2

<400> SEQUENCE: 107

Asp Leu Lys Lys Phe Met Asp Ala Ser Ala Leu Thr Gly Met
 1               5                  10

<210> SEQ ID NO 108
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 1
      benzyl ester at position 7
<221> NAME/KEY: AMIDATION
<222> LOCATION: (0)...(14)
<223> OTHER INFORMATION: CDK4

<400> SEQUENCE: 108

Asp Leu Arg Thr Tyr Leu Asp Lys Ala Pro Pro Pro Gly Leu
 1               5                  10

<210> SEQ ID NO 109
```

```
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: CDK4

<400> SEQUENCE: 109

Gly Phe Glu His Val Asp Gln Asp Leu Arg Thr Tyr Leu Asp Lys Ala
 1               5                  10                  15

Pro Pro Pro Gly Leu
            20

<210> SEQ ID NO 110
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: CDK6

<400> SEQUENCE: 110

Gly Phe Glu His Val Asp Gln Asp Leu Thr Thr Tyr Leu Asp Lys Val
 1               5                  10                  15

Pro Glu Pro Gly Val
            20

<210> SEQ ID NO 111
<211> LENGTH: 19
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(19)
<223> OTHER INFORMATION: Chk1

<400> SEQUENCE: 111

Gly Glu Tyr Ser Ser Gly Gly Glu Leu Phe Asp Arg Ile Glu Pro Asp
 1               5                  10                  15

Ile Gly Met

<210> SEQ ID NO 112
<211> LENGTH: 19
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(19)
<223> OTHER INFORMATION:
<223> OTHER INFORMATION: Chk1

<400> SEQUENCE: 112

Gly Glu Tyr Ala Ser Gly Gly Glu Leu Phe Asp Arg Ile Glu Pro Asp
 1               5                  10                  15

Ile Gly Met

<210> SEQ ID NO 113
```

```
<211> LENGTH: 19
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(19)
<223> OTHER INFORMATION:
<223> OTHER INFORMATION: CK IIa

<400> SEQUENCE: 113

Lys Lys Lys Lys Lys Gly Gly Asn Asn Thr Asp Phe Lys Gln Leu Tyr
 1               5                  10                  15

Gln Thr Leu

<210> SEQ ID NO 114
<211> LENGTH: 17
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(17)
<223> OTHER INFORMATION: CK IIa

<400> SEQUENCE: 114

Gly Phe Glu His Val Asn Asn Thr Asp Phe Lys Gln Leu Tyr Gln Thr
 1               5                  10                  15

Leu

<210> SEQ ID NO 115
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION:
<223> OTHER INFORMATION: Csk

<400> SEQUENCE: 115

Gly Thr Glu Tyr Met Ala Lys Gly Ser Leu Val Asp Tyr Leu Arg Ser
 1               5                  10                  15

Arg Gly Arg Ser Val Leu
            20

<210> SEQ ID NO 116
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 5
<221> NAME/KEY: AMIDATION
<222> LOCATION: (0)...(14)
<223> OTHER INFORMATION: Csk

<400> SEQUENCE: 116

Gly Ser Leu Val Asp Leu Arg Ser Arg Gly Arg Ser Val Leu
 1               5                  10

<210> SEQ ID NO 117
<211> LENGTH: 21
```

```
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Fak

<400> SEQUENCE: 117

Gly Met Glu Leu Ser Thr Leu Gly Glu Leu Arg Ser Phe Leu Gln Val
 1               5                  10                  15

Arg Lys Tyr Ser Leu
            20

<210> SEQ ID NO 118
<211> LENGTH: 17
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(17)
<223> OTHER INFORMATION: FGFR-3

<400> SEQUENCE: 118

Gly Gly Asn Leu Arg Glu Phe Leu Arg Ala Arg Arg Pro Pro Gly Leu
 1               5                  10                  15

Glu

<210> SEQ ID NO 119
<211> LENGTH: 16
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 5
      benzyl ester at position 16
<221> NAME/KEY: AMIDATION
<222> LOCATION: (0)...(16)
<223> OTHER INFORMATION: FGFR-3

<400> SEQUENCE: 119

Gly Asn Leu Arg Glu Phe Leu Arg Ala Arg Arg Pro Pro Gly Leu Glu
 1               5                  10                  15

<210> SEQ ID NO 120
<211> LENGTH: 23
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(23)
<223> OTHER INFORMATION: FGFR-3

<400> SEQUENCE: 120

Gly Val Glu Tyr Ala Ala Lys Gly Asn Leu Arg Glu Phe Leu Arg Ala
 1               5                  10                  15

Arg Arg Pro Pro Gly Leu Glu
            20

<210> SEQ ID NO 121
<211> LENGTH: 13
<212> TYPE: PRT
```

```
<213> ORGANISM: Artificial Sequence
<220> FEATURE:
<223> OTHER INFORMATION: stearyl at position 1
<221> NAME/KEY: AMIDATION
<222> LOCATION: (0)...(13)
<223> OTHER INFORMATION: FGFR-3

<400> SEQUENCE: 121

Gly Ser Phe Asp Thr Ser Lys Pro Pro Glu Glu Gln Leu
1               5                   10

<210> SEQ ID NO 122
<211> LENGTH: 23
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(23)
<223> OTHER INFORMATION: Flk1

<400> SEQUENCE: 122

Gly Val Glu Phe Ser Lys Phe Gly Asn Leu Ser Asn Phe Leu Arg Ala
1               5                   10                  15

Lys Arg Asn Leu Phe Val Pro
            20

<210> SEQ ID NO 123
<211> LENGTH: 17
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(17)
<223> OTHER INFORMATION:
<223> OTHER INFORMATION: Flk1

<400> SEQUENCE: 123

Gly Gly Asn Leu Ser Asn Phe Leu Arg Ala Lys Arg Asn Leu Phe Val
1               5                   10                  15

Pro

<210> SEQ ID NO 124
<211> LENGTH: 16
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(16)
<223> OTHER INFORMATION: Flk1

<400> SEQUENCE: 124

Gly Asn Leu Ser Asn Phe Leu Arg Ala Lys Arg Asn Leu Phe Val Pro
1               5                   10                  15

<210> SEQ ID NO 125
<211> LENGTH: 13
<212> TYPE: PRT
<213> ORGANISM: Artificial Sequence
<220> FEATURE:
<223> OTHER INFORMATION: stearyl at position 1
<221> NAME/KEY: AMIDATION
<222> LOCATION: (0)...(13)
<223> OTHER INFORMATION: Flk1
```

```
<400> SEQUENCE: 125

Gly Arg Phe Arg Gln Gly Lys Asp Tyr Val Gly Glu Leu
 1               5                  10

<210> SEQ ID NO 126
<211> LENGTH: 22
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(22)
<223> OTHER INFORMATION: GSK3b

<400> SEQUENCE: 126

Lys Lys Lys Lys Lys Lys Gly Gly Gly Val Ala Arg His Tyr Ser Arg
 1               5                  10                  15

Ala Lys Gln Thr Leu Pro
            20

<210> SEQ ID NO 127
<211> LENGTH: 13
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(13)
<223> OTHER INFORMATION: GSK3b

<400> SEQUENCE: 127

Val Ala Arg His Tyr Ser Arg Ala Lys Gln Thr Leu Pro
 1               5                  10

<210> SEQ ID NO 128
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: GSK3b

<400> SEQUENCE: 128

Gly Asp Tyr Val Pro Glu Thr Val Tyr Arg Val Ala Arg His Tyr Ser
 1               5                  10                  15

Arg Ala Lys Gln Thr Leu
            20

<210> SEQ ID NO 129
<211> LENGTH: 12
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(12)
<223> OTHER INFORMATION: GSK3b

<400> SEQUENCE: 129

Arg Val Ala Arg His Tyr Ser Arg Ala Lys Gln Thr
 1               5                  10
```

```
<210> SEQ ID NO 130
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: Hck

<400> SEQUENCE: 130

Gly Thr Glu Phe Met Ala Lys Gly Ser Leu Leu Asp Phe Leu Lys Ser
 1               5                  10                  15

Asp Glu Gly Ser Lys Gln
            20

<210> SEQ ID NO 131
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: Iak1

<400> SEQUENCE: 131

Gly Leu Glu Tyr Ala Pro Leu Gly Thr Val Tyr Arg Glu Leu Gln Lys
 1               5                  10                  15

Leu Ser Lys Phe
            20

<210> SEQ ID NO 132
<211> LENGTH: 23
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(23)
<223> OTHER INFORMATION: IKK-1

<400> SEQUENCE: 132

Gly Met Glu Tyr Ser Ser Gly Gly Asp Leu Arg Lys Leu Leu Asn Lys
 1               5                  10                  15

Pro Glu Asn Ser Ser Gly Leu
            20

<210> SEQ ID NO 133
<211> LENGTH: 23
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(23)
<223> OTHER INFORMATION:
<223> OTHER INFORMATION: IKK-2

<400> SEQUENCE: 133

Gly Met Glu Tyr Ser Gln Gly Gly Asp Leu Arg Lys Tyr Leu Asn Gln
 1               5                  10                  15
```

```
Phe Glu Asn Ser Ser Gly Leu
            20

<210> SEQ ID NO 134
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: ILK

<400> SEQUENCE: 134

Gly Thr His Trp Met Pro Tyr Gly Ser Leu Tyr Asn Val Leu His Glu
 1               5                  10                  15

Gly Thr Asn Phe Val Val
            20

<210> SEQ ID NO 135
<211> LENGTH: 13
<212> TYPE: PRT
<213> ORGANISM: Artificial Sequence
<220> FEATURE:
<223> OTHER INFORMATION: stearyl at position 1
<221> NAME/KEY: AMIDATION
<222> LOCATION: (0)...(13)
<223> OTHER INFORMATION: ILK

<400> SEQUENCE: 135

Gly Tyr Asn Val Leu His Glu Gly Thr Asn Phe Val Val
 1               5                  10

<210> SEQ ID NO 136
<211> LENGTH: 19
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(19)
<223> OTHER INFORMATION:
<223> OTHER INFORMATION: IRK

<400> SEQUENCE: 136

Gly Met Glu Leu Met Ala His Gly Asp Leu Lys Ser Tyr Leu Arg Ser
 1               5                  10                  15

Leu Arg Pro

<210> SEQ ID NO 137
<211> LENGTH: 12
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(12)
<223> OTHER INFORMATION: IRK

<400> SEQUENCE: 137

Ala Gln Asn Asn Pro Gly Arg Pro Pro Thr Leu
 1               5                  10

<210> SEQ ID NO 138
<211> LENGTH: 13
```

```
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: IRK

<400> SEQUENCE: 138

Gly Leu Lys Ser Tyr Leu Arg Ser Leu Arg Pro Glu Ala
 1               5                  10

<210> SEQ ID NO 139
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: IRK

<400> SEQUENCE: 139

Gly Ala Glu Asn Asn Pro Gly Arg Pro Pro Thr Leu
 1               5                  10

<210> SEQ ID NO 140
<211> LENGTH: 17
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(17)
<223> OTHER INFORMATION: IRK

<400> SEQUENCE: 140

Gly Leu Arg Pro Glu Ala Glu Asn Asn Pro Gly Arg Pro Pro Pro Thr
 1               5                  10                  15

Leu

<210> SEQ ID NO 141
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Jak1

<400> SEQUENCE: 141

Gly Met Glu Phe Leu Pro Ser Gly Ser Leu Lys Glu Tyr Leu Pro Lys
 1               5                  10                  15

Asn Lys Asn Lys Ile
             20

<210> SEQ ID NO 142
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
```

```
<222> LOCATION: (0)...(13)
<223> OTHER INFORMATION: Jak1

<400> SEQUENCE: 142

Gly Leu Lys Glu Tyr Leu Pro Lys Asn Lys Asn Lys Ile
 1               5                  10

<210> SEQ ID NO 143
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: Jak2

<400> SEQUENCE: 143

Gly Leu Arg Asp Tyr Leu Gln Lys His Lys Glu Arg Ile
 1               5                  10

<210> SEQ ID NO 144
<211> LENGTH: 11
<212> TYPE: PRT
<213> ORGANISM: Artificial Sequence
<220> FEATURE:
<223> OTHER INFORMATION: stearyl at position 1
<221> NAME/KEY: AMIDATION
<222> LOCATION: (0)...(11)
<223> OTHER INFORMATION: Jak2

<400> SEQUENCE: 144

Gly Leu Arg Asp Tyr Leu Gln Lys His Lys Glu
 1               5                  10

<210> SEQ ID NO 145
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: Jak3

<400> SEQUENCE: 145

Gly Met Glu Tyr Leu Pro Ser Gly Ser Leu Arg Asp Phe Leu Gln Arg
 1               5                  10                  15

His Arg Ala Leu
            20

<210> SEQ ID NO 146
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Jak3

<400> SEQUENCE: 146

Gly Met Glu Tyr Leu Pro Ser Gly Ser Leu Arg Asp Phe Leu Gln Arg
 1               5                  10                  15

His Arg Ala Arg Leu
```

<210> SEQ ID NO 147
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: Jak3

<400> SEQUENCE: 147

Gly Leu Arg Asp Phe Leu Gln Arg His Arg Ala Arg Leu
1               5                   10

<210> SEQ ID NO 148
<211> LENGTH: 14
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 5
<221> NAME/KEY: AMIDATION
<222> LOCATION: (0)...(14)
<223> OTHER INFORMATION: Lck

<400> SEQUENCE: 148

Gly Ser Leu Val Asp Leu Lys Thr Pro Ser Gly Ile Lys Leu
1               5                   10

<210> SEQ ID NO 149
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: Lck

<400> SEQUENCE: 149

Gly Thr Glu Tyr Met Glu Asn Gly Ser Leu Val Asp Phe Leu Lys Thr
1               5                   10                  15

Pro Ser Gly Ile Lys Leu
            20

<210> SEQ ID NO 150
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: Lyn

<400> SEQUENCE: 150

Gly Thr Glu Tyr Met Ala Lys Gly Ser Leu Leu Asp Phe Leu Lys Ser
1               5                   10                  15

Asp Glu Gly Gly Lys Val
            20

<210> SEQ ID NO 151

```
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: MARK1

<400> SEQUENCE: 151

Gly Met Glu Tyr Ala Ser Gly Gly Glu Val Phe Asp Tyr Leu Val Ala
 1               5                  10                  15

His Gly Arg Met
            20

<210> SEQ ID NO 152
<211> LENGTH: 15
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 2
      benzyl ester at position 5
<221> NAME/KEY: AMIDATION
<222> LOCATION: (0)...(15)
<223> OTHER INFORMATION: PDGFR-b

<400> SEQUENCE: 152

Gly Asp Leu Val Asp Tyr Leu His Arg Asn Lys His Thr Phe Leu
 1               5                  10                  15

<210> SEQ ID NO 153
<211> LENGTH: 22
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: PDGFR-b

<400> SEQUENCE: 153

Gly Thr Glu Tyr Ser Arg Tyr Gly Asp Leu Val Asp Tyr Leu His Arg
 1               5                  10                  15

Asn Lys His Thr Phe Leu
            20

<210> SEQ ID NO 154
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: PKCb

<400> SEQUENCE: 154

Gly Met Glu Tyr Val Asn Gly Gly Asp Leu Met Tyr His Ile Gln Gln
 1               5                  10                  15

Val Gly Arg Phe
            20

<210> SEQ ID NO 155
```

```
<211> LENGTH: 20
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(20)
<223> OTHER INFORMATION: PKCb

<400> SEQUENCE: 155

Lys Lys Lys Lys Lys Lys Gly Gly Asp Leu Met Tyr His Ile Gln Gln
 1               5                  10                  15

Val Gly Arg Phe
            20

<210> SEQ ID NO 156
<211> LENGTH: 12
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 5
<221> NAME/KEY: AMIDATION
<222> LOCATION: (0)...(12)
<223> OTHER INFORMATION: Plk

<400> SEQUENCE: 156

Arg Ser Leu Leu Glu Leu His Lys Arg Arg Lys Ala
 1               5                  10

<210> SEQ ID NO 157
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<223> OTHER INFORMATION: benzyl ester at position 6
<221> NAME/KEY: AMIDATION
<222> LOCATION: (0)...(13)
<223> OTHER INFORMATION: Plk

<400> SEQUENCE: 157

Gly Arg Ser Leu Leu Glu Leu His Lys Arg Arg Lys Ala
 1               5                  10

<210> SEQ ID NO 158
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: Plk

<400> SEQUENCE: 158

Gly Leu Glu Leu Ser Arg Arg Arg Ser Leu Leu Glu Leu His Lys Arg
 1               5                  10                  15

Arg Lys Ala Leu
            20

<210> SEQ ID NO 159
<211> LENGTH: 22
<212> TYPE: PRT
<213> ORGANISM: Artificial Sequence
```

```
<220> FEATURE:
<221> NAME/KEY: MYRISTATE
<222> LOCATION: (1)...(0)
<221> NAME/KEY: AMIDATION
<222> LOCATION: (0)...(22)
<223> OTHER INFORMATION: Ret

<400> SEQUENCE: 159

Gly Val Glu Tyr Ala Lys Tyr Gly Ser Leu Arg Gly Phe Leu Arg Glu
 1               5                  10                  15
Ser Arg Lys Val Gly Pro
            20

<210> SEQ ID NO 160
<211> LENGTH: 15
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: benzyl ester at position 9
<221> NAME/KEY: AMIDATION
<222> LOCATION: (0)...(15)
<223> OTHER INFORMATION: Ret

<400> SEQUENCE: 160

Gly Ser Leu Arg Gly Phe Leu Arg Glu Ser Arg Lys Val Gly Pro
 1               5                  10                  15

<210> SEQ ID NO 161
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Ron

<400> SEQUENCE: 161

Gly Leu Pro Tyr Met Cys His Gly Asp Leu Leu Gln Phe Ile Arg Ser
 1               5                  10                  15
Pro Gln Arg Asn Pro
            20

<210> SEQ ID NO 162
<211> LENGTH: 20
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(20)
<223> OTHER INFORMATION: SNK

<400> SEQUENCE: 162

Gly Leu Glu Tyr Ser Ser Arg Arg Ser Met Ala His Ile Leu Lys Ala
 1               5                  10                  15
Arg Lys Val Leu
            20

<210> SEQ ID NO 163
<211> LENGTH: 20
<212> TYPE: PRT
<213> ORGANISM: Artificial Sequence
<220> FEATURE:
```

```
<221> NAME/KEY: MYRISTATE
<222> LOCATION: (1)...(0)
<221> NAME/KEY: AMIDATION
<222> LOCATION: (0)...(20)
<223> OTHER INFORMATION: Syk

<400> SEQUENCE: 163

Gly Met Glu Met Ala Glu Leu Gly Pro Leu Asn Lys Tyr Leu Gln Gln
1               5                   10                  15

Asn Arg His Val
            20

<210> SEQ ID NO 164
<211> LENGTH: 19
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(19)
<223> OTHER INFORMATION: TGFbRII

<400> SEQUENCE: 164

Gly Thr Ala Phe His Ala Lys Gly Asn Leu Gln Glu Tyr Leu Thr Arg
1               5                   10                  15

His Val Ile

<210> SEQ ID NO 165
<211> LENGTH: 25
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(25)
<223> OTHER INFORMATION: TrkB

<400> SEQUENCE: 165

Gly Phe Glu Tyr Met Lys His Gly Asp Leu Asn Lys Phe Leu Arg Ala
1               5                   10                  15

His Gly Pro Asp Ala Val Leu Met Ala
            20                  25

<210> SEQ ID NO 166
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: TrkB

<400> SEQUENCE: 166

Gly Leu Arg Ala His Gly Pro Asp Ala Val Leu Met Ala
1               5                   10

<210> SEQ ID NO 167
<211> LENGTH: 11
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
```

```
<222> LOCATION: (0)...(11)
<223> OTHER INFORMATION: TrkB

<400> SEQUENCE: 167

Gly Leu Arg Ala His Gly Pro Asp Ala Val Leu
1               5                   10

<210> SEQ ID NO 168
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: TrkB

<400> SEQUENCE: 168

Gly Leu Asn Phe Lys Leu Arg Ala His Gly Pro Asp Ala
1               5                   10

<210> SEQ ID NO 169
<211> LENGTH: 13
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(13)
<223> OTHER INFORMATION: TrkB

<400> SEQUENCE: 169

Gly Phe Lys Leu Arg Ala His Gly Pro Asp Ala Val Leu
1               5                   10

<210> SEQ ID NO 170
<211> LENGTH: 21
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(21)
<223> OTHER INFORMATION: Zap70

<400> SEQUENCE: 170

Gly Met Glu Met Ala Gly Gly Pro Leu His Lys Phe Leu Val Gly
1               5                   10                  15

Lys Arg Glu Glu Ile
            20

<210> SEQ ID NO 171
<211> LENGTH: 21
<212> TYPE: PRT
<213> ORGANISM: Unknown
<220> FEATURE:
<223> OTHER INFORMATION: IRK

<400> SEQUENCE: 171

Met Ala His Gly Asp Leu Lys Ser Tyr Leu Arg Ser Leu Arg Pro Glu
1               5                   10                  15

Ala Glu Asn Asn Pro
            20
```

```
<210> SEQ ID NO 172
<211> LENGTH: 8
<212> TYPE: PRT
<213> ORGANISM: Unknown
<220> FEATURE:
<223> OTHER INFORMATION: endothelial growth factor receptor

<400> SEQUENCE: 172

Lys Phe Asp Val Ile Asn Leu Ala
 1               5
```

SHORT PEPTIDES WHICH SELECTIVELY MODULATE THE ACTIVITY OF PROTEIN KINASES

CROSS-REFERENCE TO RELATED APPLICATIONS

The present application is a continuation of U.S. application Ser. No. 09/161,094, filed Sep. 25, 1998, now abandoned, the entire contents of which being incorporated herein by reference.

BACKGROUND OF THE INVENTION

There are a group of proteins that constitute the eukaryotic protein kinase superfamily. Enzymes of this class specifically phosphorylate serine, threonine or tyrosine residues of intracellular proteins. These enzymes are important in mediating signal transduction in multicellular organisms. Many of the protein kinases are part of transmembrane receptors. Others occur as intracellular proteins which take part in signal transduction within the cell, including signal transduction to the nucleus and activation of other proteins. Other protein kinases, such as G protein-coupled receptor kinases, are bound to cell membranes and participate in transmembrane signaling.

As such, phosphorylation of serine, threonine or tyrosine by protein kinases is an important mechanism for regulating intracellular events in response to environmental changes. A wide variety of cellular events are regulated by protein kinases. A few examples include cellular proliferation, cellular differentiation, the ability of cells to enter and/or complete mitosis, cellular transformation by RNA viruses, oncogenesis, control of fat metabolism, immune responses, inflammatory responses and the control of carbohydrate metabolism.

Enhanced protein kinase activity can lead to persistent stimulation by secreted growth factors and other growth inducing factors which, in turn, can lead to proliferative diseases such as cancer, to nonmalignant proliferative diseases such as arteriosclerosis, psoriasis and to inflammatory response such as septic shock. Decreased function can also lead to disease. For example, a decrease in the activity of insulin receptor kinase is a cause of various types of diabetes. Severe reduction of the B cell progenitor kinase leads to human X-linked agammaglobulinemia.

Thus, agents which can modulate (increase or decrease) the activity of protein kinases have great potential for the treatment of a wide variety of diseases and conditions such as cancer, obesity, autoimmune disorders, inflammation and diabetes. Such agents also have utility in deciphering the mode of action of protein kinases and how these proteins regulate cellular functions and activities.

SUMMARY OF THE INVENTION

It has now been found that short peptides which are derivatives of the αD region of a protein kinase can significantly affect the activities of cells expressing the protein kinase when incubated with the cells (the "αD region" is defined hereinbelow). For example, the peptide derivatives of the αD region of Jak3 inhibit the proliferation of human endothelial cells and the human prostate cancer cell line PC3 in vitro at concentrations as low as 0.3 μM (Example 2). Based on the aforementioned discoveries, novel peptides are disclosed herein which are peptide derivatives of the αD region of protein kinases. Also disclosed are methods of identifying a peptide derivative of an αD region of a protein kinase that modulates the activity of the protein kinase. Methods of modulating the activity of a protein kinase in a subject are also disclosed.

One embodiment of the present invention is a novel peptide which is a peptide derivative of the αD region of a protein kinase. The peptide comprises between about five and about thirty amino acid residues or amino acid residue analogs of the αD region. The peptide modulates the activity of the protein kinase. The N-terminus and/or C-terminus of the peptide can be substituted or unsubstituted. The peptide can be linear or cyclic.

Another embodiment of the present invention is a method of modulating the activity of a protein kinase in a subject. The method comprises administering a therapeutically effective amount of a peptide that is a derivative of the αD region of the protein kinase, as described above.

Yet another embodiment of the present invention is a method of identifying a peptide which modulates the activity of a protein kinase. The method comprises providing a "test peptide" which has from about five to about thirty amino acids or amino acid analogs and which is a peptide derivative of the αD region of the protein kinase. The test peptide is incubated with cells having a cellular activity or function under the control of the protein kinase under conditions suitable for assessing the activity of the protein kinase. The activity of the protein kinase is assessed and compared with the activity of the protein kinase in cells of the same cell type grown under the same conditions in the absence of the test peptide. A greater or lesser activity compared with cells grown in the absence of the test peptide indicates that the test peptide modulates the activity of the protein kinase.

The peptides of the present invention can be used in the treatment of a wide variety of diseases caused by overactivity or underactivity of a protein kinase. Examples include, but are not limited to, cancer, diseases caused by proliferation of smooth muscle (e.g., restenosis and atherosclerosis), skin disorders, diabetes, obesity, diseases of the central nervous system, inflammatory disorders, autoimmune diseases and other immune disorders, osteoporosis and cardiovascular diseases. The peptides of the present invention also have in vitro utilities, for example, in the generation of antibodies that specifically bind the protein kinase from which the peptide was derived. These antibodies can be used to identify cells expressing the protein kinase and to study the intracellular distribution of the protein kinase. In addition, the peptides of the present invention can be used to identity and quantitate ligands that bind the αD region of the protein kinase from which the peptide was derived.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 1A–1I are a table illustrating the amino acid sequences of the αD region of the following protein kinases:
c-Raf (SEQ ID NO:1); Araf (SEQ ID NO:2); Braf (SEQ ID NO:3); cyclic AMP dependent protein kinases a, b and g (cAPK) (SEQ ID NO:4 to 5); protein kinase C alpha through theta (PKC) (SEQ ID NO:6 to 12); Akt 1 and 2 (also called Rac α and β) (SEQ ID NO:13); glycogen synthase kinase α and β (GSK3) (SEQ ID NO:14 to 15); casein kinases type II α and α' (CK) (SEQ ID NO:16 to 17); G-receptor coupled protein kinase β-2 adrenergic receptor kinases 1 and 2 (bARK1, 2) (SEQ ID NO:18); G-protein coupled receptor kinases GRK1 and GRK4 through GRK6 (SEQ ID NO:19 to 22); calmodulin dependent kinases types I and II a, b, c and d (CaMK) (SEQ ID NO:23 to 24); members of the Polo-associated family: Plk, Plx1, polo, SNK, CDC5, Sak, Prk, Fnk, Plo1 (SEQ ID NO:25 to 32); MARK1 and MARK2 and p78 (SEQ ID NO:33 to 34); cyclin dependent kinases 2, 4 and 6 (SEQ ID NO:35 to 37); Src, Yes, Fyn, Fgr, Lyn, Hck, Lck (SEQ ID NO:38 to 44); Csk and Matk (SEQ ID NO:45 to 46); focal adhesion kinase (FAX) (SEQ ID NO:47); c-Abl (SEQ ID NO:48); endothelial growth factor receptors Tie, Tek, FGF receptor (Flg, Bek, FGFR3, FGFR4), PDGF receptor α and β, Flt 1 and 4 and Flk1 (SEQ ID NO:49 to 59); HGF receptors c-Met, c-Sea and Ron (SEQ ID NO:60 to 62); EGF receptor (EGFR, ErbB2, ErbB3, ErbB4) (SEQ ID NO:63 to 66); Ret (SEQ ID NO:67); NGF receptors (Trk) (SEQ ID NO:68 to 70); Syk and Zap70 (SEQ ID NO:71 to 72); Jak kinases 1 through 3 and Tyk2 (SEQ ID NO:73 to 76); Iak1 (SEQ ID NO:77); Chk1 (SEQ ID NO:78); NFkB inhibitor kinases, known also as I-kappa B kinases IKK1 and IKK2 (SEQ ID NO:79 to 80); death associated protein kinase (DAPK) (SEQ ID NO:81); insulin receptor kinase (IRK) (SEQ ID NO:82); TGFβ receptor type II (SEQ ID NO:83); Activin receptor type II A and B (ACTR) (SEQ ID NO:84 to 85); Activin receptor-like kinases 1 through 6 (ALK1, 2, 3, 4, 5, 6) (SEQ ID NO:86 to 90); discoidin domain receptor 1 (DDR) and Tyro10 (SEQ ID NO:91 to 92); ILK (SEQ ID NO:93); Jun kinase (JNK) (SEQ ID NO:94)

FIGS. 2A–2F are a group of sequences illustrating the consensus amino acid sequences of the αD region found among the family of protein kinases. Also shown are examples of conservative substitutions in these amino acid sequences. The Conservative amino acid substitutions shown include the amino acid sequences of the αD region of: c-Raf (SEQ ID NO:1); Araf (SEQ ID NO:2); Braf (SEQ ID NO:3); cyclic AMP dependent protein kinases a, b and g (cAPK) (SEQ ID NO:4 to 5); protein kinase C alpha through theta (PKC) (SEQ ID NO:6 to 12); Akt 1 and 2 (also called Rae α and β) (SEQ ID NO:13); glycogen synthase kinase α and β (GSK3) (SEQ ID NO:14 to 15); casein kinases type 11 α and α' (CK) (SEQ ID NO:16 to 17); G-receptor coupled protein kinases β-2 adrenergic receptor kinases 1 and 2 (bARK1, 2) (SEQ ID NO:18); G-protein coupled receptor kinases GRKI and GRK4 through GRK6 (SEQ ID NO:19 to 22); calmodulin dependent kinases types I and II a, b, c and d (CaMK) (SEQ ID NO:23 to 24); members of the Polo-associated family: Plk, Plx1, polo, SNK, CDC5, Sak, Prk, Fnk, Plo1 (SEQ ID NO:25 to 32); NLkRK1 and MARK2 and p78 (SEQ ID NO:33 to 34); cyclin dependent kinases 2, 4 and 6 (SEQ ID NO:35 to 37); Src, Yes, Fyn, Fgr, Lyn, Hck, Lck (SEQ ID NO:38 to 44); Csk and Matk (SEQ ID NO:45 to 46); focal adhesion kinase (FAK) (SEQ ID NO:47); c-Abl (SEQ ID NO:48); endothelial growth factor receptors Tie, Tek, FGF receptor (Flg, Bek, FGFR3, FGFR4), PDGF receptor α and β, Flt 1 and 4 and Flk1 (SEQ ID NO:49 to 59); HGF receptors c-Met, cSea and Ron (SEQ ID NO:60 to 62); EGF receptor (EGFR, ErbB2, ErbB3, ErbB4) (SEQ ID NO:63 to 66); Ret (SEQ ID NO:67); NGF receptors (Trk) (SEQ ID NO:68 to 70); Syk and Zap70 (SEQ ID NO:71 to 72); Jak kinases 1 through 3 and Tyk2 (SEQ ID NO:73 to 76); lak1 (SEQ ID NO:77); Chk1 (SEQ ID NO:78); NFkB inhibitor kinases IKK1 and IKK2 (SEQ ID NO:79 to 80); death associated protein kinase (DAPK) (SEQ ID NO:81); insulin receptor kinase (IRK) (SEQ ID NO:82); TGFβ receptor type II (SEQ ID NO:83); Activin receptor type 11 A and B (ACTR) (SEQ ID NO:84 to 85); Activin receptor-like kinases 1 through 6 (ALK1, 2, 3, 4, 5, 6) (SEQ ID NO:86 to 90); discoidin domain receptor 1 (DDR) and Tyro 10 (SEQ ID NO:91 to 92); ILK (SEQ ID NO:93); and Jun kinase (JNK) (SEQ ID NO:94) An "*" indicates an aliphatic, substituted aliphatic, benzylic, substituted benzylic, aromatic or substituted aromatic ester of glutamic acid or aspartic acid.

FIGS. 3A–3D are a Table illustrating the sequences of the following peptides:

Akt1/Raca K014D001; ALK1 K048D101; Braf K003D001 K003D101; c-Abl K061D101; c-Met K073D101; c-Raf K001D101 K001D001; c-Sea K074D101; c-Src K051D101 K051D001; CDK2 K049D101 K049D001; CDK4 K050D001 K050D101; CDK6 089D101; Chk1 K088D102 K088D101; CK IIα K022D001 K022D101; Csk K058D101 K058D001; Fak K060D101; FGFR-3 K071D101 K071D001 K071D102 K071D901; Flk1 K068D102 K068D101 K068D001 K068D901; GSK3β K018D003 K018D002 K018D101 K018D001; Hck K056D101; Iak1 K087D101; IKK-1 K090D101; IKK2 K091D101; ILK K107D101 K107D901; IRK K094D001 K094D101 K094D102 K094D103 K094D104; Jak1 K084D101 K084D102; Jak2 K085D102 K085D105; Jak3 K086D101 K086D102 K086D103; Lck K057D001 K057D101; Lyn K055D101; MARK1 K045D101; PDGFR-b K064D001 K064D101; PKCβ K008D101 K008D001; Plk K035D001 K035D101 K035D102; Ret K080D101 K080D001; Ron K075D101; SNK K038D101; Syk K082D101; TGFβRII K093D101; TrkB K102D101 K102D106 K102D107 K102D108 K102D109; Zap70 K083D101 (SEQ ID NO:95 to 170, respectively).

Peptides are either N-acetylated, N-stearylated or N-myristylated and C-amidated. "E!" indicates a benzyl ester of glutamic acid and "D!" indicates a benzyl ester of aspartic acid. FIG. 3 also indicates from which protein kinase each peptide is derived.

Figure 4:
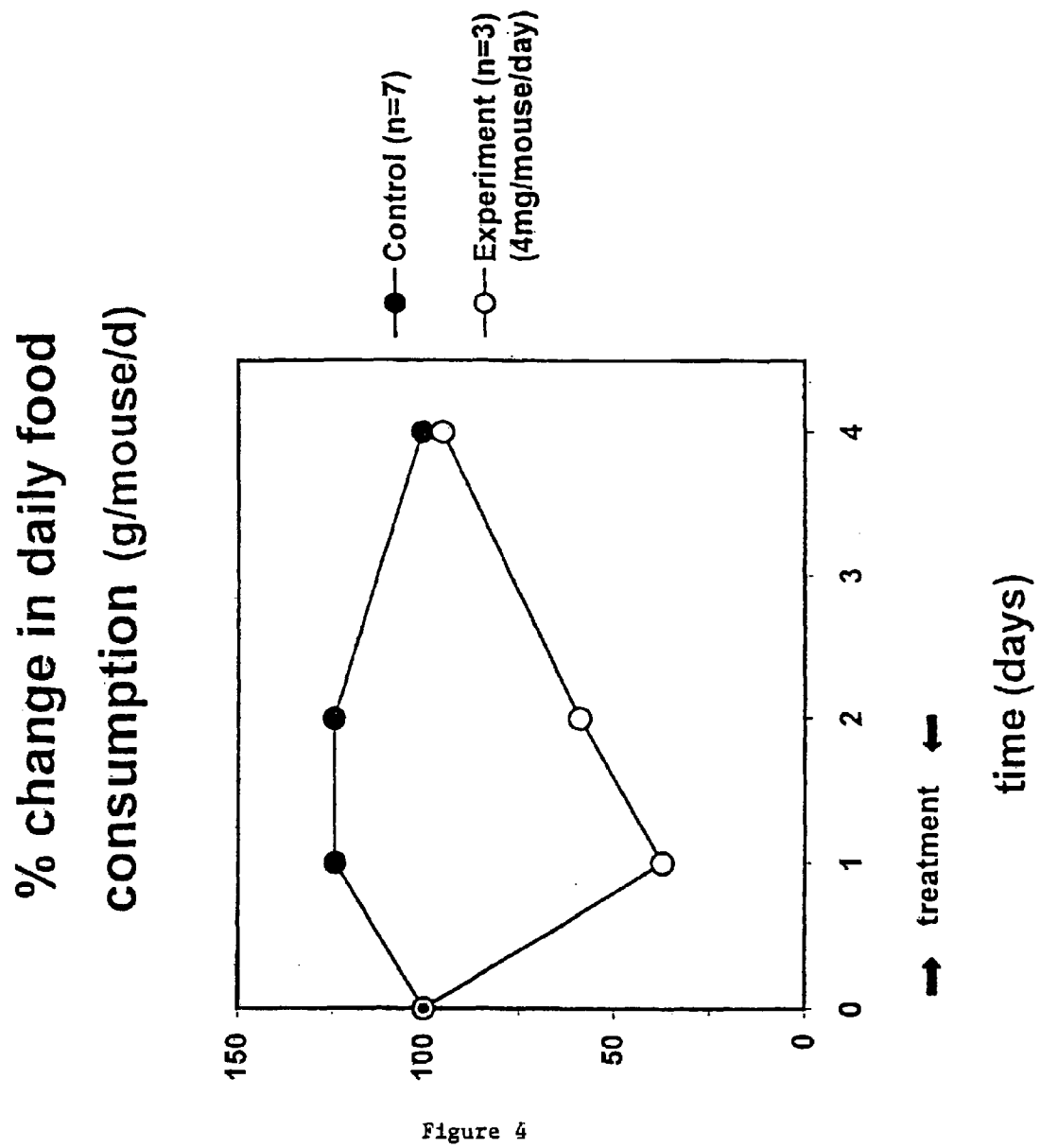

FIG. 4 is a graphical representation of the percent change in daily food consumption for CB6F1 mice. Members of the experimental group were administered a Jak2-derived peptide and the members of the control group were administered vehicle alone.

Figure 5:
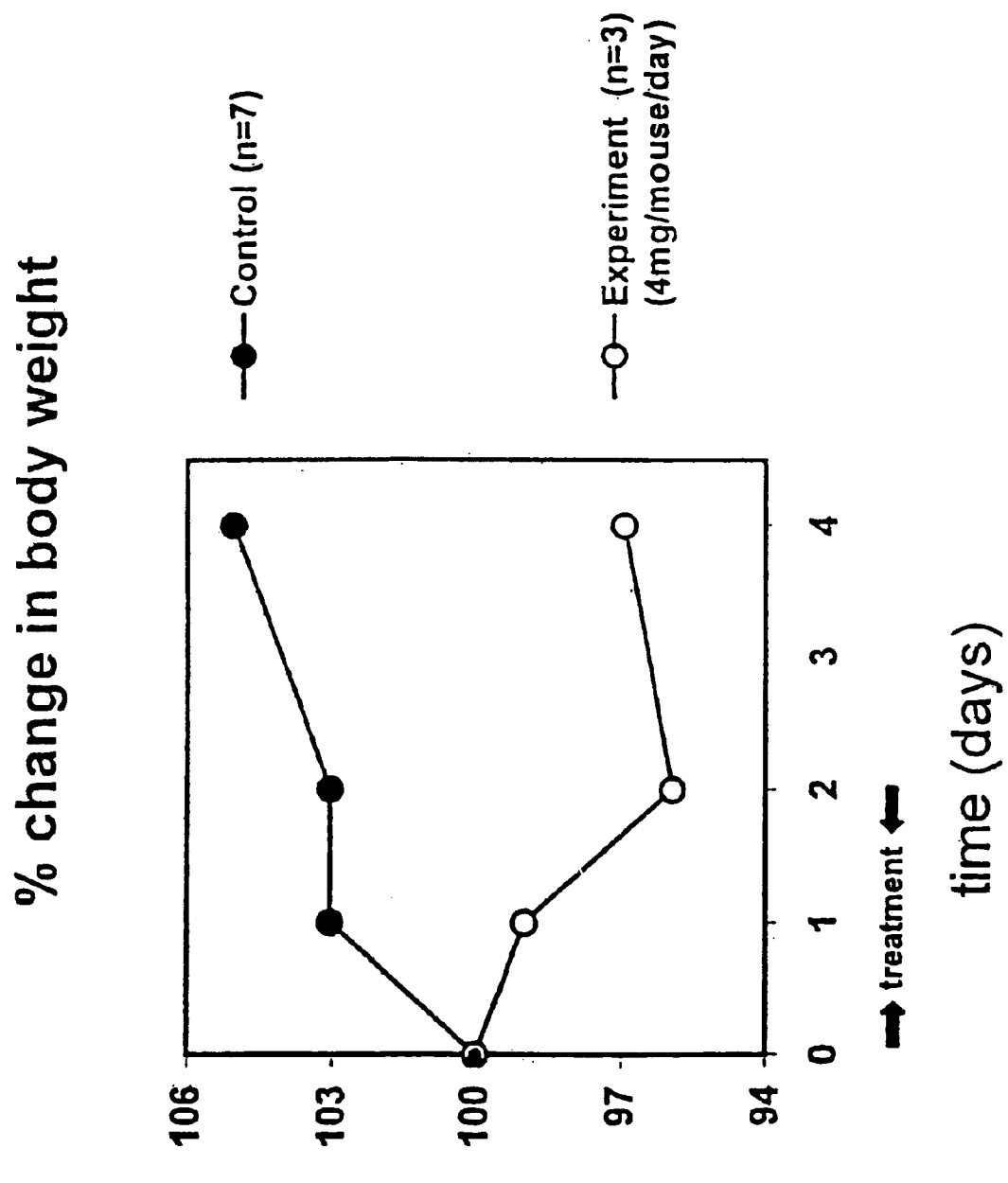

FIG. 5 is a graphical representation of the percent change in daily body weight for CB6F1 mice. Members of the experimental group were administered a Jak2-derived peptide and members of the control group were administered vehicle alone.

Figure 6:
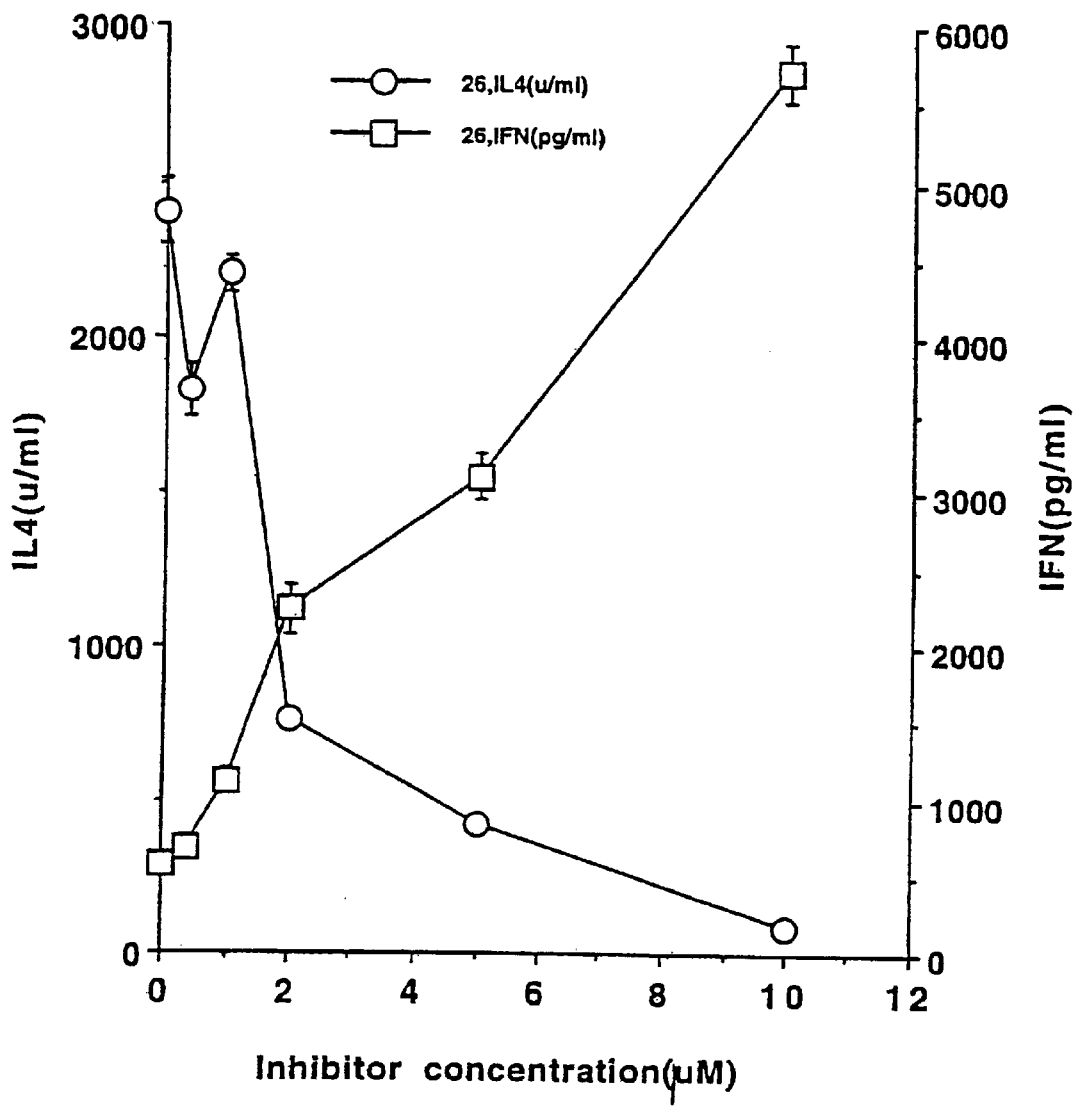

FIG. 6 is a graphical representation of the amount of IL-4 or IFNγ that is secreted by CD4+ T cells that have been incubated with different concentrations of a Jak3 peptide.

Figure 7:
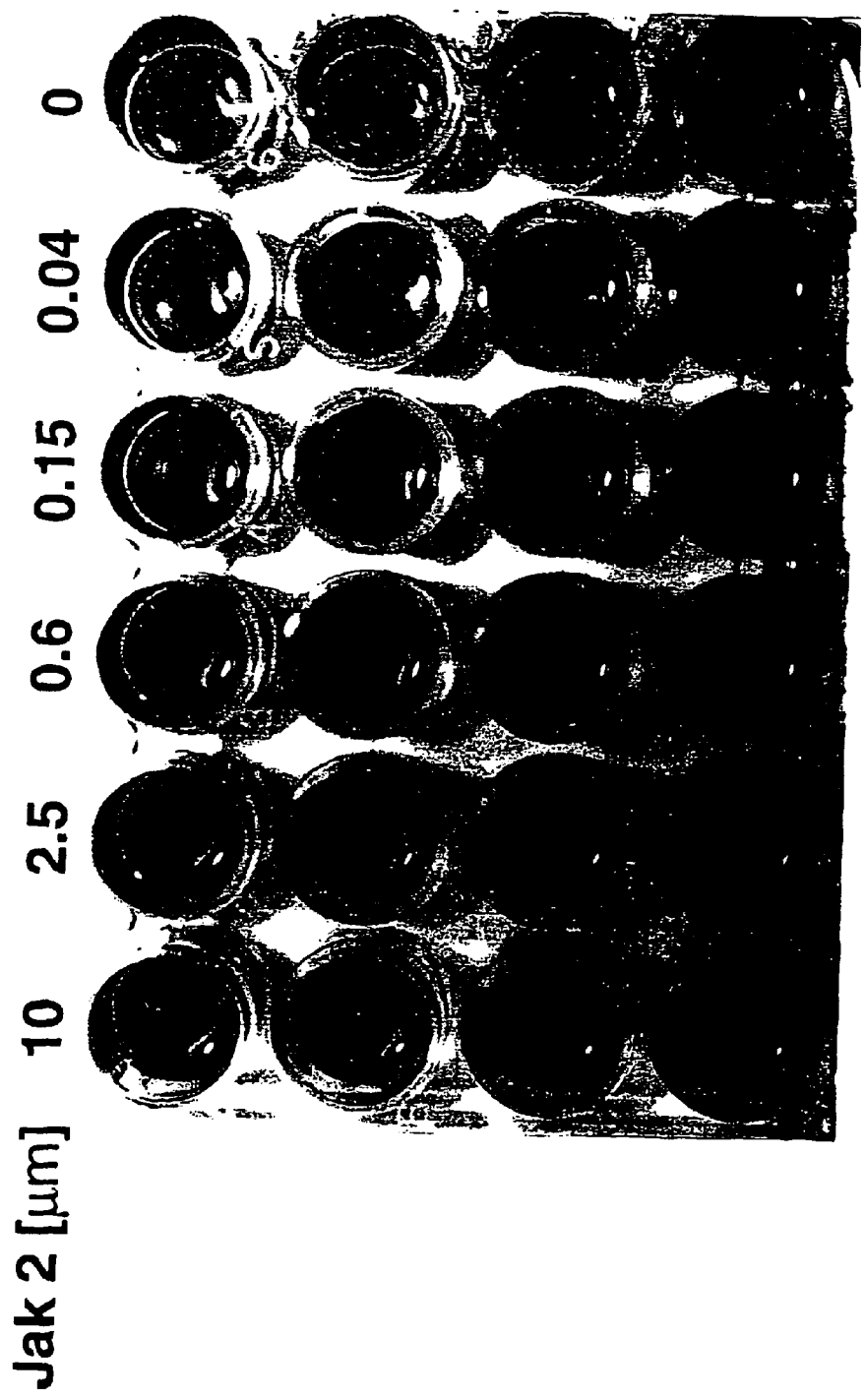

FIG. 7 is a pictorial depiction of melanin (pigment) production by B16 melanoma cells that have been incubated with different concentrations of a Jak2-derived peptide.

DETAILED DESCRIPTION OF THE INVENTION

A protein kinase (hereinafter "PK") is an intracellular or membrane bound protein which uses the gamma phosphate of ATP or GTP to generate phosphate monoesters on the hydroxyl group of a serine or threonine residue, or on the phenolic group of a tyrosine residue. PKs have homologous "kinase domains" or "catalytic domains" which carry out this phosphorylation. Based on a comparison of a large number of protein kinases, it is now known that the kinase domain of protein kinases can be divided into twelve subdomains. These are regions that are generally uninterrupted by large amino acid insertions and which contain characteristic patterns of conserved residues (Hanks and Hunter, "The Eukaryotic Protein Kinase Superfamily", in Hardie and Hanks ed., *The Protein Kinase Facts Book, Volume I*, Academic Press, Chapter 2, 1995). These subdomains are referred to as Subdomain I through Subdomain XII.

The "αD region" referred to herein is found within the kinase domain of PKs in Subdomain V and the beginning of Subdomain VI. Because of the high degree of homology found in the subdomains of different protein kinases, the amino acid sequences of the domains of different PKs can be aligned. Thus, the αD region of a PK can be defined by reference to the amino acid sequence of a prototypical protein kinase, for example PKA-Cα, and can be said to correspond to a contiguous sequence of about twenty amino acid residues found between about amino acid 120 and 139 of PKA-Cα.

A second definition of the αD region of a PK, which is complementary to the definition provided in the preceding paragraph, can be made by reference to the three dimensional structure of the kinase domain of PKs. The kinase domain of PKs has been found to contain at least nine alpha helices, referred to as helix A through helix I and nine beta sheets, referred to as b1 through b9 (Taylor et al., *Phil. Trans. R. Soc. Lond.* B340:315 (1993), Mohammadi et al., *Cell* 86:577 (1996) and Hubbard et al., *Nature* 372:746 (1994)). The αD region is a contiguous sequence of about fifteen to forty amino acids beginning at the end of the b5 beta sheet and extending through the D helix and the following loop to the beginning of helix E.

Optionally, the C-terminus or the N-terminus of the peptides of the present invention, or both, can be substituted with a carboxylic acid protecting group or an amine protecting group, respectively. Suitable protecting groups are described in Green and Wuts, *"Protecting Groups in Organic Synthesis"*, John Wiley and Sons, Chapters 5 and 7, 1991, the teachings of which are incorporated herein by reference. Preferred protecting groups are those that facilitate transport of the peptide into a cell, for example, by reducing the hydrophilicity and increasing the lipophilicity of the peptide. Examples of N-terminal protecting groups include acyl groups (—CO—$R_1$) and alkoxy carbonyl or aryloxy carbonyl groups (—CO—O—$R_1$), wherein $R_1$ is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, lauroyl, palmitoyl, myristoyl, stearyl, phenyl-CO—, substituted phenyl-CO—, benzyl-CO— and (substituted benzyl)-CO—. Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO—, benzyl-O—CO—, (substituted benzyl)-O—CO—. In order to facilitate the N-acylation, a glycine can be added to the N-terminus of the sequence. The carboxyl group at the C-terminus can be protected, for example, by an amide (i.e., the hydroxyl group at the C-terminus is replaced with —$NH_2$, —$NHR_2$ and —$NR_2R_3$) or ester (i.e., the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0–2 additional heteroatoms such as nitrogen, oxygen or sulfur.

Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —$N(ethyl)_2$, —N(methyl) (ethyl), —NH(benzyl), —N(C1–C4 alkyl) (benzyl), —NH(phenyl), —N(C1–C4 alkyl)(phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

A "peptide derivative of the αD region" includes a peptide having the amino acid sequence of the αD region. A "peptide derivative of the αD region" also includes a subsequence of the αD region of the PK. A subsequence of a protein region is a contiguous sequence of from about five to about thirty amino acids or amino acid residues found within a larger sequence. Thus, a subsequence of the αD region is a contiguous sequence of from about five to about thirty amino acids or amino acid residues found within the αD region. A subsequence of the αD region can also be referred to as a "fragment" of the αD region.

A "peptide derivative" also includes a peptide having a "modified sequence" in which one or more amino acids in the original sequence or subsequence have been substituted with a naturally occurring amino acid or amino acid analog (also referred to as a "modified amino acid"). In one aspect of the present invention, the peptide derivative has a sequence corresponding to a subsequence of the αD region of a PK, with the proviso that any one amino acid residue in the peptide derivative can differ from the corresponding amino acid residue in the subsequence. For example, if the subsequence is [$AA_1$]-[$AA_2$]-$AA_3$]-[$AA_4$]-[$AA_5$], then the peptide derivative can be [$AA_1'$]-[$AA_2$]-[$AA_3$]-[$AA_4$]-[$AA_5$], [$AA_1$]-[$AA_2'$]-[$AA_3$]-[$AA_4$]-[$AA_5$], [$AA_1$]-[$AA_2$]-[$AA_3'$]-[$AA_4$]-[$AA_5$], [$AA_1$]-[$AA_2$]-[$AA_3$]-[$AA_4'$]-[$AA_5$] and [$AA_1$]-[$AA_2$]-$AA_3$]-[$AA_4$]-[$AA_5'$], wherein [AA'] is a naturally occurring or modified amino acid different from [AA]. In another aspect of the present invention, the peptide derivative has a sequence corresponding to a subsequence of the αD region of a PK, with the proviso that any two amino acid residues in the peptide derivative can differ from the corresponding amino acid residue in the subsequence.

An "amino acid residue" is a moiety found within a peptide and is represented by —NH—CHR—CO—, wherein R is the side chain of a naturally occurring amino acid. When referring to a moiety found within a peptide, the terms "amino acid residue" and "amino acid" are used interchangeably in this application. An "amino acid residue analog" includes D or L residues having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. When referring to a moiety found within a peptide, the terms "amino acid residue analog" and "amino acid analog" are used interchangeably in this application.

As used herein, aliphatic groups include straight chained, branched or cyclic C1–C8 hydrocarbons that are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F), —O (aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —CONH$_2$, —CONH (aliphatic, substituted aliphatic group, benzyl, substituted benzyl, aryl or substituted aryl group), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents.

Suitable substitutions for amino acid residues in the sequence of an αD region or a subsequence of an αD region include conservative substitutions which result in peptide derivatives which modulate the activity of a PK. A "conservative substitution" is a substitution in which the substituting amino acid (naturally occurring or modified) has about the same size and electronic properties as the amino acid being substituted. Thus, the substituting amino acid would have the same or a similar functional group in the side chain as the original amino acid.

A "conservative substitution" also refers to utilizing a substituting amino acid that is identical to the amino acid being substituted except that a functional group in the side chain is functionalized with a suitable protecting group. Suitable protecting groups are described in Green and Wuts, *"Protecting Groups in Organic Synthesis"*, John Wiley and Sons, Chapters 5 and 7, 1991, the teachings of which are incorporated herein by reference. As with N-terminal and C-terminal protecting group, preferred protecting groups are those which facilitate transport of the peptide into a cell, for example, by reducing the hydrophilicity and increasing the lipophilicity of the peptide, and which can be cleaved in vivo, either by hydrolysis or enzymatically, inside the cell. (Ditter et al., *J. Pharm. Sci.* 57:783 (1968); Ditter et al., *J. Pharm. Sci.* 57:828 (1968); Ditter et al., *J. Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., *Arch. Biochem. Biophys.* 239:538 (1985) and Singhal et al., *FASEB J.* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine, phenylalanine, serine, cysteine, threonine and modified amino acids having the following side chains: ethyl, n-butyl, —CH$_2$CH$_2$OH, —CH$_2$CH$_2$CH$_2$OH, —CH$_2$CHOHCH$_3$ and —CH$_2$SCH$_3$. Preferably, Group I includes leucine, isoleucine, valine and methionine.

Group II includes glycine, alanine, valine, serine, cysteine, threonine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —(CH$_2$)$_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, aspargine, methyl aspartate, ethyl aspartate, benzyl aspartate and methyl glutamate, ethyl glutamate and benzyl glutamate.

Group V includes histidine, lysine, arginine, N-nitroarginine, β-cycloarginine, β-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having C1–C5 straight or branched alkyl side chains substituted with —OH or —SH. Preferably, Group VI includes serine, cysteine or threonine.

In another aspect, suitable substitutions for amino acid residues in the sequence of an αD region or a subsequence of an αD region include "severe" substitutions which result in peptide derivatives which modulate the activity of a PK. Severe substitutions which result in peptide derivatives that modulate the activity of a PK are much more likely to be possible in positions which are not highly conserved throughout the family of protein kinases than at positions which are highly conserved. FIG. 2 shows the consensus sequences of the fifteen to forty amino acids of the αD region of PKs. Positions which are highly conserved among the PK family and the conserved amino acids generally found in those positions have been indicated. Because D-amino acids have a hydrogen at a position identical to the glycine hydrogen side-chain, D-amino acids or their analogs can often be substituted for glycine residues.

A "severe substitution" is a substitution in which the substituting amino acid (naturally occurring or modified) has significantly different size, configuration and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cycohexylmethyl glycine for alanine, isoleucine for glycine, a D amino acid for the corresponding L amino acid or —NH—CH[(—CH$_2$)$_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties from the functional group of the amino acid being substituted. Examples of such modifications include tryptophan for glycine, lysine for aspartic acid and —(CH$_2$)$_4$COOH for the side chain of serine. These examples are not meant to be limiting.

"Peptidomimetics" can be substituted for amino acid residues in the peptides of this invention. These peptidomimetics replace amino acid residues or act as spacer groups within the peptides. The peptidomimetics often have steric, electronic or configurational properties similar to the replaced amino acid residues but such similarities are not necessarily required. The only restriction on the use of peptidomimetics is that the peptides retain their protein kinase modulating activity. Peptidomimetics are often used to inhibit degradation of the peptides by enzymatic or other degradative processes. The peptidomimetics can be produced by organic synthetic techniques. Examples of suitable peptidomimetics include tetrazol (Zabrocki et al., *J. Am. Chem. Soc.* 110, 5875–5880 (1988)); isosteres of amide bonds (Jones et al., *Tetrahedron Lett.* 29, 3853–3856 (1988)); LL-3-amino-2-propenidone-6-carboxylic acid (LL-Acp) (Kemp et al., *J. Org. Chem.* 50, 5834–5838 (1985)). Similar analogs are shown in Kemp et al., *Tetrahedron Lett.* 29, 5081–5082 (1988) as well as Kemp et al., *Tetrahedron Lett.* 29, 5057–5060 (1988), Kemp et al., *Tetrahedron Lett.* 29, 4935–4938 (1988) and Kemp et al., *J. Org. Chem.* 54, 109–115 (1987). Other suitable peptidomimetics are shown in Nagai and Sato, *Tetrahedron Lett.* 26, 647–650 (1985); Di Maio et al., *J. Chem. Soc. Perkin Trans.,* 1687 (1985); Kahn et al., *Tetrahedron Lett.* 30, 2317 (1989); Olson et al., *J. Am. Chem. Soc.* 112, 323–333 (1990); Garvey et al., *J. Org. Chem.* 56, 436 (1990). Further suitable peptidomimetics include hydroxy-1,2,3,4-tetrahydroisoquinoline-3-carboxylate (Miyake et al., *J. Takeda Res. Labs* 43, 53–76 (1989)); 1,2,3,4-tetrahydroisoquinoline-3-carboxylate (Kazmierski et al., *J. Am. Chem. Soc.* 133, 2275–2283 (1991)); histidine isoquinolone carboxylic acid (HIC) (Zechel et al., *Int. J. Pep. Protein Res.* 43 (1991)); (2S, 3S)-methyl-phenylalanine, (2S, 3R)-methyl-phenylalanine, (2R, 3S)-methyl-phenylalanine and (2R, 3R)-methyl-phenylalanine (Kazmierski and Hruby, *Tetrahedron Lett.* (1991)).

The amino acid residues of the peptides can be modified by carboxymethylation, acylation, phosphorylation, glycosylation or fatty acylation. Ether bonds can be used to join the serine or threonine hydroxyl to the hydroxyl of a sugar. Amide bonds can be used to join the glutamate or aspartate carboxyl groups to an amino group on a sugar (Garg and Jeanloz, *Advances in Carbohydrate Chemistry and Biochemistry*, Vol. 43, Academic Press (1985); Kunz, *Ang. Chem. Int.* Ed. English 26, 294–308 (1987)). Acetal and ketal bonds can also be formed between amino acids and carbohydrates. Fatty acid acyl derivatives can be made, for example, by free amino group (e.g., lysine) acylation (Toth et al., *Peptides: Chemistry, Structure and Biology*, Rivier and Marshal, eds., ESCOM Publ., Leiden, 1078–1079 (1990)).

Examples of PKs whose activity can be modulated by peptide and peptide derivatives, as described herein, include, but are not limited to, PKs belonging to the following PK families: polo family (Glover et al., *J. Cell Biol.,* 135:1681 (1996)), Raf (Pritchard et al., *Nat. Genet.* 16:214 (July 1997)), mitogen-activate-protein kinases (MAP kinases), Akt/PKB (Frank et al., *Cell* 88:435 (1997) and Hemmings et al., *Science* 275:628 (1997)), G protein-coupled receptor kinases (Premont et al., *FASEB J.* 9:175 (February 1995)), Casein kinases, HGF receptors (Boros, *The Lancet* 345:293 (February 1995)), Cyclin-Dependent kinases, PDGF receptors, NGF receptors, Jak kinases, NFkB inhibitor kinases (Maniatis, *Science* 278:818 (October 1997)), Activin receptors, TGFβ receptors, Discoidin domain receptors (Vogel et al., *Molec. Cell. Biol.* 1:13 (December 1997)), Src, EGF-R, FGF-R, VEGF-R, HGF-R, PDGF-R, the insulin receptor family and the neurotrophin receptor family. Suitable members of the Polo family include, but are not limited to, Plk, Plx1, polo, SNK, CDC5, Sak, Prk, Fnk, Plo1. Suitable members of the Src family include, but are not limited to, c-Src, c-Yes, FYN, FGR, HCK, LYN, LCK and BLK. Suitable members of the EGF-R family include, but are not limited to EGFR, ErbB2, ErbB3 and ErbB4. Suitable members of the FGF-R family include, but are not limited to FGFR1, FGFR2, FGFR3 and FGFR4. Suitable members of the VEGF-R family include, but are not limited to, Flt1, Flt4 and Flk1. Suitable members of the insulin receptor family include, but are not limited to, INS-R, IRR and IGF1-R. Suitable members of the HGF receptor family include, but are not limited to, c-Met, c-Sea and Ron. Other suitable PKs include, but are not limited to, cyclic AMP (cAMP) dependent protein kinase, protein kinase C, calmodulin dependent kinase, glycogen synthase kinase-3 (GSK3) and cyclic GMP (cGMP) dependent protein kinase, RET (Pasini et al., *TIG* 12(4):138 (April 1996)), CSK, Matk, c-Abl, FAK (Frisch et al., *J. Cell. Biol.* 134(3):793 (August 1996)), MARK1, 2 and P78 (Drewes et al., *Cell* 89:297 (April 1997)), Tie and Tek, Syk and Zap70 (Arpaia et al., *Cell* 76:947 (1994)), Iak1, Chk1 (Sanchez et al., *Science* 277:1497 (September 1997)), DAPK, ILK (Hannigan et al., *Nature* 379:91 (January 1996)) and JNK.

As shown in FIG. 1, the sequences of suitable peptide members of the αD region of PKs from different families include, but are not limited to: c-Raf (SEQ ID NO:1); Araf (SEQ ID NO:2); Braf (SEQ ID NO:3); cyclic AMP dependent protein kinases a, b and g (cAPK) (SEQ ID NO:4 to 5); protein kinase C alpha through theta (PKC) (SEQ ID NO:6 to 12); Akt 1 and 2 (also called Rac α and β) (SEQ ID NO:13); glycogen synthase kinase α and β (GSK3) (SEQ ID NO:14 to 15); casein kinases type II α and α' (CK) (SEQ ID NO:16 to 17); G-receptor coupled protein kinases β-2 adrenergic receptor kinases 1 and 2 (bARK1, 2) (SEQ ID NO:18); G-protein coupled receptor kinases GRK1 and GRK4 through GRK6 (SEQ ID NO:19 to 22); calmodulin dependent kinases types I and II a, b, c and d (CaMK) (SEQ ID NO:23 to 24); members of the Polo-associated family: Plk, Plx1, polo, SNK, CDC5, Sak, Prk, Fnk, Plo1 (SEQ ID NO:25 to 32); MARK1 and MARK2 and p78 (SEQ ID NO:33 to 34); cyclin dependent kinases 2, 4 and 6 (SEQ ID NO:35 to 37); Src, Yes, Fyn, Fgr, Lyn, Hck, Lck (SEQ ID NO:38 to 44); Csk and Matk (SEQ ID NO:45 to 46); focal adhesion kinase (FAK) (SEQ ID NO:47); c-Abl (SEQ ID NO:48); endothelial growth factor receptors Tie, Tek, FGF receptor (Flg, Bek, FGFR3, FGFR4), PDGF receptor α and β, Flt 1 and 4 and Flk1 (SEQ ID NO:49 to 59); HGF receptors c-Met, c-Sea and Ron (SEQ ID NO:60 to 62); EGF receptor (EGFR, ErbB2, ErbB3, ErbB4) (SEQ ID NO:63 to 66); Ret (SEQ ID NO:67); NGF receptors (Trk) (SEQ ID NO:68 to 70); Syk and Zap70 (SEQ ID NO:71 to 72); Jak kinases 1 through 3 and Tyk2 (SEQ ID NO:73 to 76); Iak1 (SEQ ID NO:77); Chk1 (SEQ ID NO:78); NFkB inhibitor kinases IKK1 and IKK2 (SEQ ID NO:79 to 80); death associated protein kinase (DAPK) (SEQ ID NO:81); insulin receptor kinase (IRK) (SEQ ID NO:82); TGFβ receptor type II (SEQ ID NO:83); Activin receptor type II A and B (ACTR) (SEQ ID NO:84 to 85); Activin receptor-like kinases 1 through 6 (ALK1, 2, 3, 4, 5, 6) (SEQ ID NO:86 to 90); discoidin domain receptor 1 (DDR) and Tyro10 (SEQ ID NO:91 to 92); ILK (SEQ ID NO:93); Jun kinase (JNK) (SEQ ID NO:94).

The amino acid at the N-terminus of the αD region is at position 1 and can be referred to as "$[AA]_1$". The next amino acid in the sequence, referred to as "$[AA]_2$", is at position 2 and is followed by amino acids $[AA]_3$ through $[AA]_m$, which are at positions 3 to m, where m is the position number of the amino acid at the C-terminus of the αD region. Likewise, (m-12) is the position number of the amino acid twelve amino acid residues before the C-terminus of the αD region. Thus, a peptide 20-mer with an amino acid sequence $[AA]_1$ through $[AA]_{20}$ includes the first twenty amino acids in the αD region. A peptide derivative of the αD region with an amino acid sequence $[AA]_5$ through $[AA]_{16}$ includes the fifth amino acid through the sixteenth amino acid in the αD region, and a peptide derivative of the αD region with an amino acid sequence $[AA]_{(m-12)}$ through $[AA]_m$ includes the last twelve amino acids in the αD region. In this invention, m can have a value between 15 and 45.

The present invention includes peptides having amino acid sequences corresponding to the sequence found in the αD region of PKs, subsequences thereof and modified subsequences thereof. Examples of suitable subsequences include, but are not limited to, sequences corresponding to $[AA]_1$ through $[AA]_m$, $[AA]_1$ through $[AA]_{12}$, $[AA]_5$ through $[AA]_{16}$, $[AA]_9$ through $[AA]_{20}$, $[AA]_{(m-12)}$ through $[AA]_m$, $[AA]_{(m-12)}$ through $[AA]_{(m-2)}$ and $[AA]_{(m-20)}$ through $[AA]_{(m-8)}$ of the αD region of a PK, and subsequences thereof. The above designated sequences are preferred.

The present invention includes peptides having amino acid sequences corresponding to a modified sequence or subsequence of the αD region of PKs and which modulate the activity of PKs including: Akt1/Raca; ALK1; Braf; c-Abl; c-Met; c-Raf; c-Sea; c-Src; CDK2; CDK4; CDK6; Chk1; CK IIa; Csk; Fak; FGFR-3; Flk1; GSK3b; Hck; Iak1; IKK-1; IKK2; ILK; IRK; Jak1; Jak2; Jak3; Lck; Lyn; MARK1; PDGFR-b; PKCb; Plk; Ret; Ron; SNK; Syk; TGFβRII; TrkB; and Zap70.

In one aspect, one, two or more of the amino acids in the sequence or subsequence are modified with conservative substitutions; the substitutions can be in consensus positions, in non-consensus positions or in both. In another aspect, one, two or more of the amino acids in the sequence or subsequence are modified with severe substitutions; the substitutions are preferably in non-consensus positions. FIGS. 2A–2F provides examples of conservative amino acid substitutions for the αD region of:

c-Raf (SEQ ID NO:1); Araf (SEQ ID NO:2); Braf (SEQ ID NO:3); cyclic AMP dependent protein kinases a, b and g (cAPK) (SEQ ID NO:4 to 5); protein kinase C alpha through theta (PKC) (SEQ ID NO:6 to 12); Akt 1 and 2 (also called Rac α and β) (SEQ ID NO:13); glycogen synthase kinase α and β (GSK3) (SEQ ID NO:14 to 15); casein kinases type II α and α' (CK) (SEQ ID NO:16 to 17); G-receptor coupled protein kinases β-2 adrenergic receptor kinases 1 and 2 (bARK1, 2) (SEQ ID NO:18); G-protein coupled receptor kinases GRK1 and GRK4 through GRK6 (SEQ ID NO:19 to 22); calmodulin dependent kinases types I and II a, b, c and d (CaMK) (SEQ ID NO:23 to 24); members of the Polo-associated family: Plk, Plx1, polo, SNK, CDC5, Sak, Prk, Fnk, Plo1 (SEQ ID NO:25 to 32); MARK1 and MARK2 and p78 (SEQ ID NO:33 to 34); cyclin dependent kinases 2, 4 and 6 (SEQ ID NO:35 to 37); Src, Yes, Fyn, Fgr, Lyn, Hck, Lck (SEQ ID NO:38 to 44); Csk and Matk (SEQ ID NO:45 to 46); focal adhesion kinase (FAK) (SEQ ID NO:47); c-Abl (SEQ ID NO:48); endothelial growth factor receptors Tie, Tek, FGF receptor (Flg, Bek, FGFR3, FGFR4), PDGF receptor α and β Flt 1 and 4 and Flk1 (SEQ ID NO:49 to 59); HGF receptors c-Met, c-Sea and Ron (SEQ ID NO:60 to 62); EGF receptor (EGFR, ErbB2, ErbB3, ErbB4) (SEQ ID NO:63 to 66); Ret (SEQ ID NO:67); NGF receptors (Trk) (SEQ ID NO:68 to 70); Syk and Zap70 (SEQ ID NO:71 to 72); Jak kinases 1 through 3 and Tyk2 (SEQ ID NO:73 to 76); Iak1 (SEQ ID NO:77); Chk1 (SEQ ID NO:78); NFkB inhibitor kinases IKK1 and IKK2 (SEQ ID NO:79 to 80); death associated protein kinase (DAPK) (SEQ ID NO:81); insulin receptor kinase (IRK) (SEQ ID NO:82); TGFβreceptor type II (SEQ ID NO:83); Activin receptor type II A and B (ACTR) (SEQ ID NO:84 to 85); Activin receptor-like kinases 1 through 6 (ALK1, 2, 3, 4, 5, 6) (SEQ ID NO:86 to 90); discoidin domain receptor 1 (DDR) and Tyro10 (SEQ ID NO:91 to 92); ILK (SEQ ID NO:93); Jun kinase (JNK) (SEQ ID NO:94). The conservative substitutions can occur by exchanging amino acids with aligned αD region sequences, as shown in FIGS. 2A–2F, as well as by substituting the listed amino acids that are not associated with a known αD region sequence.

Specific examples of peptide derivatives of the present invention include peptides: Akt1/Raca K014D001; ALK1 K048D101; Braf K003D001 K003D101; c-Abl K061D101; c-Met K073D101; c-Raf K001D101 K001D001; c-Sea K074D101; c-Src K051D101 K051D001; CDK2 K049D101 K049D001; CDK4 K050D001 K050D101; CDK6 K089D101; Chk1 K088D102 K088D101; CK IIα K022D001 K022D101; Csk K058D101 K058D001; Fak K060D101; FGFR-3 K071D101 K071D001 K071D102 K071D901; Flk1 K068D102 K068D101 K068D001 K068d901; GSK3β K018D003 K018D002 K018D101 K018D001; Hck K056D101; Iak1 K087D101; IKK-1 K090D101; IKK2 K091D101; ILK K107D101 K107D901; IRK K094D001 K094D101 K094D102 K094D103 K094D104; Jak1 K084D101K084D102; Jak2 K085D102 K085D105; Jak3 K086D101 K086D102 K086D103; Lck K057D001 K057D101; Lyn K055D101; MARK1 K045D101; PDGFR-b K064D001 K064D101; PKCβ K008D101 K008D001; Plk K035D001 K035D101 K035D102; Ret K080D101 K080D001; Ron K075D101; SNK K038D101; Syk K082D101; TGFβRII K093D101; TrkB K102D101 K102D106 K102D107 K102D108 K102D109; Zap70 K083D101 (SEQ ID NO:95 to 170, respectively), as specified in FIGS. 3A–3D.

The N-terminus and/or C-terminus of these peptides can be modified, as described above and as shown in FIGS. 3A–3D. The N-terminal of these peptides is acetylated, stearylated or myristylated and the C-terminal is amidated. Other protecting groups for amides and carboxylic acids can be used, as described above. Optionally, one or both protecting groups can be omitted. The peptides may be linear or cyclic.

Also included are peptides having the sequence of: Akt1/Raca K014D001; ALK1 K048D101; Braf K003D001 K003D101; c-Abl K061D101; c-Met K073D101; c-Raf K001D101 K001D001; c-Sea K074D101; c-Src K051D101 K051D001; CDK2 K049D101 K049D001; CDK4 K050D001 K050D101; CDK6 K089D101; Chk1 K088D102 K088D101; CK IIα K022D001 K022D101; Csk K058D101 K058D001; Fak K060D101; FGFR-3 K071D101 K071D001 K071D102 K071D901; Flk1 K068D102 K068D101 K068D001 K068d901; GSK3β K018D003 K018D002 K018D101 K018D001; Hck K056D101; Iak1 K087D101; IKK-1 K090D101; IKK2 K091D101; ILK K107D101 K107D901; IRK K094D001 K094D101 K094D102 K094D103 K094D104; Jak1 K084D101 K084D102; Jak2 K085D102 K085D105; Jak3 K086D101 K086D102 K086D103; Lck K057D001 K057D101; Lyn K055D101; MARK1 K045D101; PDGFR-b K064D001K064D101; PKCβ K008D101 K008D001; Plk K035D001 K035D101 K035D102; Ret K080D101 K080D001; Ron K075D101; SNK K038D101; Syk K082D101; TGFβRII K093D101; TrkB K102D101 K102D106 K102D107 K102D108 K102D109; Zap70 K083D101 (SEQ ID NO:95 to 170, respectively), as specified in FIGS. 3A–3D, with the proviso that any one or two of the amino residues in the peptide can vary, being replaced by any naturally occurring amino acid or analog thereof.

The present invention also includes cyclic peptides having amino acid sequences corresponding to a modified sequence or subsequence of the αD region of PKs. These cyclic peptides modulate the activity of PKs.

A "cyclic peptide" refers, for example, to a peptide or peptide derivative in which a ring is formed by the formation of a peptide bond between the nitrogen atom at the N-terminus and the carbonyl carbon at the C-terminus.

"Cyclized" also refers to the forming of a ring by a covalent bond between the nitrogen at the N-terminus of the compound and the side chain of a suitable amino acid in the peptide, preferably the side chain of the C-terminal amino acid. For example, an amide can be formed between the nitrogen atom at the N-terminus and the carbonyl carbon in the side chain of an aspartic acid or a glutamic acid. Alternatively, the peptide or peptide derivative can be cyclized by forming a covalent bond between the carbonyl at the C-terminus of the compound and the side chain of a suitable amino acid in the peptide, preferably the chain of the N-terminal amino acid. For example, an amide can be formed between the carbonyl carbon at the C-terminus and the amino nitrogen atom in the side chain of a lysine or an ornithine. Additionally, the peptide or peptide derivative can be cyclized by forming an ester between the carbonyl carbon at the C-terminus and the hydroxyl oxygen atom in the side chain of a serine or a threonine.

"Cyclized" also refers to forming a ring by a covalent bond between the side chains of two suitable amino acids in the peptide, preferably the side chains of the two terminal amino acids. For example, a disulfide can be formed between the sulfur atoms in the side chains of two cysteines. Alternatively, an ester can be formed between the carbonyl carbon in the side chain of, for example, a glutamic acid or an aspartic acid, and the oxygen atom in the side chain of, for example, a serine or a threonine. An amide can be formed between the carbonyl carbon in the side chain of, for example, a glutamic acid or an aspartic acid, and the amino nitrogen in side chain of, for example, a lysine or an ornithine.

In addition, a peptide or peptide derivative can be cyclized with a linking group between the two termini, between one terminus and the side chain of an amino acid in the peptide or peptide derivative, or between the side chains to two amino acids in the peptide or peptide derivative. Suitable linking groups are disclosed in Lobl et al., WO 92/00995 and Chiang et al., WO 94/15958, the teachings of which are incorporated into this application by reference.

Suitable substitutions in the original amino acid sequence or subsequence are those which result in a peptide derivative, as defined above, which modulates the activity of a PK. The activity of a PK is "modulated" when the activity of the PK is increased or decreased. An increase or decrease in the activity of a PK can be detected by assessing in vitro the extent of phosphorylation of a protein substrate of the PK being tested or by a corresponding modulation, increase or decrease, in a cellular activity or function which is under the control of the PK. Examples of these cellular functions include cell proliferation, cell differentiation, cell morphology, cell survival or apoptosis, cell response to external stimuli, gene expression, lipid metabolism, glycogen or glucose metabolism and mitosis.

It can be readily determined whether a peptide or peptide derivative modulates the activity of a PK by incubating the peptide or peptide derivative with cells which have one or more cellular activities controlled by a PK. The cells are incubated with the peptide or peptide derivative to produce a test mixture under conditions suitable for assessing the activity of the protein kinase. The activity of the PK is assessed and compared with a suitable control, e.g., the activity of the same cells incubated under the same conditions in the absence of the peptide or peptide derivative. A greater or lesser activity of the PK in the test mixture compared with the control indicates that the test peptide or peptide derivative modulates the activity of the PK.

Suitable cells for the assay include normal cells which express a membrane bound or intracellular PK, cells which have been genetically engineered to express a PK, malignant cells expressing a PK or immortalized cells which express a PK.

Conditions suitable for assessing PK activity include conditions suitable for assessing a cellular activity or function under control of the PK. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors).

In another aspect, the activity of certain PK (e.g., Atk/PKB, Dudek et al., *Science* 275:661 (1997)) can be evaluated by growing the cells under serum deprivation conditions. Cells are typically grown in culture in the presence of a serum such as bovine serum, horse serum or fetal calf serum. Many cells, for example, nerve cells such as PC-12 cells, generally do not survive with insufficient serum. The use of insufficient serum to culture cells is referred to as "serum deprivation conditions" and includes, for example, from 0% to about 4% serum. PK activity is determined by the extent to which a peptide or peptide derivative can protect cells, e.g., neuronal cells, from the consequences of serum deprivation. Specific conditions are provided in Dudek et al., and in Example 4 of co-pending and concurrently filed application entitled "SHORT PEPTIDES WHICH SELECTIVELY MODULATE INTRACELLULAR SIGNALLING" (filed on May 21, 1997, U.S. application Ser. No. 08/861,153), the teachings of which are incorporated herein by reference.

Generally, the activity of the PK in the test mixture is assessed by making a quantitative measure of the cellular activity which the PK controls. The cellular activity can be, for example, cell proliferation. Examples of cells in which proliferation is controlled by a PK include endothelial cells such as bovine aortic cells, mouse MSI cells or mouse SVR cells (see Arbiser et al., *Proc. Natl. Acad. Sci. USA* 94:861 (1997)), vascular smooth muscle cells, and malignant cells of various tissues such as breast cancer, lung cancer, colon cancer, prostate cancer or melanoma. PK activity is assessed by measuring cellular proliferation, for example, by comparing the number of cells present after a given period of time with the number of cells originally present. One example of PKs having to do with cellular proliferation is the polo family and the CDKs.

Specific examples of conditions suitable for determining the activity of PKs by assessing cell proliferation are provided in Example 2.

If cells are being used in which the PK controls cell differentiation (e.g., preadipocytes such as 3T3-L1 expressing PKs Akt/PKB, GSK3 and protein kinase A—see Kohn et al., *J. Biol. Chem.* 271:31372 (1996)), activity is assessed by measuring the degree of differentiation. Activity can be assessed by changes in the metabolic activity of cells such as primary adipocytes, hepatocytes and fibroblasts by measuring changes in glucose uptake, lipogenesis, or glycogen metabolism (see, for example, Weise et al., *J. Biol. Chem.* 270:3442 (1995)). Activity can also be assessed by the extent to which gene expression, cell morphology or cellular phenotype is altered (e.g., the degree to which cell shape is altered or the degree to which the cells assume a spindle-like structure). One example of a change in cellular morphology is reported in the co-pending and concurrently filed application entitled "SHORT PEPTIDES WHICH SELECTIVELY MODULATE INTRACELLULAR SIGNALLING" (filed on May 21, 1997, U.S. application Ser. No. 08/861,153), which discloses that certain peptide derivatives of the HJ loop of protein tyrosine kinases can cause vascular smooth muscle cells to become elongated and assume a spindle-like shape.

It is to be understood that the assay described hereinabove for determining whether a peptide or peptide derivative modulates a cellular activity or function under the control of a PK can be performed with cells other than those specifically described herein. PKs not yet discovered or PKs whose function is not yet known can also be used in this assay, once it has been determined which cellular functions or activities they control. These PKs are also within the scope of the present invention.

The present invention is also directed to a method of modulating the activity of a protein kinase in a subject. A "subject" is preferably a human, but can also be animals in need of treatment, e.g., veterinary animals (e.g., dogs, cats, and the like), farm animals (e.g., cows, pigs, horses and the like) and laboratory animals (e.g., rats, mice, guinea pigs and the like).

The activity of a PK in a subject can be modulated for the purpose of treating diseases that are caused by over activity or under activity of PKs. For example, MAP kinases (Seger and Krebs, *FASEB J.* 9:726 (1995)) and cyclin dependent protein kinases ("Molecular Biology of the Cell," Alberts, Bray, Lewis, Raff, Roberts and Watson, eds. Chapter 5, (Garland Publishing, Inc.), (1994)), are central components of the cell-division cycle control system in eukaryotic cells. Other PKs, for example, protein kinase C and Raf kinases (Nishizuka, *The FASEB Journal* 9:484 (1995), Locric, et al., *Oncogene* 12:1109 (1996) and Laird et al., *J. Biol. Chem.* 270:26,742 (1995)) are, in turn, involved in the control of MAP kinases or are activated during mitosis. The G protein-coupled receptor kinases (GRKs), on the other hand, desensitize the receptors and are thereby involved in the regulation of various hormonal responses (Freedman and Lefkowitz, *Recent Prog. Hormon. Res.* 51:319 (1996). Activation of Akt/PKB is implicated in the inhibition of apoptosis, i.e., programmed cell death (Frank et al., *Cell* 88:435 (1997) and Hemmings *Science* 275:628 (1997)). Peptides and peptide derivatives of the present invention which modulate the activity of these enzymes can be used to treat cancer in a subject when administered to the subject in a therapeutically effective amount.

c-AMP dependent kinase, GSK3 and Akt/PKB are involved in the control of glycogen metabolism. Peptide and peptide derivatives of the present invention which modulate the activity of cAMP dependent kinase can be used to treat Type II diabetes and hemorrhagic shock in a subject when administered to the subject in a therapeutically effective amount. cAMP derivatives have also been reported to inhibit the growth of human cancer cells (Katsros et al., *FEBS Lett.* 223:97 (1987)), indicating that inhibitors of cAMP dependent kinases can also be useful in the treatment of cancer.

Raf kinases are involved in the control of lipid metabolism. Peptide and peptide derivatives of the present invention which modulate the activity of Raf kinases can be used to treat obesity in a subject when administered to the subject in a therapeutically effective amount.

Agents which modulate the activity of protein kinase C can be used to treat a wide variety of other disease conditions, including cardiovascular diseases (e.g., thrombosis, atherosclerosis, arteriosclerosis, cardiac hypertrophy, ischemia, reperfusion injury and hypertension), immunosuppressive and inflammatory disorders (e.g., asthma, psoriasis, systemic lupus erythematous, diabetes mellitus, suppression of organ transplant rejection, multiple sclerosis, inflammatory bowel disease and AIDS), central nervous system diseases (e.g., Alzheimer's disease, stroke and trauma), septic shock based on protein kinase C activation and ischemia induced renal failure (Nambi, WO 93/16703, Bradshaw, et al., *Agents Action* 38:135 (1993) and Birchall et al., *The J. Pharm. and Exper. Therapeut.* 2:922 (1994)). Peptide and peptide derivatives of the present invention which modulate the activity of protein kinase C can be used to treat these diseases in a subject when administered to the subject in a therapeutically effective amount.

Phosphorylation by G-protein receptor kinases are known (Freedman and Lefkowitz, *Recent Prog. Hormon. Res.* 51:319 (1996)) to result in receptor desensitization, thereby extending the duration of hormonal effects of, for example, adrenalin. Thus, agents which modulate the activity of G-protein receptor kinases can be used in the treatment of disease resulting from a lower bioavailability of the corresponding ligand, such as dopamine. Inhibitors of calmodulin dependent kinases have been reported to inhibit dopamine release (Nagatsu et al., *Biochem. Biophys. Research, Commun.* 143:1045 (1987)). Thus, agents which modulate the activity of G-protein receptor kinases and calmodulin receptor kinases can be useful in the treatment of diseases involving dysfunction of dopamine signalling, for example, Parkinson's Disease. Inhibitors of calmodulin dependent kinases have also been reported to relax arterial muscle (Saitoh et al., *J. Bio. Chem.* 262:7796 (1987)) and therefore can be used in treating hypertension. Inhibition of GSK3 might increase the intracellular activity of the insulin receptor and thereby enhance glucose uptake and other related metabolic activities. Thus, agents which modulate the activity of GSK3 can be useful in the treatment of Type I and Type II diabetes.

Cancer can be treated by anti-angiogenic therapies. Inhibition of c-Met or tyrosine kinase receptors which respond to fibroblast growth factor (FGF), or vascular endothelial growth factor (VEGF) decreases angiogenesis. As a result, cancers can be treated by administering a therapeutically effective amount of a peptide or peptide derivative of the present invention which results in decreased activity of c-Met or tyrosine kinase receptors which respond to FGF or VEGF. In addition, RET is involved in certain thyroid cancers; therapeutically effective amounts of peptides or peptide derivatives of the present invention which modulate the activity of RET can be used to treat these thyroid cancers. Restenosis is caused by vascular smooth muscle proliferation in response to, for example, vascular injury caused by balloon catheterization. Vascular smooth muscle proliferation is also a cause of arteriosclerosis. Vascular smooth muscle proliferation is a result of, for example, inhibition of Csk and/or stimulation of tyrosine kinase receptors which respond to FGF or platelet derived growth factor (PDGF). Thus, restenosis and arteriosclerosis can be treated with a therapeutically effective amount of a peptide or peptide derivative of the present invention which inhibits tyrosine kinase receptors which respond to FGF or PDGF or which activate Csk.

FGF has also been implicated in psoriasis, arthritis and benign prostatic hypertrophy (Dionne et al., WO 92/00999). These conditions can be treated with αD peptides from PKs which respond to FGF.

Src activity is responsible, at least in part, for bone resorption. Thus, osteoporosis can be treated with a therapeutically effective amount of a peptide or peptide derivative of the present invention which inhibits Src activity or which activates Csk.

Lyn and Hck are activated during the non-specific immune response which occurs in individuals with arthritis which occurs in individuals as a result of allergic responses. Lyn is also activated in individuals with septic shock. Thus, these conditions can be treated with a therapeutically effective amount of a peptide or peptide derivative of the present invention which inhibits the activity of these PKs.

Lck, Jak1 and Jak3 are expressed in T cells and are activated during a T cell immune response. Similarly, Lyn is expressed in B cells and activated during a B cell immune response. Thus, conditions which are caused by overactivation of T cells or B cells can be treated by administering a therapeutically effective amount of a peptide or peptide derivative of the present invention which inhibits Lck, Jak1, Jak3 or Lyn, respectively. Conditions which are caused by underactivation of T cells or B cells can be treated by administering a therapeutically effective amount of a peptide or peptide derivative of the present invention which stimulates Lck, Jak1, Jak3 or Lyn, respectively.

For example, it is now known that functionally polarized responses are displayed by two subpopulations of CD4+ T cells, named Th1 and Th2. Th1 cells produce interferon γ (IFNγ and tumor necrosis factor β (TNFβ). Th2 cells produce interleukins 4,5,10 and 13 (IL-4, IL-5, IL-10 and IL-13). Thus, Th1 responses are beneficial for protection against intracellular parasites and can aid tumor immunity. Th2, on the other hand, is responsible for strong antibody responses. Several diseases are associated with an overexpression of Th1 or Th2 cells. Examples include Th1 responses which predominate in organ-specific autoimmune diseases, and Th2 responses which are responsible for triggering allergic reactions, including IgE production.

Many of the cytokines involved in Th1/Th2 maturation mediate their signaling through members of the Jak family of intracellular kinases; e.g., IL-4 responses are mediated via Jak1 and Jak3, IFNγ signals are mediated via Jak1 and Jak2. Therefore, a manipulation of the activity of members of the Jak family by αD region derived peptides can modulate Th1/Th2 activities and help boost desired immune responses or aid in alternating pathological responses.

A severe reduction of the B cell progenitor kinase leads to human X-linked agammaglobulinemia, which can be treated by administering a therapeutically effective amount of a peptide or peptide derivative of the present invention which stimulates B cell progenitor kinase. Decreased function of other PKs can also lead to disease. For example, a decrease in the activity of insulin receptor tyrosine kinase (IRK) is a cause of various types of diabetes. These types of diabetes can be treated by administering a therapeutically effective amount of a peptide or peptide derivative of the present invention which increases the activity of IRK. In addition, the viability and proper function of neurons depend on signaling by neurotrophic factors. TrkB, in particular, is implicated in signal transduction of BDNF. Thus, peptides of this invention that can enhance TrkB kinase activity will be beneficial for a variety of CNS disorders.

Another family of transmembrane protein kinases is composed of members of the TGFβ/Activin/BMP receptors which transduce signals of the corresponding cytokines. The TGFβ Activin/BMP cytokines participate in processes such as tissue repair, including the induction of bone formation. Therefore, modulation of the activity of these receptor kinases can assist tissue repair, inhibit tissue fibrosis and enhance bone formation.

Based on methods disclosed herein, peptides and peptide derivatives can be designed to modulate the activity of PKs whose αD region has been sequenced or will be sequenced in the future and whose cellular function is known. As a consequence, peptides and peptide derivatives can be designed to affect (increase or decrease) those cellular functions. It is possible that future research will reveal that certain disease conditions, whose underlying causes are presently unknown, are brought about by the overactivity or underactivity of cellular functions controlled by these PKs. These diseases can be treated by administering peptides which are peptide derivatives of the αD region of the overactive or underactive PK. Suitable peptides and peptide derivatives can be identified by methods disclosed herein. These methods of treatment, peptides and peptide derivatives are encompassed within the scope of the present invention.

A "therapeutically effective amount" is the quantity of compound which results in an improved clinical outcome as a result of the treatment compared with a typical clinical outcome in the absence of the treatment. An "improved clinical outcome" results in the individual with the disease experiencing fewer symptoms or complications of the disease, including a longer life expectancy, as a result of the treatment. With respect to cancer, an "improved clinical outcome" includes a longer life expectancy. It can also include slowing or arresting the rate of growth of a tumor, causing a shrinkage in the size of the tumor, a decreased rate of metastasis and/or improved quality of life (e.g., a decrease in physical discomfort or an increase in mobility).

With respect to diabetes, an improved clinical outcome refers to a longer life expectancy, a reduction in the complications of the disease (e.g., neuropathy, retinopathy, nephropathy and degeneration of blood vessels) and an improved quality of life, as described above.

With respect to obesity, an improved clinical outcome refers to increased weight reduction per caloric intake or a reduction in food intake. It also refers to a decrease in the complications which are a consequence of obesity, for example heart disease such as arteriosclerosis and high blood pressure.

The amount of peptide or peptide derivative administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the peptide or peptide derivative can range from about 1 mg per day to about 1000 mg per day for an adult. Preferably, the dosage ranges from about 1 mg per day to about 100 mg per day.

The peptide and peptide derivatives of the present invention are preferably administered parenterally. Parenteral administration can include, for example, systemic administration, such as by intramuscular, intravenous, subcutaneous, or intraperitoneal injection. Peptides or peptide derivatives which resist proteolysis can be administered orally, for example, in capsules, suspensions or tablets. The peptide or peptide derivative can also be administered by inhalation or insufflation or via a nasal spray.

The peptide or peptide derivative can be administered to the individual in conjunction with an acceptable pharmaceutical carrier as part of a pharmaceutical composition for treating the diseases discussed above. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., *Controlled Release of Biological Active Agents*, John Wiley and Sons, 1986).

The peptide and peptide derivatives of the present invention have many utilities other than as a therapeutic agent. Some of these uses are discussed in the following paragraphs.

The αD region peptides of the present invention are derived from an array which is linear in the native protein. These peptides can be useful in the preparation of specific antibodies against PKs. Moreover, since the αD region sequence is unique to each sub-family of PK, anti-αD region antibodies can be specifically used to isolate distinct sub-families of PK.

Suitable antibodies can be raised against an αD region peptide by conjugating the peptide to a suitable carrier, such as keyhole limpet hemocyanin or serum albumin; polyclonal and monoclonal antibody production can be performed using any suitable technique. A variety of methods have been described (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer 1994), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Antibodies, including monoclonal antibodies, against αD region peptides have a variety of uses. For example, those against or reactive with the protein from which the αD peptides was derived, and preferably which bind specifically to said protein, can be used to identify and/or sort cells exhibiting that protein on the cell surface (e.g., by means of fluorescence activated cell sorting or histological analyses). Monoclonal antibodies specific for the protein can also be used to detect and/or quantitate the protein expressed on the surface of a cell or present in a sample (e.g., in an ELISA). Alternatively, the antibodies can be used to determine if an intracellular PK is present in the cytoplasm of the cell. A lysate of the cell is generated (for example, by treating the cells with sodium hydroxide (0.2 N) and sodium dodecyl sulfate (1%) or with a non-ionic detergent like NP-40, centrifugating and separating the supernatant from the pellet), and treated with anti-αD region antibody specific for the PK. The lysate is then analyzed, for example, by Western blotting or immunoprecipitation for complexes between PK and antibody. Some PKs become membrane-bound or cytoskeleton-associated following stimulation. Anti-αD region antibodies can be utilized for the study of the intracellular distribution (compartmentalization) of various sub-families of PKs under various physiological conditions via the application of conventional immunocytochemistry such as immunofluorescence, immunoperoxidase technique and immunoelectron microscopy, in conjunction with the specific anti-αD region antibody.

Antibodies reactive with the αD region are also useful to detect and/or quantitate the PK or αD peptide in a sample, or to purify the PK from which the αD region was derived (e.g., by immunoaffinity purification).

The αD region within PKs plays a key role in regulating the activity of PKs, as is evidenced by the fact that the peptides and peptide derivatives of the present invention have such a dramatic effect on the activity of PKs. The αD region peptides of the present invention can also be used to identify ligands which interact with the αD regions of specific PKs and which modulate the activity PKs. For example, an affinity column can be prepared to which a specific αD region peptide is covalently attached, directly or via a linker. This column, in turn, can be utilized for the isolation and identification of specific ligands which bind the αD region peptide and which will also likely bind the PK from which the αD region peptide was derived. The ligand can then be eluted from the column, characterized and tested for its ability to modulate PK function.

Peptide sequences in the compounds of the present invention may be synthesized by solid phase peptide synthesis (e.g., t-BOC or F-MOC) method, by solution phase synthesis, or by other suitable techniques including combinations of the foregoing methods. The t-BOC and F-MOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48–267; and Barany and Merrifield, in *The Peptides*, E. Gross and J. Meienhofer, Eds., Academic Press, New York, 1980, pp. 3–285. Methods of solid phase peptide synthesis are described in Merrifield, R. B., *Science,* 232: 341 (1986); Carpino, L. A. and Han, G. Y., *J. Org. Chem.*, 37: 3404 (1972); and Gauspohl, H. et al., *Synthesis*, 5: 315 (1992)). The teachings of these references are incorporated herein by reference.

Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protecting groups such as allyl (OAI) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAI and Aloc are easily removed by Pd and Acm is easily removed by iodine treatment.

The invention is illustrated by the following examples which are not intended to be limiting in any way.

EXAMPLE 1

Preparation of Ad Peptides

The novel compounds of this invention can be synthesized utilizing a 430A Peptide Synthesizer from Applied Biosystems using F-Moc technology according to manufacturer's protocols. Other suitable methodologies for preparing peptides are known to person skilled in the art. See, e.g., Merrifield, R. B., *Science,* 232: 341 (1986); Carpino, L. A., Han, G. Y., *J. Org. Chem.*, 37: 3404 (1972); Gauspohl, H., et al., *Synthesis,* 5: 315 (1992)), the teachings of which are incorporated herein by reference.

Rink Amide Resin [4(2',4' Dimethoxyphenyl-FMOC amino methyl) phenoxy resin] was used for the synthesis of C-amidated peptides. The alpha-amino group of the amino acid was protected by an FMOC group, which was removed at the of each cycle by a weak base, 20% piperidine in N-methylpyrrolidone (NMP). After deprotection, the resin was washed with NMP to remove the piperidine. In situ activation of the amino acid derivative was performed by the FASTMOC Chemistry using HBTU (2(1-benzotriazolyl-1-yl)-1,1,3,3-tetramethyluronium) dissolved in HOBt (1-hydroxybenzotriazole) and DMF (dimethylformamide). The amino acid was dissolved in this solution with additional NMP. DIEA (diisopropylethylamine) was added to initiate activation. Alternatively, the activation method of DCC (dicyclohexylcarbodiimide) and HOBt was utilized to form an HOBt active ester. Coupling was performed in NMP. Following acetylation of the N-terminus (optional), TFA (trifluoroacetic acid) cleavage procedure of the peptide from the resin and the side chain protecting groups was applied using 0.75 g crystalline phenol; 0.25 ml EDT (1,2-ethandithiol); 0.5 ml thioanisole; 0.5 ml D.I. $H_2O$; 10 ml TFA.

EXAMPLE 2

αD Peptide Derivatives of Jak3 Modulate Proliferation of Endothelial Cells in vitro Human endothelial cells (referred to herein as "HEC cells") are the cell line described by Schweitzer et al., *Laboratory Investigation* 76(1):25 (1997). Human prostate cancer cells (PC3) were obtained by the procedures disclosed in Arbiser et al., *Proc. Natl. Acad. Sci.* 94:861 (1997), the teachings of which are incorporated herein by reference.

96 well, flat bottom, tissue culture microtiter plates were pre-coated with gelatin (Difco) immediately prior to cell plating by adding 0.100 ml/well of freshly filtered 1% gelatin in glass double distilled water (DDW). The wells were incubated for about 1 hour at 37° C., and then the excess solution was removed by aspiration.

Culture medium was prepared from DMEM, penicillin/streptomycin/glutamine (penicillin—100 U/ml; streptomycin—100 µg/mL; and glutamine—2 mM) and 10% endotoxin free bovine calf serum (Hyclone). A suspension of the cell type being tested at $25 \times 10^3$ cells/ml was prepared in the above described culture medium and distributed 0.160 ml/well (about 4000 endothelial cells/well).

A series of αD peptide stock solutions was prepared by diluting a 10 mM solution of the αD peptide in 100% DMSO with phosphate buffered saline (PBS) containing 0.1% BSA. The concentration of αD peptide in each stock solution was adjusted to nine times the desired concentration of the αD peptide in the assay mixture.

0.020 ml of each αD peptide stock solution was added to the corresponding wells about 2 hours after cell plating, with six replicates for each concentration. In addition, BSA solution with no added αD peptide was used as a control. The wells were incubated for 72–80 hours at 37° C. in a 10% $CO_2$ humidified incubator.

The plates were labeled and the medium discarded. Each plate was then washed one time with PBS (0.200 ml/well). The wells were then fixed by washing with 100% ethanol (0.200 ml/well for 5 minutes). The ethanol was removed and the wells dried completely. Alternatively, the wells were fixed with 4% formaldehyde PBS (PBS buffered 10% formalin from Fisher Scientific; Catalog No. HC200-1) (0.12 ml/well) for at least 30 minutes. Fixing with formaldehyde enhances the O.D. compared with ethanol.

The wells were washed one time with borate buffer (0.1 M, pH 8.5). Freshly filtered 1% methylene blue solution (0.600 ml/well) was then added to the wells and incubated for 10 minutes at room temperature. The wells were then washed five times with tap water, after which the wells were dried completely. 0.200 ml/well of 0.1 N HCl was added to extract the color. After extracting overnight, the O.D. was read at 630 nm to determine the number of cells per well. The procedure for counting cells is described in greater detail in Oliver et al., *J. of Cell Sci.,* 92:513 (1989), the teachings of which are incorporated herein by reference.

The results for αD peptide K086D101 is shown in Table I.

TABLE I

| Peptide | S.I.* (µM) for HEC Cells | S.I.* (µM) for PC3 Cells |
|---|---|---|
| K086D101 | 0.6 | 0.6 |

*Concentration at which significant inhibition of cell proliferation was observed.

As can be determined from the results in Table I, D peptide derivatives of Jak3 inhibited cell proliferation of human endothelial cells and human prostate cancer cell line PC3.

EXAMPLE 3

Appetite Suppression by Jak2-Derived Peptide

Male CB6F1 or C57BL mice (Harlan), about 2–4 months old, were fed a pelleted rodent maintenance diet (Koffolk, Tel Aviv, Israel, 19520). The food containers for each group were weighed daily and the average food consumption was calculated per mouse per day.

During the experimental period, the mice were injected intraperitoneally once a day for two consecutive days, 4 mg/mouse, with K085D102 (a Jak2-derived peptide from the αD region) solubilized in 10% DMSO in PBS+0.1% BSA in a volume of 0.2 ml. The control groups were injected with 0.2 ml of the vehicle only.

FIGS. 4 and 5 illustrate the results obtained with CB6F1 mice while Table II summarizes the results obtained with C57BL mice.

TABLE II

|  | | Food Intake (g/mouse/day) | | | | % change in body wt. (relative to day 0) | | |
| --- | --- | --- | --- | --- | --- | --- | --- | --- |
|  | n | baseline | treatment day 1 | treatment day 2 | recovery | day 0 | treatment day 1 | treatment day 2 | recovery |
| Control I | 5 | 3.19 | 2.88 | 3.12 | 4.68 | 100% | 99% | 100% | 102% |
| Control II | 5 | 3.68 | 2.85 | 4.92 | 4.5 | 100% | 97% | 99% | 100% |
| Experiment | 4 | 3.16 | 0.24 | 1.43 | 3.62 | 100% | 94% | 95% | 97% |

These results demonstrate that peptides from the αD region of Jak2 have a marked effect on food intake and, concomitantly, on body weight. These peptides exhibit appetite suppression properties.

EXAMPLE 4

Th1/Th2 Bioassay $0.5 \times 10^6$ small resting CD4+ T cells were isolated from lymph nodes of 8 week-old Balb/c mice. These CD4+ T cells were incubated for 5 days in 2 ml culture medium in 24 well plates coated with anti-CD3 and anti-CD28 antibodies: (5 $\mu$g/ml and 2 $\mu$g/ml, respectively). 0.4, 2 or 10 $\mu$M Jak-derived peptides, initially in 10 $\mu$l DMSO, were present in the medium during the 5 day activation period. Control wells contained 10 $\mu$l of DMSO (the solvent of the peptide).

At the end of the 5 day stimulation period, the medium was replaced with fresh medium containing 10 u/ml IL-2 and the cells were removed from the antibody-coated wells to uncoated wells for a 3 day "rest" and expansion period. Under these stimulating and rest conditions, the differentiation process led to the acquisition of Th2 phenotype (high IL-4 and low IFNγ production upon secondary challenge).

At the end of the rest period, the cells were removed, washed and counted. $0.5 \times 10^6$ cells were re-stimulated in 1 ml of culture medium by incubation for 24 hours on anti-CD3-+anti-CD28-coated 24 well plates. At the end of the 24 hour re-stimulation period, the supernatant was removed and the level of secreted IL-4 and IFNγ was determined by ELISA. The results were expressed as u/ml or pg/ml of IL-4 and IFNγ respectively, which were secreted into the culture medium by $0.5 \times 10^6$ cells during the re-stimulation period.

FIG. 6 depicts an undeniable Th1 conversion of CD4+ T cells incubated in the presence of various concentrations of the Jak3 K086D102 peptide, derived from the αD region. The Th1 conversion is manifested by an increase in IFNγ production and a decrease in IL-4 production. This demonstrates the cell differentiation and induction properties of these αDregion peptides.

EXAMPLE 5

Glucose Uptake by Adipose Tissue Cells

1. Materials
   30 ml plastic bottle (Nalgene 2103-0001)
   50 ml plastic conical tube (Miniplast 204-21)
   TC tubes (Nunc 146183)
   Test tubes (Sarstedt 72.7000)
   250 $\mu$nylon mesh
   Collagenase Type 1 (Worthington CLS 4196)
   Dinonyl phthalate (Merck 1.09669.0100)
   3 H-Deoxy Glucose (ICN 27088S.2), 30 Ci/mmole, 0.25 mCi, 0.25 ml 2. Adipose Cell Isolation
   Krebs Ringer Bicarbonate HEPES buffer, containing 1% bovine fraction 5 albumin and 200 nM adenosine was made, using stock solutions:

Stock solution 1—salts
   120 mM 35.04 NaCl
   4 mM 2.73 g $KH_2PO_4$
   1 mM 0.55 g $CaCl_2$ (0.74 g $CaCl_2.2H_2O$); dissolved in a small flask and added to other salts.
   Stock solution 2—Sodium bicarbonate
   10 mM 4.2 g $NaHCO_3$; dissolved in a 500 ml volumetric flask.
   Stock solution 3—HEPES
   30 mM 35.75 g HEPES (39.05 g HEPES Sodium salt); dissolved in a 500 ml volumetric flask pH to 7.4 before being brought up to volume.
   10 ml of each solution (1, 2 and 3) was used per 100 ml double distilled water on day of use.
   Stock solution 4—Adenosine (2 mM)
   To 3 ml of buffer with 10 mg collagenase, 3 g epididymal fat pad (from 2–3 male rats) was introduced. The fat was cut up with scissors. The pieces of fat were swirled and shaken in a 37° C. water bath set at 100–150 repetitions/minute for approximately 1 hour with swirling every 15 minutes while digesting and every 5 minutes towards the end. About 6 ml of buffer was added to the vial.

A 250$\mu$ nylon mesh over the top was secured with a rubber band and the contents of the container were gently squeezed into a 50 ml plastic tube. The total volume for each wash was 15 ml.

The tube was centrifuged. The adipose cells floated to the top of the liquid. The buffer was removed using a 35 ml metal-tipped syringe with a needle. Buffer was added to 15 ml and the clumps of cells were gently broken up by mixing up and down in the syringe. This process was repeated for a total of 4 centrifugations at 1000 with the last centrifugation at 2000 rpm. At this point, any fat was removed from the top of the cells.

Buffer and dilute cell suspension with buffer were removed to cytocrit of 5–10%. The cells were kept at 37° C. for 1 hour.

3. Glucose Uptake
   500 $\mu$l buffer was added with or without additives (insulin 10–10,000 $\mu$U/ml, peptides 0.1–10 $\mu$M) to 10 ml plastic tubes.
   500 $\mu$l aliquots of the cell suspension were added to the tubes.
   After incubation for 30 minutes at 37° C. in a shaking water bath (approximately 300 strokes/minute), 200 $\mu$l of buffer containing 3H—Deoxy Glucose (approx. 1200 cpm/ µl) was added to each tube.

After 30 minutes incubation with 3H-DOG at 37° C., 200 µl aliquots were transferred to microcentrifuge tubes containing 200 µl Dinonyl phthalate. Cells were rapidly separated from the aqueous buffer by centrifugation at 10,000 g for 30–60 sec. Cells separated in the top layer from the aqueous buffer by Dinonyl phthalate.

Cell associated radioactivity was counted in a liquid scintillation counter.

Inhibition of Glucose-Uptake by IRK-Derived Peptide

Glucose-uptake was measured in fresh adipocytes, incubated with or without insulin (10 µU) as described above, in the absence (control) or the presence of 10 µM of peptide K094D101 (derived from the αD region of IRK). The results are shown in Table III.

TABLE III

| Glucose-Update: Mean DPM ± SEM of Quadruplicates | | |
|---|---|---|
| | −Insulin | +Insulin 10 µU/ml |
| Control | 1,149 ± 122 | 1,803 ± 136 |
| +K094D101 | 775 ± 72 | 1,210 ± 110 |
| % K094D101 Control | 67% | 67& |

These results show that peptides from the αD region of IRK inhibit the uptake of glucose by adipocytes, in the presence or absence of insulin.

EXAMPLE 6

The Induction of Melanogenesis by a Peptide Derived from the αD Region of Jak 2

B16 melanoma cells (a mouse tumor cell line) were cultured in a 24-well plate, $10^5$ cells/well, in the presence of various concentrations of K085D102, a Jak2-derived peptide from the αD region. After 5 days incubation in DMEM+ 10% fetal calf serum under standard conditions, the plate was observed by eye for melanogenesis. Melanogenesis induction was visualized by an increase in the amount of the black pigment in the well. The results are illustrated in FIG. 7 and clearly show a dose response down to a concentration as low as 0.15 µM of the Jak2 peptide of the αD region present in the well.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A peptide capable of modulating the activity of a protein kinase having a structure that includes the twelve subdomains and nine alpha helices that are characteristic of the protein kinase superfamily, consisting of:
   a) an αD region peptide consisting of a sequence of about 20 amino acid residues of the protein kinase Subdomain V and the beginning of Subdomain VI, beginning at the end of the b5 beta sheet and extending through the D helix and the following loop to the beginning of helix E, which amino acids correspond to a continuous stretch of the prototypical PKA-Cα in positions 120–139 of the PKA-Cα, and which αD region peptide modulates the activity of the protein kinase;
   b) a subsequence peptide consisting of a subsequence of a) consisting of at least five contiguous amino acids thereof, which subsequence peptide modulates the activity of the protein kinase;
   c) a modified sequence peptide having a modified sequence of a) or b) in which up to two residues are each substituted by another amino acid residue or amino acid residue analog other than one which is identical to the one being substituted except that a functional group in the side chain is functionalized with a protecting group, which modified sequence peptide modulates the activity of the protein kinase;
   d) a protected peptide a), b) or c) in which the N-terminus and/or the C-terminus is protected by a protecting group and/or one or more side chains of the amino acid residues of the peptide of a), b) or c) have been functionalized with a protecting group, which protected peptide modulates the activity of the protein kinase; or
   e) a cyclized peptide of a), b), c) or d) which has been cyclized, which cyclized peptide modulates the activity of the protein kinase, wherein the peptide has the sequence of SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114 SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, or SEQ ID NO:170.

2. A peptide having the sequence of SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ED NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, or SEQ ID NO:170, with the proviso that any one amino acid residue in the peptide can be substituted by another amino acid residue or amino acid residue analog.

3. A peptide consisting of a sequence of amino acids $AA_1$ through $AA_{23}$ or a subsequence thereof comprising at least five amino acids, wherein:
   $AA_1$ is selected from the group consisting of leucine, methionine, isoleucine and valine;
   $AA_2$ is selected from the group consisting of aspartic acid, threonine, glutamic acid, serine and an aliphatic, substituted aliphatic, benzyl, substituted benzyl, aromatic or substituted aromatic ester of a glutamic acid or aspartic acid;
   $AA_3$ is selected from the group consisting of leucine, isoleucine, methionine and valine;
   $AA_4$ is selected from the group consisting of methionine, isoleucine, leucine and valine;
   $AA_5$ is selected from the group consisting of asparagine and glutamine;
   $AA_6$ is selected from the group consisting of glycine and alanine;

AA$_7$ is selected from the group consisting of glycine and alanine;

AA$_8$ is selected from the group consisting of aspartic acid, glutamic acid and an aliphatic, substituted aliphatic, benzyl, substituted benzyl, aromatic or substituted aromatic ester of a glutamic acid or aspartic acid;

AA$_9$ is selected from the group consisting of leucine, isoleucine, methionine and valine;

AA$_{10}$ is selected from the group consisting of histidine, arginine and lysine;

AA$_{11}$ is selected from the group consisting of tyrosine, phenylalanine and tryptophan;

AA$_{12}$ is histidine;

AA$_{13}$ is selected from the group consisting of leucine, isoleucine, methionine and valine;

AA$_{14}$ is selected from the group consisting of serine, tyrosine, threonine, phenylalanine and tryptophan;

AA$_{15}$ is selected from the group consisting of glutamine, asparagine and histidine;

AA$_{16}$ is selected from the group consisting of histidine, valine, leucine, methionine and isoleucine;

AA$_{17}$ is selected from the group consisting of glycine, aspartic acid, glutamic acid, alanine and an aliphatic, substituted aliphatic, benzyl, substituted benzyl, aromatic or substituted aromatic ester of a glutamic acid or aspartic acid;

AA$_{18}$ is selected from the group consisting of valine, glutamic acid, asparagine, glutamine, isoleucine, leucine, methionine, aspartic acid and an aliphatic, substituted aliphatic, benzyl, substituted benzyl, aromatic or substituted aromatic ester of a glutamic acid or aspartic acid;

AA$_{19}$ is selected from the group consisting of phenylalanine, aspartic acid, proline, alanine, tryptophan, tyrosine, glutamic acid, glycine and an aliphatic, substituted aliphatic, benzyl, substituted benzyl, aromatic or substituted aromatic ester of a glutamic acid or aspartic acid;

AA$_{20}$ is selected from the group consisting of asparagine, glycine, glutamine and alanine;

AA$_{21}$ is selected from the group consisting of proline, phenylalanine, tryptophan and tyrosine;

AA$_{22}$ is selected from the group consisting of glycine and alanine; and

AA$_{23}$ is selected from the group consisting of phenylalanine, tryptophan and tyrosine, wherein the sequence AA$_1$ through AA$_{23}$ or a subsequence thereof corresponds to the sequence or a subsequence of the αD region of a G protein-coupled receptor kinase selected from the group consisting of SEQ ID NO:18, SEQ ID NO:19, SEQ ID NO:20, SEQ ID NO:21 and SEQ ID NO:22, with the proviso that any one amino acid in the sequence AA$_1$ through AA$_{23}$ or the subsequence thereof can vary as set forth above.

4. A peptide consisting of a sequence of amino acids AA$_1$ through AA$_{20}$ or a subsequence thereof comprising at least seven amino acids, wherein:

AA$_1$ is selected from the group consisting of phenylalanine, tryptophan and tyrosine;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of phenylalanine, histidine, tryptophan and tyrosine;

AA$_4$ is selected from the group consisting of leucine, valine, isoleucine and methionine;

AA$_5$ is selected from the group consisting of histidine, aspartic acid, glutamic acid, and an aliphatic, substituted aliphatic, benzyl, substituted benzyl, aromatic or substituted aromatic ester of glutamic acid or aspartic acid;

AA$_6$ is selected from the group consisting of glutamine and asparagine;

AA$_7$ is selected from the group consisting of aspartic acid, glutamic acid and an aliphatic, substituted aliphatic, benzyl, substituted benzyl, aromatic or substituted aromatic ester of glutamic acid or aspartic acid;

AA$_8$ is selected from the group consisting of leucine, isoleucine, methionine and valine;

AA$_9$ is selected from the group consisting of lysine, arginine, threonine and serine;

AA$_{10}$ is selected from the group consisting of lysine, threonine, arginine and serine;

AA$_{11}$ is selected from the group consisting of phenylalanine, tyrosine and tryptophan;

AA$_{12}$ is selected from the group consisting of methionine, leucine, isoleucine and valine;

AA$_{13}$ is selected from the group consisting of aspartic acid, glutamic acid and an aliphatic, substituted aliphatic, benzyl, substituted benzyl, aromatic or substituted aromatic ester of glutamic acid or aspartic acid;

AA$_{14}$ is selected from the group consisting of alanine, lysine, arginine and glycine;

AA$_{15}$ is selected from the group consisting of valine, serine, alanine, isoleucine, leucine, methionine and threonine;

AA$_{16}$ is selected from the group consisting of alanine, proline and glycine;

AA$_{17}$ is selected from the group consisting of leucine, proline, glutamic acid, isoleucine, methionine, valine, aspartic acid and an aliphatic, substituted aliphatic, benzyl, substituted benzyl, aromatic or substituted aromatic ester of glutamic acid or aspartic acid;

AA$_{18}$ is selected from the group consisting of threonine, proline and serine;

AA$_{19}$ is selected from the group consisting of glycine and alanine; and

AA$_{20}$ is selected from the group consisting of isoleucine, leucine, valine and methionine.

5. The peptide of claim 4 wherein the sequence AA$_1$ through AA$_{20}$ or a subsequence thereof corresponds to a sequence of the αD region of a cyclin dependent kinase selected from the group consisting of SEQ ID NO:35, SEQ ID NO:36 and SEQ ID NO:37 or a subsequence thereof, with the proviso that any two amino acids in the sequence AA$_1$ through AA$_{20}$ or the subsequence thereof can vary as set forth in claim 4.

6. The peptide of claim 4 wherein the sequence AA$_1$ through AA$_{20}$ or a subsequence thereof corresponds to a sequence of the αD region of a cyclin dependent kinase selected from the group consisting of SEQ ID NO:35, SEQ ID NO:36 and SEQ ID NO:37 or a subsequence thereof, with the proviso that any one amino acid in the sequence AA$_1$ through AA$_{20}$ or the subsequence thereof can vary as set forth in claim 4.

7. A peptide consisting of a sequence of amino acids AA$_1$ through AA$_{21}$ or a subsequence thereof comprising at least seven amino acids, wherein:

AA₁ is selected from the group consisting of threonine, methionine, serine, isoleucine, leucine and valine;

AA₂ is selected from the group consisting of glutamic acid, aspartic acid and an aliphatic, substituted aliphatic, benzyl, substituted benzyl, aromatic or substituted aromatic ester of glutamic acid or aspartic acid;

AA₃ is selected from the group consisting of phenylalanine, tyrosine, histidine and tryptophan;

AA₄ is selected from the group consisting of methionine, valine, isoleucine and leucine;

AA₅ is selected from the group consisting of serine, asparagine, cysteine, alanine, glutamic acid, threonine, glutamine, aspartic acid, glycine and an aliphatic, substituted aliphatic, benzyl, substituted benzyl, aromatic or substituted aromatic ester of glutamic acid or aspartic acid;

AA₆ is selected from the group consisting of lysine, histidine, asparagine, arginine and glutamine;

AA₇ is selected from the group consisting of glycine and alanine;

AA₈ is selected from the group consisting of serine, asparagine, threonine and glutamine;

AA₉ is selected from the group consisting of leucine, isoleucine, methionine and valine;

AA₁₀ is selected from the group consisting of leucine, valine, isoleucine and methionine;

AA₁₁ is selected from the group consisting of aspartic acid, asparagine, glutamic acid, glutamine and an aliphatic, substituted aliphatic, benzyl, substituted benzyl, aromatic or substituted aromatic ester of glutamic acid or aspartic acid;

AA₁₂ is selected from the group consisting of phenylalanine, tyrosine and tryptophan;

AA₁₃ is selected from the group consisting of leucine, isoleucine, methionine and valine;

AA₁₄ is selected from the group consisting of lysine and arginine;

AA₁₅ is selected from the group consisting of glycine, glutamic acid, aspartic acid, asparagine, serine, threonine, glutamine, alanine and an aliphatic, substituted aliphatic, benzyl, substituted benzyl, aromatic or substituted aromatic ester of glutamic acid or aspartic acid;

AA₁₆ is selected from the group consisting of glutamic acid, glycine, proline, aspartic acid, arginine, lysine, alanine and an aliphatic, substituted aliphatic, benzyl, substituted benzyl, aromatic or substituted aromatic ester of glutamic acid or aspartic acid;

AA₁₇ is selected from the group consisting of threonine, serine, aspartic acid, glutamic acid, glycine, alanine and an aliphatic, substituted aliphatic, benzyl, substituted benzyl, aromatic or substituted aromatic ester of glutamic acid or aspartic acid;

AA₁₈ is selected from the group consisting of glycine, arginine, lysine and alanine;

AA₁₉ is selected from the group consisting of lysine, arginine, glutamine, glycine, serine, isoleucine, alanine, asparagine, threonine, leucine, methionine and valine;

AA₂₀ is selected from the group consisting of tyrosine, alanine, aspartic acid, lysine, valine, leucine, phenylalanine, tryptophan, glutamic acid, arginine, isoleucine, methionine, glycine and an aliphatic, substituted aliphatic, benzyl, substituted benzyl, aromatic or substituted aromatic ester of glutamic acid or aspartic acid; and AA₂₁ is selected from the group consisting of leucine, valine, glutamine, isoleucine, methionine and asparagine.

8. The peptide of claim 7 wherein the sequence AA₁ through AA₂₁ or a subsequence thereof corresponds to the sequence of the αD region of a Src family kinase selected from the group consisting of SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46 or a subsequence thereof, with the proviso that any two amino acids in the sequence AA₁ through AA₂₁ or the subsequence thereof can vary as set forth in claim 7.

9. The peptide of claim 7 wherein the sequence AA₁ through AA₂₁ or a subsequence thereof corresponds to the sequence of the αD region of a Src family kinase selected from the group consisting of SEQ ID NO:38, SEQ ID NO:39, SEQ ID NO:40, SEQ ID NO:41, SEQ ID NO:42, SEQ ID NO:43, SEQ ID NO:44, SEQ ID NO:45 and SEQ ID NO:46 or a subsequence thereof, with the proviso that any one amino acid in the sequence AA₁ through AA₂₁ or the subsequence thereof can vary as set forth in claim 7.

10. A peptide consisting of a sequence of amino acids AA₁ through AA₃₉ or a subsequence thereof comprising at least seven amino acids, wherein:

AA₁ is selected from the group consisting of isoleucine, threonine, valine, leucine, methionine and serine;

AA₂ is selected from the group consisting of glutamic acid, aspartic acid and an aliphatic, substituted aliphatic, benzyl, substituted benzyl, aromatic or substituted aromatic ester of glutamic acid or aspartic acid;

AA₃ is selected from the group consisting of tyrosine, phenylalanine and tryptophan;

AA₄ is selected from the group consisting of alanine, cysteine, serine, thronine and glycine;

AA₅ is selected from the group consisting of glycine, arginine, phenylalanine, lysine, tryptophan and tyrosine;

AA₆ is selected from the group consisting of tyrosine, histidine, phenylalanine and tryptophan;

AA₇ is selected from the group consisting of glycine and alanine;

AA₈ is selected from the group consisting of asparagine, aspartic acid, glutamine, glutamic acid and an aliphatic, substituted aliphatic, benzyl, substituted benzyl, aromatic or substituted aromatic ester of glutamic acid or aspartic acid;

AA₉ is selected from the group consisting of leucine, isoleucine, methionine and valine;

AA₁₀ is selected from the group consisting of leucine, valine, serine, isoleucine, methionine and threonine;

AA₁₁ is selected from the group consisting of aspartic acid, asparagine, threonine, glutamic acid, glutamine, serine and an aliphatic, substituted aliphatic, benzyl, substituted benzyl, aromatic or substituted aromatic ester of glutamic acid or aspartic acid;

AA₁₂ is selected from the group consisting of phenylalanine, tyrosine and tryptophan;

AA₁₃ is selected from the group consisting of leucine, isoleucine, methionine and valine;

AA₁₄ is selected from the group consisting of arginine, histidine and lysine;

AA₁₅ is selected from the group consisting of lysine, arginine, serine, alanine, glycine and threonine;

AA₁₆ is selected from the group consisting of serine, asparagine, lysine, threonine, glutamine and arginine;

AA$_{17}$ is selected from the group consisting of arginine and lysine;

AA$_{18}$ is selected from the group consisting of valine, histidine, aspartic acid, asparagine, isoleucine, leucine, methionine, glutamic acid, glutamine and an aliphatic, substituted aliphatic, benzyl, substituted benzyl, aromatic or substituted aromatic ester of glutamic acid or aspartic acid;

AA$_{19}$ is selected from the group consisting of leucine, threonine, serine, alanine, glutamic acid, isoleucine, methionine, valine, aspartic acid, glycine and an aliphatic, substituted aliphatic, benzyl, substituted benzyl, aromatic or substituted aromatic ester of glutamic acid or aspartic acid;

AA$_{20}$ is selected from the group consisting of glutamic acid, phenylalanine, aspartic acid, tryptophan, tyrosine and an aliphatic, substituted aliphatic, benzyl, substituted benzyl, aromatic or substituted aromatic ester of glutamic acid or aspartic acid;

AA$_{21}$ is selected from the group consisting of threonine, leucine, phenylalanine, serine, valine, isoleucine, methionine, tryptophan and tyrosine;

AA$_{22}$ is selected from the group consisting of aspartic acid, glutamine, serine, leucine, proline, glutamic acid, asparagine, threonine, isoleucine, methionine, valine and an aliphatic, substituted aliphatic, benzyl, substituted benzyl, aromatic or substituted aromatic ester of glutamic acid or aspartic acid;

AA$_{23}$ is selected from the group consisting of proline, histidine, asparagine, cysteine, tyrosine, glutamine, phenylalanine, tryptophan, and serine;

AA$_{24}$ is selected from the group consisting of alanine, histidine, lysine, arginine and glycine;

AA$_{25}$ is selected from the group consisting of phenylalanine, serine, proline, aspartic acid, glutamic acid, tryptophan, tyrosine, threonine and an aliphatic, substituted aliphatic, benzyl, substituted benzyl, aromatic or substituted aromatic ester of glutamic acid or aspartic acid;

AA$_{26}$ is selected from the group consisting of alanine, aspartic acid, glutamic acid, lysine, arginine, glycine and an aliphatic, substituted aliphatic, benzyl, substituted benzyl, aromatic or substituted aromatic ester of glutamic acid or aspartic acid;

AA$_{27}$ is selected from the group consisting of arginine, isoleucine, lysine, alanine, serine, glycine, leucine, methionine, valine and threonine;

AA$_{28}$ is selected from the group consisting of glutamic acid, alanine, arginine, proline, leucine, aspartic acid, lysine, isoleucine, methionine, valine, glycine and an aliphatic, substituted aliphatic, benzyl, substituted benzyl, aromatic or substituted aromatic ester of glutamic acid or aspartic acid;

AA$_{29}$ is selected from the group consisting of histidine, asparagine, arginine, lysine, glutamic acid, glutamine, aspartic acid and an aliphatic, substituted aliphatic, benzyl, substituted benzyl, aromatic or substituted aromatic ester of glutamic acid or aspartic acid;

AA$_{30}$ is selected from the group consisting of glycine, serine, proline, lysine, methionine, glutamine, phenylalanine, threonine, arginine, isoleucine, leucine, valine, asparagine, tryptophan, tyrosine and alanine;

AA$_{31}$ is selected from the group consisting of threonine, proline, glutamic acid, arginine, serine, aspartic acid, lysine and an aliphatic, substituted aliphatic, benzyl, substituted benzyl, aromatic or substituted aromatic ester of glutamic acid or aspartic acid;

AA$_{32}$ is selected from the group consisting of serine, alanine, aspartic acid, lysine, arginine, glycine, threonine, glutamic acid and an aliphatic, substituted aliphatic, benzyl, substituted benzyl, aromatic or substituted aromatic ester of glutamic acid or aspartic acid;

AA$_{33}$ is selected from the group consisting of threonine, glutamic acid, isoleucine, lysine, phenylalanine, serine, aspartic acid, leucine, methionine, valine, arginine, tryptophan, tyrosine and an aliphatic, substituted aliphatic, benzyl, substituted benzyl, aromatic or substituted aromatic ester of glutamic acid or aspartic acid;

AA$_{34}$ is selected from the group consisting of leucine, phenylalanine, glutamic acid, arginine, aspartic acid, isoleucine, methionine, valine, tryptophan, tyrosine, lysine and an aliphatic, substituted aliphatic, benzyl, substituted benzyl, aromatic or substituted aromatic ester of glutamic acid or aspartic acid;

AA$_{35}$ is selected from the group consisting of tyrosine, glycine, lysine, alanine, phenylalanine, tryptophan and arginine;

AA$_{36}$ is selected from the group consisting of serine, leucine, methionine, valine, threonine, and isoleucine;

AA$_{37}$ is selected from the group consisting of asparagine, glutamic acid, valine, glycine, glutamine, aspartic acid, isoleucine, leucine, methionine, alanine and an aliphatic, substituted aliphatic, benzyl, substituted benzyl, aromatic or substituted aromatic ester of glutamic acid or aspartic acid;

AA$_{38}$ is selected from the group consisting of alanine, proline, glutamic acid, aspartic acid, glycine and an aliphatic, substituted aliphatic, benzyl, substituted benzyl, aromatic or substituted aromatic ester of glutamic acid or aspartic acid;

AA$_{39}$ is selected from the group consisting of leucine, alanine, glycine, isoleucine, methionine and valine, wherein the sequence AA$_1$ through AA$_{39}$ or a subsequence thereof corresponds to the sequence of the αD region of an endothelial growth factor receptor kinase selected from the group consisting of SEQ ID NO:49 and SEQ ID NO:50 or a subsequence thereof, with the proviso that any two amino acids in the sequence AA$_1$ through AA$_{39}$ or the subsequence thereof can vary as set forth above.

11. A peptide consisting of a sequence of amino acids AA$_1$ through AA$_{39}$ or a subsequence thereof comprising at least seven amino acids, wherein:

AA$_1$ is selected from the group consisting of isoleucine, threonine, valine, leucine, methionine and serine;

AA$_2$ is selected from the group consisting of glutamic acid, aspartic acid and an aliphatic, substituted aliphatic, benzyl, substituted benzyl, aromatic or substituted aromatic ester of glutamic acid or aspartic acid;

AA$_3$ is selected from the group consisting of tyrosine, phenylalanine and tryptophan;

AA$_4$ is selected from the group consisting of alanine, cysteine, serine, thronine and glycine;

AA$_5$ is selected from the group consisting of glycine, arginine, phenylalanine, lysine, tryptophan and tyrosine;

AA$_6$ is selected from the group consisting of tyrosine, histidine, phenylalanine and tryptophan;

AA$_7$ is selected from the group consisting of glycine and alanine;

$AA_8$ is selected from the group consisting of asparagine, aspartic acid, glutamine, glutamic acid and an aliphatic, substituted aliphatic, benzyl, substituted benzyl, aromatic or substituted aromatic ester of glutamic acid or aspartic acid;

$AA_9$ is selected from the group consisting of leucine, isoleucine, methionine and valine;

$AA_{10}$ is selected from the group consisting of leucine, valine, serine, isoleucine, methionine and threonine;

$AA_{11}$ is selected from the group consisting of aspartic acid, asparagine, threonine, glutamic acid, glutamine, serine and an aliphatic, substituted aliphatic, benzyl, substituted benzyl, aromatic or substituted aromatic ester of glutamic acid or aspartic acid;

$AA_{12}$ is selected from the group consisting of phenylalanine, tyrosine and tryptophan;

$AA_{13}$ is selected from the group consisting of leucine, isoleucine, methionine and valine;

$AA_{14}$ is selected from the group consisting of arginine, histidine and lysine;

$AA_{15}$ is selected from the group consisting of lysine, arginine, serine, alanine, glycine and threonine;

$AA_{16}$ is selected from the group consisting of serine, asparagine, lysine, threonine, glutamine and arginine;

$AA_{17}$ is selected from the group consisting of arginine and lysine;

$AA_{18}$ is selected from the group consisting of valine, histidine, aspartic acid, asparagine, isoleucine, leucine, methionine, glutamic acid, glutamine and an aliphatic, substituted aliphatic, benzyl, substituted benzyl, aromatic or substituted aromatic ester of glutamic acid or aspartic acid;

$AA_{19}$ is selected from the group consisting of leucine, threonine, serine, alanine, glutamic acid, isoleucine, methionine, valine, aspartic acid, glycine and an aliphatic, substituted aliphatic, benzyl, substituted benzyl, aromatic or substituted aromatic ester of glutamic acid or aspartic acid;

$AA_{20}$ is selected from the group consisting of glutamic acid, phenylalanine, aspartic acid, tryptophan, tyrosine and an aliphatic, substituted aliphatic, benzyl, substituted benzyl, aromatic or substituted aromatic ester of glutamic acid or aspartic acid;

$AA_{21}$ is selected from the group consisting of threonine, leucine, phenylalanine, serine, valine, isoleucine, methionine, tryptophan and tyrosine;

$AA_{22}$ is selected from the group consisting of aspartic acid, glutamine, serine, leucine, proline, glutamic acid, asparagine, threonine, isoleucine, methionine, valine and an aliphatic, substituted aliphatic, benzyl, substituted benzyl, aromatic or substituted aromatic ester of glutamic acid or aspartic acid;

$AA_{23}$ is selected from the group consisting of proline, histidine, asparagine, cysteine, tyrosine, glutamine, phenylalanine, tryptophan, and serine;

$AA_{24}$ is selected from the group consisting of alanine, histidine, lysine, arginine and glycine;

$AA_{25}$ is selected from the group consisting of phenylalanine, serine, proline, aspartic acid, glutamic acid, tryptophan, tyrosine, threonine and an aliphatic, substituted aliphatic, benzyl, substituted benzyl, aromatic or substituted aromatic ester of glutamic acid or aspartic acid;

$AA_{26}$ is selected from the group consisting of alanine, aspartic acid, glutamic acid, lysine, arginine, glycine and an aliphatic, substituted aliphatic, benzyl, substituted benzyl, aromatic or substituted aromatic ester of glutamic acid or aspartic acid;

$AA_{27}$ is selected from the group consisting of arginine, isoleucine, lysine, alanine, serine, glycine, leucine, methionine, valine and threonine;

$AA_{28}$ is selected from the group consisting of glutamic acid, alanine, arginine, proline, leucine, aspartic acid, lysine, isoleucine, methionine, valine, glycine and an aliphatic, substituted aliphatic, benzyl, substituted benzyl, aromatic or substituted aromatic ester of glutamic acid or aspartic acid;

$AA_{29}$ is selected from the group consisting of histidine, asparagine, arginine, lysine, glutamic acid, glutamine, aspartic acid and an aliphatic, substituted aliphatic, benzyl, substituted benzyl, aromatic or substituted aromatic ester of glutamic acid or aspartic acid;

$AA_{30}$ is selected from the group consisting of glycine, serine, proline, lysine, methionine, glutamine, phenylalanine, threonine, arginine, isoleucine, leucine, valine, asparagine, tryptophan, tyrosine and alanine;

$AA_{31}$ is selected from the group consisting of threonine, proline, glutamic acid, arginine, serine, aspartic acid, lysine and an aliphatic, substituted aliphatic, benzyl, substituted benzyl, aromatic or substituted aromatic ester of glutamic acid or aspartic acid;

$AA_{32}$ is selected from the group consisting of serine, alanine, aspartic acid, lysine, arginine, glycine, threonine, glutamic acid and an aliphatic, substituted aliphatic, benzyl, substituted benzyl, aromatic or substituted aromatic ester of glutamic acid or aspartic acid;

$AA_{33}$ is selected from the group consisting of threonine, glutamic acid, isoleucine, lysine, phenylalanine, serine, aspartic acid, leucine, methionine, valine, arginine, tryptophan, tyrosine and an aliphatic, substituted aliphatic, benzyl, substituted benzyl, aromatic or substituted aromatic ester of glutamic acid or aspartic acid;

$AA_{34}$ is selected from the group consisting of leucine, phenylalanine, glutamic acid, arginine, aspartic acid, isoleucine, methionine, valine, tryptophan, tyrosine, lysine and an aliphatic, substituted aliphatic, benzyl, substituted benzyl, aromatic or substituted aromatic ester of glutamic acid or aspartic acid;

$AA_{35}$ is selected from the group consisting of tyrosine, glycine, lysine, alanine, phenylalanine, tryptophan and arginine;

$AA_{36}$ is selected from the group consisting of serine, leucine, methionine, valine, threonine, and isoleucine;

$AA_{37}$ is selected from the group consisting of asparagine, glutamic acid, valine, glycine, glutamine, aspartic acid, isoleucine, leucine, methionine, alanine and an aliphatic, substituted aliphatic, benzyl, substituted benzyl, aromatic or substituted aromatic ester of glutamic acid or aspartic acid;

$AA_{38}$ is selected from the group consisting of alanine, proline, glutamic acid, aspartic acid, glycine and an aliphatic, substituted aliphatic, benzyl, substituted benzyl, aromatic or substituted aromatic ester of glutamic acid or aspartic acid;

$AA_{39}$ is selected from the group consisting of leucine, alanine, glycine, isoleucine, methionine and valine, wherein the sequence $AA_1$ through $AA_{39}$ or a subsequence thereof corresponds to the sequence of the αD region of an endothelial growth factor receptor kinase selected from the group consisting of SEQ ID NO:49 and SEQ ID NO:50 or a subsequence thereof, with the proviso that any one amino acid in the sequence $AA_1$ through $AA_{39}$ or the subsequence thereof can vary as set forth above.

12. A peptide consisting of a sequence of amino acids $AA_1$ through $AA_{34}$ or a subsequence thereof comprising at least seven amino acids, wherein:

$AA_1$ is selected from the group consisting of valine, isoleucine, leucine and methionine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of tyrosine, cysteine, phenylalanine, tryptophan and serine;

$AA_4$ is selected from the group consisting of alanine and glycine;

$AA_5$ is selected from the group consisting of serine, alanine, threonine and glycine;

$AA_6$ is selected from the group consisting of lysine and arginine;

$AA_7$ is selected from the group consisting of glycine and alanine;

$AA_8$ is selected from the group consisting of asparagine and glutamine;

$AA_9$ is selected from the group consisting of leucine, isoleucine, methionine and valine;

$AA_{10}$ is selected from the group consisting of arginine and lysine;

$AA_{11}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{12}$ is selected from the group consisting of tyrosine, phenylalanine and tryptophan;

$AA_{13}$ is selected from the group consisting of leucine, isoleucine, methionine and valine;

$AA_{14}$ is selected from the group consisting of glutamine, arginine, asparagine and lysine;

$AA_{15}$ is selected from the group consisting of alanine and glycine;

$AA_{16}$ is selected from the group consisting of arginine and lysine;

$AA_{17}$ is selected from the group consisting of arginine and lysine;

$AA_{18}$ is proline;

$AA_{19}$ is proline;

$AA_{20}$ is selected from the group consisting of glycine and alanine;

$AA_{21}$ is selected from the group consisting of leucine, methionine, proline, isoleucine and valine;

$AA_{22}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{23}$ is selected from the group consisting of tyrosine, leucine, phenylalanine, tryptophan, isoleucine, methionine and valine;

$AA_{24}$ is selected from the group consisting of cysteine, serine and threonine;

$AA_{25}$ is selected from the group consisting of tyrosine, phenylalanine, proline and tryptophan;

$AA_{26}$ is selected from the group consisting of asparagine, aspartic acid, glutamine, glutamic acid and an aliphatic, substituted aliphatic, benzyl, substituted benzyl, aromatic or substituted aromatic ester of glutamic acid or aspartic acid;

$AA_{27}$ is selected from the group consisting of proline, isoleucine, threonine, glycine, leucine, methionine, valine, serine and alanine;

$AA_{28}$ is selected from the group consisting of serine, asparagine, cysteine, proline, threonine and glutamine;

$AA_{29}$ is selected from the group consisting of histidine, arginine and lysine;

$AA_{30}$ is selected from the group consisting of asparagine, valine, proline, serine, glutamine, isoleucine, leucine, methionine and threonine;

$AA_{31}$ is selected from the group consisting of proline, serine and threonine;

$AA_{32}$ is selected from the group consisting of glutamic acid, glycine, aspartic acid, alanine and an aliphatic, substituted aliphatic, benzyl, substituted benzyl, aromatic or substituted aromatic ester of glutamic acid or aspartic acid;

$AA_{33}$ is selected from the group consisting of glutamine, proline and asparagine; and $AA_{34}$ is selected from the group Consisting of leucine, methionine, isoleucine and valine.

13. The peptide of claim 12, wherein the sequence $AA_1$ through $AA_{34}$ or a subsequence thereof corresponds to the sequence of the αD region of a fibroblast growth factor receptor kinase selected from the group consisting of a subsequence of SEQ ID NO:51, a subsequence of SEQ ID NO:52, a subsequence of SEQ ID NO:53 and a subsequence of SEQ ID NO:54, with the proviso that any two amino acids in the subsequence can vary as set forth in claim 12.

14. The peptide of claim 12, wherein the sequence $AA_1$ through $AA_{34}$ or a subsequence thereof corresponds to the sequence of the αD region of a fibroblast growth factor receptor kinase selected from the group consisting of a subsequence of SEQ ID NO:51, a subsequence of SEQ ID NO:52, a subsequence of SEQ ID NO:53 and a subsequence of SEQ ID NO:54, with the proviso that any one amino acid in the subsequence can vary as set forth in claim 12.

15. A peptide consisting of a sequence of amino acids $AA_1$ through $AA_{20}$ or a subsequence thereof comprising at least five amino acids, wherein:

$AA_1$ is selected from the group consisting of methionine, isoleucine, leucine and valine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of phenylalanine, tyrosine, and tryptophan;

$AA_4$ is selected from the group consisting of leucine, isoleucine, methionine and valine;

$AA_5$ is proline;

$AA_6$ is selected from the group consisting of serine, tyrosine, threonine, phenylalanine, tryptophan, leucine and isoleucine;

$AA_7$ is selected from the group consisting of glycine and alanine;

$AA_8$ is selected from the group consisting of serine, cysteine and threonine;

$AA_9$ is selected from the group consisting of leucine, isoleucine, methionine and valine;

$AA_{10}$ is selected from the group consisting of lysine and arginine;

$AA_{11}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{12}$ is selected from the group consisting of tyrosine, phenylalanine and tryptophan;

$AA_{13}$ is selected from the group consisting of leucine, isoleucine, methionine and valine;

$AA_{14}$ is selected from the group consisting of proline, glutamine, and asparagine;

$AA_{15}$ is selected from the group consisting of lysine and arginine;

$AA_{16}$ is selected from the group consisting of asparagine, histidine and glutamine;

$AA_{17}$ is selected from the group consisting of lysine, arginine, serine and threonine;

$AA_{18}$ is selected from the group consisting of asparagine, glutamic acid, alanine, glutamine, aspartic acid, glycine, isoleucine, leucine and an aliphatic, substituted aliphatic, benzyl, substituted benzyl, aromatic or substituted aromatic ester of glutamic acid or aspartic acid;

$AA_{19}$ is selected from the group consisting of lysine and arginine; and $AA_{20}$ is selected from the group consisting of isoleucine, leucine, methionine and valine.

16. The peptide of claim 15 wherein the sequence $AA_1$ through $AA_{20}$ or a subsequence thereof corresponds to the sequence of the αD region of a Tyk/Jak kinase selected from the group consisting of SEQ ID NO:73, SEQ ID NO:74, SEQ ID NO:75 and SEQ ID NO:76 or a subsequence thereof, with the proviso that any two amino acids in the sequence $AA_1$ through $AA_{20}$ or the subsequence thereof can vary as set forth in claim 15.

17. The peptide of claim 15 wherein the sequence $AA_1$ through $AA_{20}$ or a subsequence thereof corresponds to the sequence of the αDregion of a Tyk/Jak kinase selected from the group consisting of SEQ ID NO:73, SEQ ID NO:74, SEQ ID NO:75 and SEQ ID NO:76 or a subsequence thereof, with the proviso that any one amino acid in the sequence $AA_1$ through $AA_{20}$ or the subsequence thereof can vary as set forth in claim 15.

18. A peptide consisting of a sequence of amino acids $AA_1$ through $AA_{31}$ or a subsequence thereof comprising at least five amino acids, wherein:

$AA_1$ is selected from the group consisting of methionine, isoleucine, leucine and valine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of leucine, isoleucine, methionine and valine;

$AA_4$ is selected from the group consisting of methionine, isoleucine, leucine and valine;

$AA_5$ is selected from the group consisting of alanine and glycine;

$AA_6$ is histidine;

$AA_7$ is selected from the group consisting of glycine and alanine;

$AA_8$ is selected from the group consisting of aspartic acid, glutamic acid and an aliphatic, substituted aliphatic, benzyl, substituted benzyl, aromatic or substituted aromatic ester of glutamic acid or aspartic acid;

$AA_9$ is selected from the group consisting of leucine, isoleucine, methionine and valine;

$AA_{10}$ is selected from the group consisting of lysine and arginine;

$AA_{11}$ is selected from the group consisting of serine and threonine;

$AA_{12}$ is selected from the group consisting of tyrosine, phenylalanine and tryptophan;

$AA_{13}$ is selected from the group consisting of leucine, isoleucine, methionine and valine;

$AA_{14}$ is selected from the group consisting of arginine and lysine;

$AA_{15}$ is selected from the group consisting of serine and threonine;

$AA_{16}$ is selected from the group consisting of leucine, isoleucine, methionine and valine;

$AA_{17}$ is selected from the group consisting of arginine and lysine;

$AA_{18}$ is proline;

$AA_{19}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{20}$ is selected from the group consisting of alanine and glycine;

$AA_{21}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{22}$ is selected from the group consisting of asparagine and glutamine;

$AA_{23}$ is selected from the group consisting of asparagine and glutamine;

$AA_{24}$ is proline;

$AA_{25}$ is selected from the group consisting of glycine and alanine;

$AA_{26}$ is selected from the group consisting of arginine and lysine;

$AA_{27}$ is proline;

$AA_{28}$ is proline;

$AA_{29}$ is proline;

$AA_{30}$ is selected from the group consisting of threonine and serine; and $AA_{31}$ is selected from the group consisting of leucine, isoleucine, methionine and valine, with the proviso that the peptide is not represented by the sequence MAHGDLKSYLRSLRPEAENNP (SEQ ID NO:171).

19. The peptide of claim 18 wherein the sequence $AA_1$ through $AA_{31}$ or a subsequence thereof corresponds to the sequence of the αD region of SEQ ID NO:82 or a subsequence thereof, with the proviso that any two amino acids in the sequence $AA_1$ through $AA_{31}$ or the subsequence thereof can vary as set forth in claim 18.

20. The peptide of claim 18 wherein the sequence $AA_1$ through $AA_{31}$ or a subsequence thereof corresponds to the sequence of the αD region of SEQ ID NO:82 or a subsequence thereof, with the proviso that any one amino acid in the sequence $AA_1$ through $AA_{31}$ or the subsequence thereof can vary as set forth in claim 18.

21. A peptide consisting of a sequence of amino acids $AA_1$ through $AA_{18}$ or a subsequence thereof comprising at least seven amino acids, wherein:

$AA_1$ is selected from the group consisting of threonine and serine;

$AA_2$ is selected from the group consisting of alanine and glycine;

$AA_3$ is selected from the group consisting of phenylalanine, tryptophan and tyrosine;

$AA_4$ is histidine;

$AA_5$ is selected from the group consisting of alanine, glutamic acid, aspartic acid, glycine and an aliphatic, substituted aliphatic, benzyl, substituted benzyl, aromatic or substituted aromatic ester of glutamic acid or aspartic acid;

$AA_6$ is selected from the group consisting of lysine and arginine;

$AA_7$ is selected from the group consisting of glycine and alanine;

$AA_8$ is selected from the group consisting of asparagine, serine, glutamine and threonine;

$AA_9$ is selected from the group consisting of leucine, isoleucine, methionine and valine;

$AA_{10}$ is selected from the group consisting of glutamine, serine and threonine;

$AA_{11}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{12}$ is selected from the group consisting of tyrosine, phenylalanine and tryptophan;

$AA_{13}$ is selected from the group consisting of leucine, isoleucine, methionine and valine;

$AA_{14}$ is selected from the group consisting of threonine, lysine, serine and arginine;

$AA_{15}$ is selected from the group consisting of arginine, alanine, glycine and lysine;

$AA_{16}$ is selected from the group consisting of histidine, asparagine and glutamine;

$AA_{17}$ is selected from the group consisting of valine, isoleucine, leucine and methionine; and $AA_{18}$ is selected from the group consisting of isoleucine, valine, leucine and methionine.

22. The peptide of claim 21 wherein the sequence $AA_1$ through $AA_{18}$ or a subsequence thereof corresponds to the sequence of the αD region of a TGFβ receptor kinase selected from the group consisting of SEQ ID NO:83, SEQ ID NO:84 and SEQ ID NO:85 or a subsequence thereof, with the proviso that any two amino acids in the sequence $AA_1$ through $AA_{18}$ or the subsequence thereof can vary as set forth in claim 21.

23. The peptide of claim 21 wherein the sequence $AA_1$ through $AA_{18}$ or a subsequence thereof corresponds to the sequence of the αD region of a TGFβ receptor kinase selected from the group consisting of SEQ ID NO:83, SEQ ID NO:84 and SEQ ID NO:85 or a subsequence thereof, with the proviso that any one amino acid in the sequence $AA_1$ through $AA_{18}$ or the subsequence thereof can vary as set forth in claim 21.

24. A peptide consisting of a sequence of amino acids $AA_1$ through $AA_{18}$ or a subsequence thereof comprising at least seven amino acids, wherein:

$AA_1$ is selected from the group consisting of threonine and serine;

$AA_2$ is selected from the group consisting of histidine, aspartic acid, glutamic acid and an aliphatic, substituted aliphatic, benzyl, substituted benzyl, aromatic or substituted aromatic ester of glutamic acid or aspartic acid;

$AA_3$ is selected from the group consisting of tyrosine, phenylalanine and tryptophan;

$AA_4$ is histidine;

$AA_5$ is selected from the group consisting of glutamic acid, aspartic acid and an aliphatic, substituted aliphatic, benzyl, substituted benzyl, aromatic or substituted aromatic ester of glutamic acid or aspartic acid;

$AA_6$ is selected from the group consisting of histidine, methionine, asparagine, isoleucine, leucine, valine and glutamine;

$AA_7$ is selected from the group consisting of glycine and alanine;

$AA_8$ is selected from the group consisting of serine and threonine;

$AA_9$ is selected from the group consisting of leucine, isoleucine, methionine and valine;

$AA_{10}$ is selected from the group consisting of tyrosine, phenylalanine and tryptophan;

$AA_{11}$ is selected from the group consisting of aspartic acid, glutamic acid and an aliphatic, substituted aliphatic, benzyl, substituted benzyl, aromatic or substituted aromatic ester of glutamic acid or aspartic acid;

$AA_{12}$ is selected from the group consisting of phenylalanine, tyrosine and tryptophan;

$AA_{13}$ is selected from the group consisting of leucine, isoleucine, methionine and valine;

$AA_{14}$ is selected from the group consisting of glutamine, lysine, asparagine and arginine;

$AA_{15}$ is selected from the group consisting of arginine, leucine, cysteine, serine, lysine, isoleucine, methionine, valine and threonine;

$AA_{16}$ is selected from the group consisting of glutamine, threonine, alanine, tyrosine, asparagine, serine, phenylalanine, tryptophan and glycine;

$AA_{17}$ is selected from the group consisting of threonine and serine; and $AA_{18}$ is selected from the group consisting of leucine, valine, isoleucine and methionine.

25. The peptide of claim 24 wherein the sequence $AA_1$ through $AA_{18}$ or a subsequence thereof corresponds to the sequence of the αD region of an activin receptor-like kinase selected from the group consisting of SEQ ID NO:86, SEQ ID NO:87, SEQ ID NO:88, SEQ ID NO:89 and SEQ ID NO:90 or a subsequence thereof, with the proviso that any two amino acids in the sequence $AA_1$ through $AA_{18}$ or the subsequence thereof can vary as set forth in claim 24.

26. The peptide of claim 24 wherein the sequence $AA_1$ through $AA_{18}$ or a subsequence thereof corresponds to the sequence of the αD region of an activin receptor-like kinase selected from the group consisting of SEQ ID NO:86, SEQ ID NO:87, SEQ ID NO:88, SEQ ID NO:89 and SEQ ID NO:90 or a subsequence thereof, with the proviso that any one amino acid in the sequence $AA_1$ through $AA_{18}$ or the subsequence thereof can vary as set forth in claim 24.

27. A peptide consisting of a sequence of amino acids $AA_1$ through $AA_{34}$ or a subsequence thereof comprising at least five amino acids, wherein:

$AA_1$ is selected from the group consisting of phenylalanine, tryptophan and tyrosine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of tyrosine, phenylalanine and tryptophan;

$AA_4$ is selected from the group consisting of methionine, isoleucine, leucine and valine;

$AA_5$ is selected from the group consisting of arginine and lysine;

$AA_6$ is histidine;

$AA_7$ is selected from the group consisting of glycine and alanine;

$AA_8$ is selected from the group consisting of aspartic acid, glutamic acid and an aliphatic, substituted aliphatic, benzyl, substituted benzyl, aromatic or substituted aromatic ester of glutamic acid or aspartic acid;

$AA_9$ is selected from the group consisting of leucine, isoleucine, methionine and valine;

$AA_{10}$ is selected from the group consisting of asparagine and glutamine;

$AA_{11}$ is selected from the group consisting of arginine and lysine;

$AA_{12}$ is selected from the group consisting of phenylalanine, tryptophan and tyrosine;

$AA_{13}$ is selected from the group consisting of leucine, isoleucine, methionine and valine;

$AA_{14}$ is selected from the group consisting of arginine and lysine;

$AA_{15}$ is selected from the group consisting of serine, alanine, threonine and glycine;

$AA_{16}$ is histidine;

$AA_{17}$ is selected from the group consisting of glycine and alanine;

$AA_{18}$ is proline;

$AA_{19}$ is selected from the group consisting of aspartic acid, glutamic acid and an aliphatic, substituted aliphatic, benzyl, substituted benzyl, aromatic or substituted aromatic ester of glutamic acid or aspartic acid;

$AA_{20}$ is selected from the group consisting of alanine and glycine;

$AA_{21}$ is selected from the group consisting of lysine, valine, methionine, arginine, isoleucine and leucine;

$AA_{22}$ is selected from the group consisting of leucine, isoleucine, methionine and valine;

$AA_{23}$ is selected from the group consisting of leucine, methionine, isoleucine and valine;

$AA_{24}$ is selected from the group consisting of alanine, valine, isoleucine, leucine, methionine and glycine;

$AA_{25}$ is selected from the group consisting of glycine, glutamic acid, aspartic acid, alanine and an aliphatic, substituted aliphatic, benzyl, substituted benzyl, aromatic or substituted aromatic ester of glutamic acid or aspartic acid;

$AA_{26}$ is selected from the group consisting of glycine and alanine;

$AA_{27}$ is selected from the group consisting of glutamic acid, asparagine, glutamine, aspartic acid and an aliphatic, substituted aliphatic, benzyl, substituted benzyl, aromatic or substituted aromatic ester of glutamic acid or aspartic acid;

$AA_{28}$ is selected from the group consisting of aspartic acid, proline, glutamic acid and an aliphatic, substituted aliphatic, benzyl, substituted benzyl, aromatic or substituted aromatic ester of glutamic acid or aspartic acid;

$AA_{29}$ is selected from the group consisting of valine, proline, arginine, isoleucine, leucine, methionine and lysine;

$AA_{30}$ is selected from the group consisting of alanine, threonine, glutamine, serine, asparagine and glycine;

$AA_{31}$ is selected from the group consisting of proline, glutamic acid, alanine, aspartic acid, glycine and an aliphatic, substituted aliphatic, benzyl, substituted benzyl, aromatic or substituted aromatic ester of glutamic acid or aspartic acid;

$AA_{32}$ is selected from the group consisting of proline, glycine and alanine;

$AA_{33}$ is selected from the group consisting of leucine, glutamic acid, isoleucine, methionine, valine, aspartic acid and an aliphatic, substituted aliphatic, benzyl, substituted benzyl, aromatic or substituted aromatic ester of glutamic acid or aspartic acid; and $AA_{34}$ is selected from the group consisting of leucine, isoleucine, methionine and valine, wherein the sequence $AA_1$ through $AA_{34}$ or a subsequence thereof corresponds to the sequence of the αD region of a neurotrophic receptor kinase selected from the group consisting of SEQ ID NO:68 and SEQ ID NO:69 or a subsequence thereof, with the proviso that any two amino acids in the sequence $AA_1$ through $AA_{34}$ or the subsequence thereof can vary as set forth above.

28. A peptide consisting of a sequence of amino acids $AA_1$ through $AA_{34}$ or a subsequence thereof comprising at least five amino acids, wherein:

$AA_1$ is selected from the group consisting of phenylalanine, tryptophan and tyrosine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of tyrosine, phenylalanine and tryptophan;

$AA_4$ is selected from the group consisting of methionine, isoleucine, leucine and valine;

$AA_5$ is selected from the group consisting of arginine and lysine;

$AA_6$ is histidine;

$AA_7$ is selected from the group consisting of glycine and alanine;

$AA_8$ is selected from the group consisting of aspartic acid, glutamic acid and an aliphatic, substituted aliphatic, benzyl, substituted benzyl, aromatic or substituted aromatic ester of glutamic acid or aspartic acid;

$AA_9$ is selected from the group consisting of leucine, isoleucine, methionine and valine;

$AA_{10}$ is selected from the group consisting of asparagine and glutamine;

$AA_{11}$ is selected from the group consisting of arginine and lysine;

$AA_{12}$ is selected from the group consisting of phenylalanine, tryptophan and tyrosine;

$AA_{13}$ is selected from the group consisting of leucine, isoleucine, methionine and valine;

$AA_{14}$ is selected from the group consisting of arginine and lysine;

$AA_{15}$ is selected from the group consisting of serine, alanine, threonine and glycine;

$AA_{16}$ is histidine;

$AA_{17}$ is selected from the group consisting of glycine and alanine;

$AA_{18}$ is proline;

$AA_{19}$ is selected from the group consisting of aspartic acid, glutamic acid and an aliphatic, substituted aliphatic, benzyl, substituted benzyl, aromatic or substituted aromatic ester of glutamic acid or aspartic acid;

$AA_{20}$ is selected from the group consisting of alanine and glycine;

$AA_{21}$ is selected from the group consisting of lysine, valine, methionine, arginine, isoleucine and leucine;

$AA_{22}$ is selected from the group consisting of leucine, isoleucine, methionine and valine;

$AA_{23}$ is selected from the group consisting of leucine, methionine, isoleucine and valine;

$AA_{24}$ is selected from the group consisting of alanine, valine, isoleucine, leucine, methionine and glycine;

$AA_{25}$ is selected from the group consisting of glycine, glutamic acid, aspartic acid, alanine and an aliphatic, substituted aliphatic, benzyl, substituted benzyl, aromatic or substituted aromatic ester of glutamic acid or aspartic acid;

$AA_{26}$ is selected from the group consisting of glycine and alanine;

$AA_{27}$ is selected from the group consisting of glutamic acid, asparagine, glutamine, aspartic acid and an aliphatic, substituted aliphatic, benzyl, substituted benzyl, aromatic or substituted aromatic ester of glutamic acid or aspartic acid;

$AA_{28}$ is selected from the group consisting of aspartic acid, proline, glutamic acid and an aliphatic, substituted aliphatic, benzyl, substituted benzyl, aromatic or substituted aromatic ester of glutamic acid or aspartic acid;

$AA_{29}$ is selected from the group consisting of valine, proline, arginine, isoleucine, leucine, methionine and lysine;

$AA_{30}$ is selected from the group consisting of alanine, threonine, glutamine, serine, asparagine and glycine;

$AA_{31}$ is selected from the group consisting of proline, glutamic acid, alanine, aspartic acid, glycine and an aliphatic, substituted aliphatic, benzyl, substituted benzyl, aromatic or substituted aromatic ester of glutamic acid or aspartic acid;

$AA_{32}$ is selected from the group consisting of proline, glycine and alanine;

$AA_{33}$ is selected from the group consisting of leucine, glutamic acid, isoleucine, methionine, valine, aspartic acid and an aliphatic, substituted aliphatic, benzyl, substituted benzyl, aromatic or substituted aromatic ester of glutamic acid or aspartic acid; and $AA_{34}$ is selected from the group consisting of leucine, isoleucine, methionine and valine, wherein the sequence $AA_1$ through $AA_{18}$ or a subsequence thereof corresponds to the sequence of the αD region of a neurotrophic receptor kinase selected from the group consisting of SEQ ID NO:68 and SEQ ID NO:69 or a subsequence thereof, with the proviso that any one amino acid in the sequence $AA_1$ through $AA_{31}$ or the subsequence thereof can vary as set forth above.

29. A peptide consisting of a sequence of amino acids $AA_1$ through $AA_{21}$ or a subsequence thereof comprising at least five amino acids, wherein:

$AA_1$ is selected from the group consisting of threonine and serine;

$AA_2$ is histidine $AA_3$ is selected from the group consisting of tryptophan, phenylalanine and tyrosine;

$AA_4$ is selected from the group consisting of isoleucine, leucine and methionine;

$AA_5$ is proline;

$AA_6$ is selected from the group consisting of tyrosine, phenylalanine and tryptophan;

$AA_7$ is selected from the group consisting of glycine and alanine;

$AA_8$ is selected from the group consisting of serine and threonine;

$AA_9$ is selected from the group consisting of leucine, isoleucine, methionine and valine;

$AA_{10}$ is selected from the group consisting of tyrosine, phenylalanine and tryptophan;

$AA_{11}$ is selected from the group consisting of asparagine and glutamine;

$AA_{12}$ is selected from the group consisting of valine, isoleucine, leucine and methionine;

$AA_{13}$ is selected from the group consisting of leucine, isoleucine, methionine and valine;

$AA_{14}$ is histidine;

$AA_{15}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{16}$ is selected from the group consisting of glycine and alanine;

$AA_{17}$ is selected from the group consisting of threonine and serine;

$AA_{18}$ is selected from the group consisting of asparagine and glutamine;

$AA_{19}$ is selected from the group consisting of phenylalanine, tryptophan and tyrosine;

$AA_{20}$ is selected from the group consisting of valine, isoleucine, leucine and methionine; and $AA_{21}$ is selected from the group consisting of valine, isoleucine, leucine and methionine.

30. The peptide of claim 29 wherein the sequence $AA_1$ through $AA_{21}$ or a subsequence thereof corresponds to the sequence of the αD region of SEQ ID NO:93 or a subsequence thereof, with the proviso that any two amino acids in the sequence $AA_1$ through $AA_{21}$ or the subsequence thereof can vary as set forth in claim 29.

31. The peptide of claim 29 wherein the sequence $AA_1$ through $AA_{21}$ or a subsequence thereof corresponds to the sequence of the αD region of SEQ ID NO:93 or a subsequence thereof, with the proviso that any one amino acid in the sequence $AA_1$ through $AA_{21}$ or the subsequence thereof can vary as set forth in claim 29.

32. A peptide consisting of a sequence of amino acids $AA_1$ through $AA_{22}$ or a subsequence thereof comprising at least five amino acids, wherein:

$AA_1$ is selected from the group consisting of methionine, isoleucine, leucine and valine;

$AA_2$ is selected from the group consisting of glutamic acid, aspartic acid and an aliphatic, substituted aliphatic, benzyl, substituted benzyl, aromatic or substituted aromatic ester of glutamic acid or aspartic acid;

$AA_3$ is selected from the group consisting of tyrosine, phenylalanine and tryptophan;

$AA_4$ is selected from the group consisting of cysteine and serine;

$AA_5$ is selected from the group consisting of serine, glutamine, threonine and asparagine;

$AA_6$ is selected from the group consisting of glycine and alanine;

$AA_7$ is selected from the group consisting of glycine and alanine;

$AA_8$ is selected from the group consisting of aspartic acid, glutamic acid and an aliphatic, substituted aliphatic, benzyl, substituted benzyl, aromatic or substituted aromatic ester of glutamic acid or aspartic acid;

$AA_9$ is selected from the group consisting of leucine, isoleucine, methionine and valine;

$AA_{10}$ is selected from the group consisting of arginine and lysine;

$AA_{11}$ is selected from the group consisting of lysine and asparagine;

$AA_{12}$ is selected from the group consisting of leucine, tyrosine, isoleucine, methionine, valine, phenylalanine and tryptophan;

$AA_{13}$ is selected from the group consisting of leucine, isoleucine, methionine and valine;

$AA_{14}$ is selected from the group consisting of asparagine and glutamine;

$AA_{15}$ is selected from the group consisting of lysine, glutamine, arginine and asparagine;

$AA_{16}$ is selected from the group consisting of proline, phenylalanine, tryptophan and tyrosine;

$AA_{17}$ is selected from the group consisting of glutamic acid, aspartic acid and an aliphatic, substituted aliphatic, benzyl, substituted benzyl, aromatic or substituted aromatic ester of glutamic acid or aspartic acid;

$AA_{18}$ is selected from the group consisting of asparagine and glutamine;

$AA_{19}$ is selected from the group consisting of cysteine and serine;

$AA_{20}$ is selected from the group consisting of cysteine and serine;

$AA_{21}$ is selected from the group consisting of glycine and alanine; and $AA_{22}$ is selected from the group consisting of leucine, isoleucine, methionine and valine.

33. The peptide of claim 32 wherein the sequence $AA_1$ through $AA_{22}$ or a subsequence thereof corresponds to the sequence of the αD region of an I-kappa B kinase selected from the group consisting of SEQ ID NO:79 and SEQ ID NO:80 or a subsequence thereof, with the proviso that any two amino acids in the sequence $AA_1$ through $AA_{22}$ or the subsequence thereof can vary as set forth in claim 32.

34. The peptide of claim 32 wherein the sequence $AA_1$ through $AA_{22}$ or a subsequence thereof corresponds to the sequence of the αD region of an I-kappa B kinase selected from the group consisting of SEQ ID NO:79 and SEQ ID NO:80 or a subsequence thereof, with the proviso that any one amino acid in the sequence $AA_1$ through $AA_{22}$ or the subsequence thereof can vary as set forth in claim 32.

* * * * *